(12) United States Patent
Bieker

(10) Patent No.: US 8,927,502 B2
(45) Date of Patent: Jan. 6, 2015

(54) EMBEDDED CHIMERIC PEPTIDE NUCLEIC ACIDS AND USES THEREOF

(75) Inventor: James J. Bieker, Bronx, NY (US)

(73) Assignee: ICahn School of Medicine at Mount Sinai, New York, NY (US)

( * ) Notice: Subject to any disclaimer, the term of this patent is extended or adjusted under 35 U.S.C. 154(b) by 0 days.

(21) Appl. No.: 13/585,554

(22) Filed: Aug. 14, 2012

(65) Prior Publication Data

US 2013/0078227 A1  Mar. 28, 2013

Related U.S. Application Data

(63) Continuation-in-part of application No. PCT/US2011/025128, filed on Feb. 16, 2011, and a (Continued)

(51) Int. Cl.
*A61K 38/10* (2006.01)
*C12N 5/074* (2010.01)

(Continued)

(52) U.S. Cl.
CPC ......... *C12N 5/0696* (2013.01); *A61K 47/48338* (2013.01); *C07K 7/08* (2013.01); *A61K 47/48246* (2013.01); *C07K 7/06* (2013.01); *A61K 47/48238* (2013.01); *C07K 14/003* (2013.01); *C12N 2501/125* (2013.01); *C12N 2501/26* (2013.01); *C12N 2501/602* (2013.01); *C12N 2501/603* (2013.01); *C12N 2506/11* (2013.01); *A61K 38/00* (2013.01)
USPC .......................... 514/21.5; 514/21.6; 514/21.4

(58) Field of Classification Search
CPC ............ A61K 38/00; A61K 47/48246; A61K 47/48338; A61K 31/713; A61K 49/14; A61K 47/48238; C12N 2310/3513; C12N 2310/3181; C12N 2310/351; C12N 2501/60; C07K 14/003
See application file for complete search history.

(56) References Cited

U.S. PATENT DOCUMENTS

2005/0054836 A1 3/2005 Krainer et al.
2005/0256051 A1 11/2005 Morris

FOREIGN PATENT DOCUMENTS

WO  WO 2011/103215  8/2011
WO  WO 2012/075027  6/2012

OTHER PUBLICATIONS

Corey et al., Strand invasion by mixed base PNAs and a PNA-Peptide Chimera, Nucleic Acids Research vol. 28(17):3332-3338 (2000).*

(Continued)

*Primary Examiner* — Randall L Beane
(74) *Attorney, Agent, or Firm* — John P. White; Cooper & Dunham LLP

(57) ABSTRACT

The present invention relates to an ecPNA having the general structure:

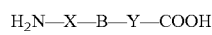

and uses thereof, wherein X is A or C and Y is A or C with the proviso that when X is A, Y is C, and when X is C, Y is A; A represents an oligopeptide structure, the sequence of which comprises a sequence which renders the compound able to enter the nucleus of a cell; B represents a peptide nucleic acid (PNA) structure at least 12 nucleotides in length, the sequence of which is capable of hybridizing with a DNA within the nucleus of the cell, which DNA is within a promoter region of a gene; C represents an oligopeptide structure; and each — represents a chemical linkage between the structures at each side thereof, which may be the same as or different from each other such linkage.

1 Claim, 38 Drawing Sheets
(1 of 38 Drawing Sheet(s) Filed in Color)

Related U.S. Application Data continuation-in-part of application No. PCT/US2011/062423, filed on Nov. 29, 2011.

(60) Provisional application No. 61/338,316, filed on Feb. 16, 2010, provisional application No. 61/534,240, filed on Sep. 13, 2011, provisional application No. 61/417,760, filed on Nov. 29, 2010.

(51) Int. Cl.
  *A61K 47/48* (2006.01)
  *C07K 7/08* (2006.01)
  *C07K 7/06* (2006.01)
  *C07K 14/00* (2006.01)
  *A61K 38/00* (2006.01)

(56) References Cited

OTHER PUBLICATIONS

Suzuki et al, DBTSS: DataBase of human Transcription Start Sites and full-length cDNAs, Nucleic Acid Research (2002) vol. 30(1):328-331.*
Fei et al (The influence of net charge and charge distribution on cellular uptake and cytosolic localization of arginine-rich peptides, Journal of Drug Targeting (Sep. 2011) vol. 19(8):675-680.*
Heitz et al., Twenty years of cell-penetrating peptides: from molecular mechanisms to therapeutics, British Journal of Pharmacology (2009), 157, 195-206.*
Tonelli et al., Mol Cancer Ther (2005), vol. 4:779-786.*
ncbi.nlm.nih.gov, Homo Sapiens chromosome 4, GRch38 Primary Assembly, NCBI Reference Sequence: NC_000004.12:37.6M-37.7M, attached as pdf, generated Feb. 28, 2014.*
Forne et al, Quantitative analysis of chromosome conformation capture assays (3C-qPCR), Nature Protocols vol. 2(7):1722-1733 (2007).*
Hu et al, Inhibiting Gene Expression with Peptide Nucleic Acid (PNA)-Peptide Conjugates that target Chromosomal DNA, Biochemistry 46(25):7581-7589 (Jun. 2007).*
Jul. 21, 2011 International Search Report, issued in connection with PCT International Patent Application No. PCT/US2011/025128.
Jul. 21, 2011 Written Opinion of the International Searching Authority, issued in connection with PCT International Patent Application No. PCT/US2011/025128.
Aug. 21, 2012 International Preliminary Report on Patentability, issued in connection with PCT International Patent Application No. PCT/US2011/025128.
De Koning et al. (2003) "Synthetic Developments towards PNA Peptide Conjugates." Current Opinion in Chemical Biology, 7:734-740.
Apr. 16, 2012 International Search Report, issued in connection with PCT International Patent Application No. PCT/US2011/062423.
Chen et al. (2010) "Design of embedded chimeric peptide nucleic acids that efficiently enter and accurately reactivate gene expression in vivo" Proc Natl Acad Sci USA 107 (39): 16846-16851.
Jun. 4, 2013 International Preliminary Report on Patentability, issued in connection with PCT International Patent Application No, PCT/US2011/062423.
Braun, K. et al., A biological transporter for the delivery of peptide nucleic acids (PNAs) to the nuclear compartment of living cells. J Mol Biol 318, 237-243 (2002).
Bresnick, E.H., Martowicz, M.L., Pal, S. & Johnson, K.D., Developmental control via GATA factor interplay at chromatin domains. J Cell Physiol 205, 1-9 (2005).
Cutrona, G. et al., Effects in live cells of a c-myc anti-gene PNA linked to a nuclear localization signal. Nat Biotechnol 18, 300-303 (2000).
Gluckman, E., and Rocha, V. Cord blood transplantation: state of the art. Haematologica; 94, 451-454 (2009).

Hochedlinger and Plath, Epigenetic reprogramming and induced pluripotency. 136;509-523 (2009).
Hu, J. et al., Allele-specific silencing of mutant huntingtin and ataxin-3 genes by targeting expanded CAG repeats in mRNAs. Nat Biotechnol 27, 478-484 (2009).
Janowski, B.A. et al. Inhibiting transcription of chromosomal DNA with antigene peptide nucleic acids. Nat Chem Biol 1, 210-215 (2005).
Kaihatsu, K., Janowski, B.A & Corey, D.R., Recognition of chromosomal DNA by PNAs. Chem Biol 11, 749-758 (2004).
Krumlauf, R., Hox genes in vertebrate development. Cell 78, 191-201 (1994).
Kurian, K.M. et al. (2000) J Clin Pathol: Mol Pathol; 53:173-176.
Loh, Y. et al. Generation of induced pluripotent stem cells from human blood. Blood; 113(22):5476-5479 (2009).
Lowry, W.E., et al. Generation of human induced pluripotent stem cells from dermal fibroblasts. Proc. Natl. Acad. Sci. USA 105, 2883-2888 (2008).
Maherali, N., et al. Directly reprogrammed fibroblasts show global epigenetic remodeling and widespread tissue contribution.Cell Stem Cell; 1, 55-70 (2007).
Nielsen, P.E., Egholm, M., Berg, R.H. & Buchardt, O., Sequence-selective recognition of DNA by strand displacement with a thymine-substituted polyamide. Science 254, 1497-1500 (1991).
Nielsen, P.E., Addressing the challenges of cellular delivery and bioavailability of peptide nucleic acids (PNA). Q Rev Biophys 38, 345-350 (2005).
Nielsen, P.E., PNA Technology. Mol Biotechnol 26, 233-248 (2004).
Noordermeer D., de Laat W., Joining the loops: β-globin gene regulation. IUMMB Life 60, 824-833 (2008).
Okita et al, Generation of germline-competent induced pluripotent stem cells. Nature 448: 313-317 (2007).
Orum et al., Single base pair mutation analysis by PNA directed PCR clamping. Nucleic Acids Research 21(23):5332-5336 (1993).
Park, et al. Reprogramming of human somatic cells to pluripotency with defined factors. Nature 451, 141-146 (2008).
Pooga, M., Land, T., Bartfai, T. & Langel, U., PNA oligomers as tools for specific modulation of gene expression. Biomol Eng 17, 183-192 (2001).
Rocha et al., Transplants of Umbilical-Cord Blood or Bone Marrow from Unrelated Donors in Adults with Acute Leukemia. N. Engl. J. Med. 351, 2276-2285 (2004).
Schechter, A.N., Hemoglobin research and the origins of molecular medicine. Blood 112, 3927-3938 (2008).
Stadtfeld and Hochedlinger, Induced pluripotency: history, mechanisms, and applications. Genes Dev; 24:2239-2263 (2010).
Takahashi, K., and Yamanaka, S. Induction of Pluripotent Stem cells from Mouse Embryonic and Adult Fibroblast Cultures by Defined Factors. Cell, 126, 663-676 (2006).
Takahashi, K. et al. Induction of Pluripotent Stem Cells from Adult Human Fibroblasts by Defined Factors. Cell 131, 861-872 (2007).
Yu, J. et al. Induced pluripotent stem cell lines derived from human somatic cells. Science; 318, 1917-1920 (2007).
Zhang, X., Ishihara, T. & Corey, D.R., Strand invasion by mixed base PNAs and a PNA-peptide chimera. Nucleic Acids Res 28, 3332-3338 (2000).
Atweh, G.F. & Schechter, A.N., Pharmacologic induction of fetal hemoglobin: raising the therapeutic bar in sickle cell disease. Curr Opin Hematol 8, 123-130 (2001).
Nielsen, P.E., Peptide nucleic acids as antibacterial agents via the antisense principle. Expert Opin Investig Drugs 10, 331-341 (2001).
Zhilina et al., Peptide Nucleic Acid Conjugates: Synthesis, Properties and Applications. Current Topics in Medicinal Chemistry 4:1119-1131 (2005).

* cited by examiner

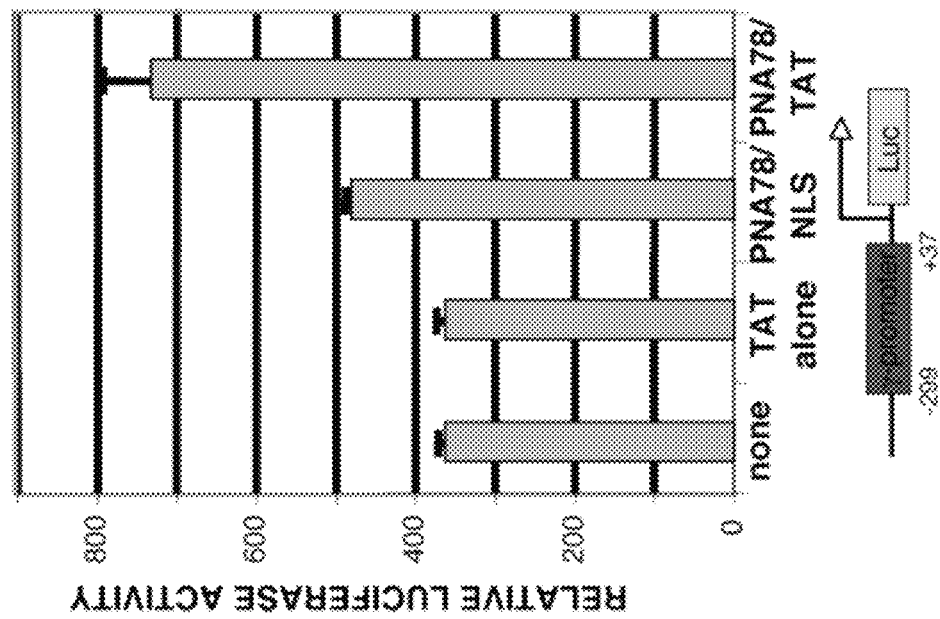

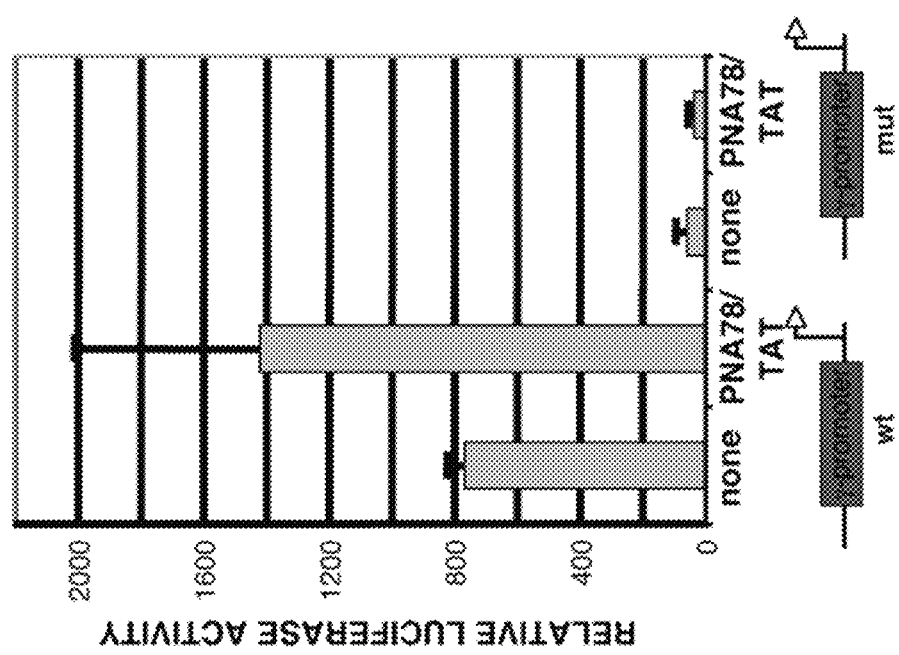

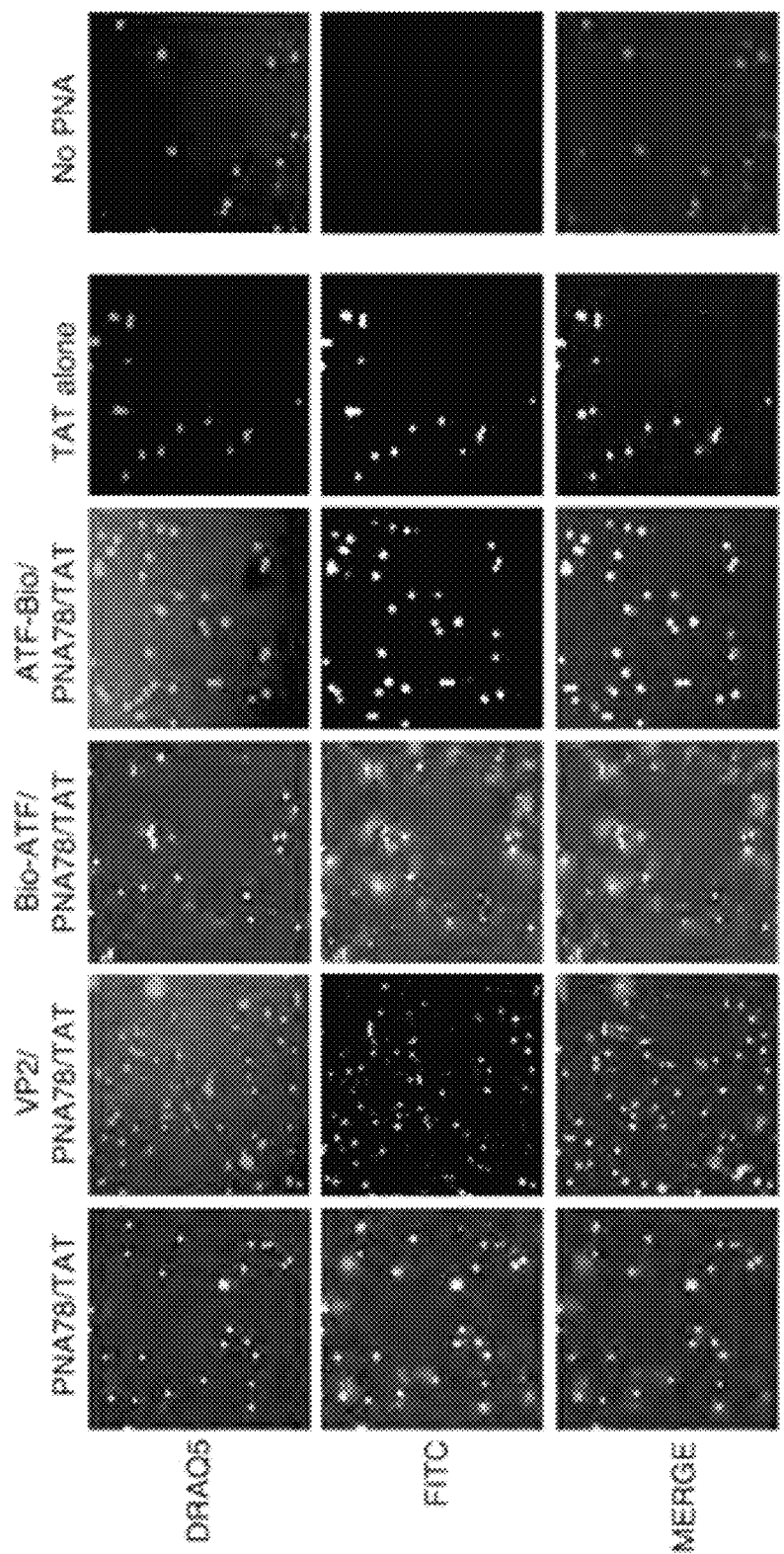

FIGURE 7

OCT4 (Pou5F1)
Human

GGCTGTTGATGCATTGAGGGATAGCGCCACACACATTCAATAAATTTGAGGAGTGACTGGCCCCTGAAGGCACAGTGCCAGAGGTCTGT
GGAGAGGGGGTCAAGCGGGTTCCTGAAGACATGGAGGTGTGGATTGATTCCAGAGCTGAGATGTGCTGAGAGAGTGCCAGGAGCC
GGTTGGGGAGTTGAAAGTTGGATGTGGTGGCTCACGCCTTTAATCATGACACTGGGCGCAGAGCGGGAGGATTCTTGAGGACAGGAGGAATTCAAGACCAG
CCTGGGTAACATAGCAAGGCCCCATCTCTACTAAAAATAAAAACTAACAGGGCCATCATTGAGCCACTGCTAGTCCCAGCCACTTAGGAGGCTGAGC
AGAAGGATTGCTTTGGCCCAGTAGATCGAGTGGGGACCTACATTGAGCCATCATTGAGCCACTCAGTCTGGGCAACAAAGTGAGACCCTGTCTTAAAA
AATAAAATAAAAAAGTTTCTGTGGGGA<u>CCTGCACTGAGGTCCTGGCTTCTTCTCCCCCACCTCCCTCCCCGTTTTCCCCTTCACAGACACCATTGCCA
CCACCATTAGGCAAACATCCTTCGCCTCAGTTCTCCCCGCAAGCCCTCATTTCACCAGGCCCCCCGGCTTGGGGCGCCTTCCTTCCCCATGGCGGGACACTGG</u>
                                                                                                                                   M  A  G  H  L
CTTCGGATTTCGCCTTCTCGCCCCCTTCGCCCCCTTCCAGGTGGTGGAGTGATGGGCCAGGGGGCCGGAGCCGGCTGGGTTGATCCTCGACCTGGCTAAGCTTCCA
 L  R  F  S  P  P  G  G  G  D  G  P  G  G  P  E  P  G  W  V  D  P  R  T  W  L  S  F  Q
AGGCCCTCCTGGAGGCCCAGGAATCGGGCCCCAGGCCTCTGAGGTTGGGGAGTGTGGGGATTCCCCCATGCCCCGTATGAGTTCTGTGGGGGG
 G  P  P  G  G  P  G  I  G  P  G  S  E  V  W  G  I  P  P  C  P  P  P  Y  E  F  C  G  G
ATGGCGTACTGTGGCCCCAGTTGAGTGGGCTAGTGCCCAAGGCGCTTGGAGACCTTCTCAGCTCAGCTTGAGGGCGAAGCAGGAGTCGGGGTGGAGAGCA
 M  A  Y  C  G  P  Q  V  G  V  G  L  V  P  Q  G  G  L  E  T  S  Q  P  E  G  E  A  G  V  G  V  E  S
ACTCCGATGGGCCTCCCCGAGCCCTGCACCGTCACCCGTTGGTGCCCGTGAAGCTGGAGAAGGAGAAGCTGGAGAACCCGGAGGAGGCAAGTGAGCT
 N  S  D  G  A  S  P  E  P  C  T  V  T  P  G  A  V  K  L  E  K  E  K  L  E  Q  N  P  E  E

FIGURE 8

SOX2
human

AAGAGAGGAGAGCGGAAGAGCCGAGTACGGGAGCGGCACCAGAGGGGCACCCAGCCACACCAGAACAATGACACACCAACTCCTGCACTG
GCTGTTTCCAGAAATACGAGTTGGACAGCCGCCTGAGCCAAAAAAATTAAGTTAAGCCGCCCTTAGCTGTCTTCCCGCACCTGCTTCCCATCCTCATTTAAGTACCCTG
CACCAAAAAGTAAATCAATATTAAGTTTAAAGAAGAAAAAACCCACGTAGTCTTTAGTGCTGTTTACCTGCCTTCTTCGAAAAGGCGTGTGTGTGTCCCCGCGTGTGCTGCGAG
AGGGGATACAAAAGTTTCTCAGTGGCTGGCAAGGCTGGGCTGGGCTCTGGGAGCCTCCTGGGGCTCTGGGGCTGGGGCTGGGTCTGAGTGGAGCGCGGCTGGAGCAGCGCCAGCCCGAGCCAGCC
AGGCCCGCCCTTTCATGCAAAACCCGGCTAGCCCGGCTGGGCTGGGCTGAGTGGTGCAAAAGGGAAAGTAGTTGCTGCCTCTTAAGACT
TCACATGATGGTTGTCTATTAACTTGGTCAAAAAGTATCAGGAGTTGTCAAGGCAGAGAAGTTTGAGCCTAAGGGGAAGTCTTTGCAAAAATAATAATAACAATCATCGGCGGGGCAGGATCGG
AGGACTGAGAGAAAGAGAAGGAGAAAAGAAGCGCTTTTTTGATCCTGATTCCAGTTGCCCTTGCCCAGTTGCCCTGATTTTCGCTGATTTCTCGCGAGCCCTGCGCTCCCG
ACACCCCCCGCCGCCCGCCCTCCCCTCCCCCAAGTCCCGGCCCCGGAGGGTCCGGCCGGCCAACTCCACCGCGCCAACTCCAACCAGCCGCC
CGCATGTACAACATGATGGAGACGGAGCTGAAGCCGCCGCCCGGCCCGCAGCAACTTCGGGGGCGGCGGCAACTCCACCGCGCCAACTCCAACCAGAAAAA
M Y N M M E T E L K P P P G P P Q Q T S G G G G N S T A A A A G G N Q K N

FIGURE 9

KLF4
human

CGGCTCCAGCCCGCCAGCTGCCTGGCTGGCGTCACGGCCCGCCCAGCCCCGCCCCCACGTGCGCCGAGTTTGT
TGATTTAGCTGCCATAGCAACGATGGAAGGAGCCTCGGGGGCGGAGAAGAAAGGGGAGGCGGAGGAAAGGCTGTA
GCGAAGGAAGTTATAAGTAAGGAACGCGCGGCGGCAGTTTCCCGACCAGAGAGAACGAACGTGTCTGCGGGGCGTG
GCGGGGCGGCGGCCACCGGGAGCCGCCGAGTGACCCCTCCCCGCCGAGTCTCCGCCGTGCCGTGGAGTCAGGCGGC
GCTCCACACAACTCACCGGAGTCCGCCGCCACTCGAGGCCACTGTCTCACCTGGAGCAGCTCACCTCGCCCACC
GCCCCGGCCAGCCCCTGCCCACCGCAGCCCACTGGTCTGAGTGGACTGCTGAGTGCTGAGAGAGCAGCCCGGCCACCGGA
CCTACTTACTCGCCTTGCTGATTGTCTATTTTGCGTTTACAACTTTTGTATACAAAGAACTTTTTAAAAAGACGCTTCAAGTTA
TATTTAATCCAAAGAAGAAGGATCTCGGCCAATTTGGGGTTTTGGCTTTTGCTTTCTTCTTCGTTGACTTTGGGTTCCCCAGCTGC
TTCGGGCTGCCGAGGACCTTCTGGGCCCCCACATTAATGAGGTAGGTGAGGCGCGCTGGGAGCCAGGAGGGGTGAGGACCGGTGAGGACGCGCCGG

M   R
AACGACGGGCCGAAAGCCCGCCCCCTGACTCTCCCTGTCTCCCCGCTCCCGCAGGCAGCCACCTGGCGAGTCTGACATGGCTGTCAGCGACGCGCT
                                         Q   P   P   G   E   S   D   M   A   V   S   D   A   L

FIGURE 10

C-MYC human

ATGATTTATACTCACAGGACAAGGATGCGGTTTGTCAAACAGTACTGCTACGGAGGAGCAGCAGAGAAAGGGAGAGGGTTTGAGAGGAGCAAAAGAAAA
TGGTAGGCGCGCGTAGTTAATTCATGCGGCTCTCTTACTCTGTTTACATCCTAGAGAGTGCTCGGCTGCCCGGCTGAGTCTCCTCCCCACCTTCCC
CACCCTCCCCACCCTCCCCATAAGCGCCCCCTCCCGGGTTCCCAAAGCAGAGGGAAAAGAAAGATCCTCTCGCTCCTCCGCTAATCTCCGCCCACC
GGCCCTTTATAAATGCGAGGGTCTGGACGGCTGAGGACCCCGAGCTGTGCTGCTCCCGGCCCCGGTATAAAAGCCGGTTTCGGGGCTTTATCTAACT
CCTCGAGAAGGGCAGGGCTTCTCAGAGGCTTGGCGGGAAAAGAACGGAGGGAGGATCGCGCTGAGTATAAAAGCCGGTTTTCGGGGCTTTATCTAACT
CGCTGTAGTAATTCCAGCGAGAGGCAGAGGGAGCCAGCCGCCCGCCAGCGGGCCGAGTAGGGTGGAAGAGCCGGGTCCGCAACCCTTGCCGCTTTGC
GGAGATCCGGAGCGAATAGGGGCACTTTGCACTGGAACTTACAACACCCGAGCAAGGACGCTCTCCAGCGTGCTTAGACGCTGATTTTTTCGGGTAGTGGAAAACCAGTAAGCACCGA
CCATAGCAGCGGGCGGGCACTTTGCACTGGAACTTACAACACCCGAGCAAGGACGCTCTCCAGCGTGCTTAGACGCTGATTTTTTCGGGTAGTGGAAAACCAGTAAGCACCGA
TTCCCCGCCGCTGCCAGGACCCCGCTTCTCTGAAAGGCTCTCCTTGCAGCGTGCTTAGACGCTGATTTTTTCGGGTAGTGGAAAACCAGTAAGCACCGA

LIN28
Human

GCCAGGCTCACACCTCCCCTCCCCCCAACTCTCTGAATGTATAATTATCTGCCCGGGGCTGGGGGTGGTGTGTGTGTGTGTGTGTGTGTGTG
TGTGTGCAGTCAGTGTTTTAAAACTACCCCCCCACCAGTCCCCCACCTGTATCTGAGTCCTTGGGACCCCTCAAAGTGCAGATCTCAAA
TTCCGGGTACTCAAGTCTTCTAGGCAGACAGACCCATCTCCAGTTGTGCGTCTCAAGGGGTGTC<u>AAACCTCAAGGTTCTGAGAAGGGACACCCCA</u>
<u>GAGGTGTCAGAGACCGGAGTTGTGGGGAGGGCCGGAGTCGGAAAGGAGAGGGAAGGGGGCTGCCCGGCGG</u>
<u>GGGGTTGGGTCATTGTCTTTAGAATTTGGGAGCCCTTTGAAAAAGCCGTGGGCCCTCCCACCGTATTGTGCGGGGGAAGATGTAGCAGCTTCTTCTCGA</u>
<u>ACCAACCCTTTGCCTTCGGACTTCTCCAGCAGCCCCAGCCCCCGCCAGGGCCCCGACCCAGGGCCACGACCCTCAGCCGCTCAGCGACGACC<ins>ATG</ins>GGCTCCGTGTCCAACC</u>
                                                                         M  G  S  V  S  N

FIGURE 16

NANOG Human

TACAGACACCCACCACCCATGCGTGGCCTAATTTTTGTATTTTTAGTAGAGAGGGGGGTTTCGCCCATGTTGGCCAGGCTGGTTTCAAACTCCTGACTTCAGGT
GATCCGCCTGCCACGGCCTCCCAATTTACTGGGATTACAGGGGTGGGCCACCGCGCCCGGCCTTTTCTTAATTTTTAAAAATATTAAAGTTTATCCCA
TTCCTGTTGAACCATATTCCCTGAATTTAAAAGTTGGTGAACCTGGTGAACCTAGAAGTATTTGTTGCTTCAGGTTGTTGCTCGTTGCTCGGTTTTCT
AGTTCCCCACCCACCAGTCTGCTGGGTTACTCTGAGGACCCTTCAATGGCCTACTTTTGCTGTGAGACTGGTAGAGACTCGGATTAACGTTCTGCTGGACTGAG
TCAGTAGGGGTGTGCCGCCAGGAGGGTGGGTCTCAAGGTGATAGAGCCTTCATTATAAATCTAGAGACTTCGGATTTAACGTTCTGCTGGACTGAG
CTGGTTGCCTCATGTTATTATGCAGGCAACTTCATCTATCCCAATTTCTGATACTTTTTCTCTTGGGAGGTCCTATTTCTCTAACATCTTCCAGAAAAGT
CTTAAAGCTGCCTTAACCTTTTTTCCAGTCCTCCACCTCCCTCTCCCTAACATGAGTGTGGATCCAGCTTGTCCCCAAAGCT
M  S  V  D  P  A  C  P  Q  S

FIGURE 17

Prdm14
human

[DNA sequence with translated protein sequence beginning M A L P R P S E A V P Q D K V at the end]

FIGURE 18

```
Nfrkb
human

AAACTACTCTCTTCCAGGAAGGGAAGAACATTAGCTCGGCCCGGCCGGCCTTCTCTGGTCCCATCCACACAGAACTGAGGATGGTCTCTGCGCCACTGCT
GGGAGTACCTGGAATAAGTAGTGTGAAGCCTACTAAGCAAAACCCAGTGAATAACAGGAAGGGGCCTTCATATCTTAAGAAGAGGAAAATGATGGAGTT
TAACTTTAAAATGTGATCCTTCGATGGTGTTTACATTCTTTCTCGACATCGAAGGGACCGGAAGGAGGAATGAAGGAACTCGGAAGCACAGGCTG
AGGTCGCGTTCTACTCATGTCCTCAACTGTAAAAATGGCACTAATAGTGCATAGCTGCCTTCGCTCAGCACAAAGACGGTGGTAGAAAGTGCTTAGCA
TAGGGCCTGGGCAGGGTATCTCTCTGCAAACGTGCAGCTAATAGAACGTGCCTTCGCTCAGCGTGAGAAGCGCAAGCAGGCCCTACCGGACTTTGATTCGCCGGTCAGGCAAGGACACGG
CACTGTCTGGGGCCTCTGAGCGGCTCCCAGGACCCGGAACGCGCAAGACCCTGTGGCCCCGCACCCTCCAGCACCCTCTCCAGGCGCAGCTGGAACCTGGAACCTGCATCCCCAGGCCGCAGGGCCCAGGCACCCCTCGCGCCGA
CCCTCCGCTCTCCCGAGCCGCTCCCGAGACTCCTTGCGCACCCAGACTCCTTGCGGAGCCCTGTGGCCCCTGGCACCCTCCAGGCACCCCTCGCGCCGA
GGCCCCAGAGCGTGCGCGCACCCAGACTCCTTGCGGAGCCCTGTGGCCCCGGAGCCCCGGAGGCGCTGGGAGGCCGGGCGCCGCCCGCCCGCGG
TTCAGGTGAGGCGGCGCAAGGGTTGAAGGGTTCTCCTGGAGTGGGGACGGGGACGGCGCTGGGCCCCGCGTGGCTCCGGCAGGTCGCTGCCCGT
GTGGGCGTGGAGGCGGAGCGGGAGGCGGTGGGGAGCGGTGCGACGCGTGAGCCCCTGTGTTAGGGTTAGGCACGGGCGGGGGCCGGGGCCTGAGCCG
TCCAGTTCTGAGGATTGAGACCCGGCCCTTGCGTTGGGAGGGTGGAATTTGCTCGAGAGTTCAGGGCTTTGAGCCCGGTTGCTCTG
GAAGGACCCGAGGGTTTAGCTTCTGCGTTGGGGAGGGTCCAGCGGGAGAAGTTAGACCAGTGCTGAAAGCCAGTGTCTGAAAAGCCCGAGTGAATGAGAGCCCAGAGGCCCCTTCGTG
GTCTAGTGAAGATAGTGGCAGTGCAAGGTTGTCAGTGGACTAGAATCTGGAACTAGCAGGCTTTGGCTGTCAACCTCAATCCCTGGCACTGTCGCAGCTGCCTGGTTTTGGTATTTGTGAGATTCTG
TTCAGAATAGTGGCAGTGCAAGGTTGTCAGTGGACTAGAATCTGGAAATCCCGAACTGAGTCAGTCAAGCTGAAGAAACTTGTGAGCATGCAAGTTGTATAGAGAC
CTCCTAAGAGGCAGGTAGGACACTGACTTTTGAACTTTGTTAAACTCACATGCTCTCTATGCCAGTTCTGTTCTAAGAAGGTTTATTCTGACATCAGGTTGCTTCTGCA
ATTTTTTTTGCGTCTAGTTTGAACTTTTGAACTTTGTAACTCACATGCTGGACCACCCACGTGACTTGACTCAAGCTTATTTAGGCATAGGCATGATGAGATGTCAT
TTCACCATGTGCTGAAGGGTGATGAGGGGCACAGTTGCTTGGGACCACCCACGTGACTTGACTCAAGCTTATTTCTGCTATATCTTTACATGGAT
CTGAAATCCTCTCAAGGGAGCTTGAAATAATTTAGTGGAACATGCTTCATTTACATAGATTATTCAGAATTGGAAATACGGAGGAGGACCTGT
AAAGAAAAGTACCTGTATTACGGAAATTCACACTGTCTAATTCACACTCTAGAGATTATTCATTGCAGAATTGGAATGTGGAATGGAATTCTGGTGTTTG
CCAGCTTCCTTCCTCAAATAGGAGAAATTGACACCTGGCGTGGAATGGAATGCTTTTAGCCCACTTGTACGGAATAGGAGCTGATTAGTAAATGTTGGTAGAGT
ACTGTTAACATCCTTTTCTTCATTTTAGATATGCCTTAGCATTGTGCAGTTCGTGTCCTATCAACTTGACCCCACTTGTGCAGTTCGTGTCTATCAACTTGACCCCCAGCCATCAGTCTGAAAATGTTGGTAT
GATTGAGTTTAAGCTCCCGTGTCGCCCTGTTAGCATTGTGCAGTTTGTCATGTTCTGTTATTACACCGAAGGAGAAAGTAGCATTAATTTACATGATTATCACGAACCAATGACCAACTAAAGG
GTAGTTTTCTGAAGGTGATCAGCAGTGTTCTGTTATTGCCGAAGGAGAAAGTAGCATTAATTTATATGGACTAATAAAGTCATATCAGTAAGGTTCGTTTTTAT
CAGATTGGCCATTTGACTTTACTGGTGAGGTATACAAGAGGTATTGTGTTAATGTACTGTTTTAATTTCAGTTTAATCACTTTAAAGGTAAAAGTGTAAGTGTAAGTACTAAAGACTACAGAAGAGCATTTCTTTGTGAAAGAACAA
TATTTAAGATTGTGCGAGGTTATACAAGAGGTATTGTGTTAATGTACTGTTTTAATTTCAGTTTTGCAGTGTGTGCCGAGTGCCCCAGGCTGGAGTAGCGGATCACGGCTTATT
TGGGCAAGTTACTGACCTACTCTGTTCAAGCGATCCTCCCACCTCAGCTCTGTTTGCCATGTTGCTAGGCTGTGGTCTCAAACTCCTGAGCTCAAGTGATCAGGCGTGATCACGGCTTATT
AAGCCCTGGCTTTTAATAGGCCCTCATAAAGGTACTGTTTTAATTCAGTTTTTCTTGTTTCCTTGTTCAAGGAATACTTTATCACTTTGCCCAGGCTGGAGTAGCGGTGATCACGGCTTATT
CAAACAATATTCTTCTCTTTTTCCTTTTCTTGTTCAAGGCGATCCTCCCACCTCAGCCTCCCAAGTAGCTGGGACTACAGACGTGCGCCACCACGCCCAGCTAATTTTTGTATTTTTAGTAGAGACGGGTTTT
GTACCCCTCCCTGCATGTTCAAGCGATCCTCCCACCTCAGCCTCCCAAGTAGCTGGGACTGCTGTCTCAAACTCCTGACCCTCCCAAAGTACTGA
TTTTTTTTTTTGTAGAGAAGGGGTTTTGCCATGTTGCCAGGCTGGTCTCAAACTCCTGACCTCGTGATCCCGCTGCCTCGGCCTCCCAAAGTACTGA
GATTGTAGGTGTAGTATTAATGATTGTGAGAAAAGAGCTCTTCCAGTCATCTGTTTATCCATTTATTCTCAGCTTGAAATGCTGTTACTCTGTAAAATGAAGGCATATGAAAATTTATGAATTTAGG
TGGGAAGTGTAAATTATAGATTGTGAGAAAAGAGCTCTTCCAGTGAAGACTTTGAATGCTGTTACTCTGTAAAATGCTGTGGTAAATGCTGTGAAATGTGAAGATGAATGCTGTTAAG
AGTTACTGTAGGGTCCAAGGATAAGGTGTAAGAAACTGGCTGGAGTTGAATGTTTCCTGGAGGAGAGCTGAGCAGAGATGAGGCAAACTCAACTAGAATCCCTGGAATTTCTGCCTGAAGAGGAAGAGGACTCGAGATCCCTGGAATTTCTGCCT
CTGTAATTAAGGTGCTGTTGAAAGAAACTGGCTGGTAAGAAAAACTGGCTGGTAGGCAGTTCCTTAGACCATATGCTTAGACCATATCCTTAGACCATATCCTTAGACCACTGTCCGT
TTCTGTCTCAAGATGCATGTCTTTGTCCAGATGACTACCTGTGTCAGATGACTACCTGTGTCAGATGACTACCTGTGTCAGATGACTGAACTGACAGTCCCGT
                                                                                            M D S L D H M L T D P L E L G P
```

SEQUENCE LISTING

```
<160> NUMBER OF SEQ ID NOS: 88

<210> SEQ ID NO 1
<211> LENGTH: 15
<212> TYPE: DNA
<213> ORGANISM: Artificial Sequence
<220> FEATURE:
<223> OTHER INFORMATION: PNA for a region of the human gamma-globin
      promoter (PNA 78)

<400> SEQUENCE: 1
tactctaaga ctatt                                                15

<210> SEQ ID NO 2
<211> LENGTH: 15
<212> TYPE: DNA
<213> ORGANISM: Artificial Sequence
<220> FEATURE:
<223> OTHER INFORMATION: PNA for a region of the human gamma-globin
      promoter (PNA 7)

<400> SEQUENCE: 2
tgtggaactg ctgaa                                                15

<210> SEQ ID NO 3
<211> LENGTH: 16
<212> TYPE: DNA
<213> ORGANISM: Artificial Sequence
<220> FEATURE:
<223> OTHER INFORMATION: PNA for a region of the human gamma-globin
      promoter (PNA 116)

<400> SEQUENCE: 3
ggctattggt caaggc                                               16
```

```
<210> SEQ ID NO 4
<211> LENGTH: 13
<212> TYPE: DNA
<213> ORGANISM: Artificial Sequence
<220> FEATURE:
<223> OTHER INFORMATION: PNA for a region of the human gamma-globin
      promoter (PNA 150)

<400> SEQUENCE: 4
gagtttagcc agg                                                          13

<210> SEQ ID NO 5
<211> LENGTH: 15
<212> TYPE: DNA
<213> ORGANISM: Artificial Sequence
<220> FEATURE:
<223> OTHER INFORMATION: gamma-globin promoter mutated at the PNA target
      region

<400> SEQUENCE: 5
aatagtttta tagta                                                        15

<210> SEQ ID NO 6
<211> LENGTH: 11
<212> TYPE: PRT
<213> ORGANISM: Human immunodeficiency virus type 1

<400> SEQUENCE: 6

Tyr Gly Arg Lys Lys Arg Arg Gln Arg Arg Arg
1               5                   10

<210> SEQ ID NO 7
<211> LENGTH: 13
<212> TYPE: PRT
<213> ORGANISM: Artificial Sequence
<220> FEATURE:
<223> OTHER INFORMATION: TAT peptide variant derived from HIV1

<400> SEQUENCE: 7

Gly Arg Lys Lys Arg Arg Gln Arg Arg Arg Pro Pro Gln
1               5                   10

<210> SEQ ID NO 8
<211> LENGTH: 11
<212> TYPE: PRT
<213> ORGANISM: Artificial Sequence
<220> FEATURE:
<223> OTHER INFORMATION: TAT peptide variant derived from HIV1

<400> SEQUENCE: 8

Tyr Ala Arg Lys Ala Arg Arg Gln Ala Arg Arg
1               5                   10

<210> SEQ ID NO 9
<211> LENGTH: 11
<212> TYPE: PRT
<213> ORGANISM: Artificial Sequence
<220> FEATURE:
<223> OTHER INFORMATION: TAT peptide variant derived from HIV1

<400> SEQUENCE: 9

Tyr Ala Arg Ala Ala Ala Arg Gln Ala Arg Ala
1               5                   10
```

```
<210> SEQ ID NO 10
<211> LENGTH: 11
<212> TYPE: PRT
<213> ORGANISM: Artificial Sequence
<220> FEATURE:
<223> OTHER INFORMATION: TAT peptide variant derived from HIV1

<400> SEQUENCE: 10

Tyr Ala Arg Ala Ala Arg Arg Ala Ala Arg Arg
1               5                   10

<210> SEQ ID NO 11
<211> LENGTH: 11
<212> TYPE: PRT
<213> ORGANISM: Artificial Sequence
<220> FEATURE:
<223> OTHER INFORMATION: TAT peptide variant derived from HIV1

<400> SEQUENCE: 11

Tyr Ala Arg Ala Ala Arg Arg Ala Ala Arg Ala
1               5                   10

<210> SEQ ID NO 12
<211> LENGTH: 7
<212> TYPE: PRT
<213> ORGANISM: Simian virus 40

<400> SEQUENCE: 12

Pro Lys Lys Lys Arg Lys Val
1               5

<210> SEQ ID NO 13
<211> LENGTH: 16
<212> TYPE: PRT
<213> ORGANISM: Artificial Sequence
<220> FEATURE:
<223> OTHER INFORMATION: penetratin peptide derived from drosophila
      melanogaster

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 16
<212> TYPE: PRT
<213> ORGANISM: Artificial Sequence
<220> FEATURE:
<223> OTHER INFORMATION: penetratin peptide derived from drosophila
      melanogaster

<400> SEQUENCE: 14

Lys Lys Trp Lys Met Arg Arg Asn Gln Phe Trp Ile Lys Ile Gln Arg
1               5                   10                  15

<210> SEQ ID NO 15
<211> LENGTH: 16
<212> TYPE: PRT
<213> ORGANISM: Artificial Sequence
<220> FEATURE:
<223> OTHER INFORMATION: penetratin peptide derived from drosophila
      melanogaster

<400> SEQUENCE: 15

Arg Gln Ile Lys Ile Trp Phe Gln Asn Arg Arg Met Lys Trp Lys Lys
1               5                   10                  15
```

```
<210> SEQ ID NO 16
<211> LENGTH: 16
<212> TYPE: PRT
<213> ORGANISM: Artificial Sequence
<220> FEATURE:
<223> OTHER INFORMATION: penetratin peptide derived from drosophila
      melanogaster

<400> SEQUENCE: 16

Arg Gln Ile Lys Ile Trp Phe Pro Asn Arg Arg Met Lys Trp Lys Lys
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: penetratin peptide derived from drosophila
      melanogaster

<400> SEQUENCE: 17

Arg Gln Pro Lys Ile Trp Phe Pro Asn Arg Arg Met Pro Trp Lys Lys
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: penetratin peptide derived from drosophila
      melanogaster

<400> SEQUENCE: 18

Arg Gln Ile Lys Ile Trp Phe Gln Asn Met Arg Arg Lys Trp Lys Lys
1               5                   10                  15

<210> SEQ ID NO 19
<211> LENGTH: 16
<212> TYPE: PRT
<213> ORGANISM: Artificial Sequence
<220> FEATURE:
<223> OTHER INFORMATION: penetratin peptide derived from drosophila
      melanogaster

<400> SEQUENCE: 19

Arg Gln Ile Arg Ile Trp Phe Gln Asn Arg Arg Met Arg Trp Arg Arg
1               5                   10                  15

<210> SEQ ID NO 20
<211> LENGTH: 15
<212> TYPE: PRT
<213> ORGANISM: Artificial Sequence
<220> FEATURE:
<223> OTHER INFORMATION: penetratin peptide derived from drosop
      hila melanogaster

<400> SEQUENCE: 20

Arg Arg Trp Arg Arg Trp Trp Arg Arg Trp Trp Arg Arg Trp Arg
1               5                   10                  15

<210> SEQ ID NO 21
<211> LENGTH: 13
<212> TYPE: PRT
<213> ORGANISM: Homo sapiens

<400> SEQUENCE: 21

Met Ser Arg Arg Lys Gln Ser Lys Pro Arg Gln Ile Leu
1               5                   10
```

```
<210> SEQ ID NO 22
<211> LENGTH: 16
<212> TYPE: PRT
<213> ORGANISM: Drosophila melanogaster

<400> SEQUENCE: 22

Arg Gln Ile Leu Ile Trp Phe Gln Asn Arg Arg Met Lys Trp Lys Lys
1               5                   10                  15

<210> SEQ ID NO 23
<211> LENGTH: 18
<212> TYPE: PRT
<213> ORGANISM: Mus musculus

<400> SEQUENCE: 23

Leu Leu Ile Ile Leu Arg Arg Arg Ile Arg Lys Gln Ala His Ala His
1               5                   10                  15

Ser Lys

<210> SEQ ID NO 24
<211> LENGTH: 18
<212> TYPE: PRT
<213> ORGANISM: Artificial Sequence
<220> FEATURE:
<223> OTHER INFORMATION: model amphipathic peptide

<400> SEQUENCE: 24

Lys Leu Ala Leu Lys Leu Ala Leu Lys Ala Leu Lys Ala Ala Leu Lys
1               5                   10                  15

Leu Ala

<210> SEQ ID NO 25
<211> LENGTH: 21
<212> TYPE: PRT
<213> ORGANISM: Mus musculus

<400> SEQUENCE: 25

Ala Gly Tyr Leu Leu Gly Lys Ile Asn Leu Lys Ala Leu Ala Ala Leu
1               5                   10                  15

Ala Lys Lys Ile Leu
                20

<210> SEQ ID NO 26
<211> LENGTH: 16
<212> TYPE: PRT
<213> ORGANISM: herpes simplex virus

<400> SEQUENCE: 26

Asp Phe Asp Leu Asp Met Leu Gly Asp Phe Asp Leu Asp Met Leu Gly
1               5                   10                  15

<210> SEQ ID NO 27
<211> LENGTH: 14
<212> TYPE: PRT
<213> ORGANISM: Artificial Sequence
<220> FEATURE:
<223> OTHER INFORMATION: ATF-14 domain

<400> SEQUENCE: 27

Cys Gly Ser Asp Ala Leu Asp Asp Phe Asp Leu Asp Met Leu
1               5                   10

<210> SEQ ID NO 28
<211> LENGTH: 20
```

```
<212> TYPE: PRT
<213> ORGANISM: herpes simplex virus

<400> SEQUENCE: 28

Pro Glu Phe Pro Gly Ile Glu Leu Gln Glu Leu Gln Glu Leu Gln Ala
1               5                   10                  15
Leu Leu Gln Gln
            20

<210> SEQ ID NO 29
<211> LENGTH: 20
<212> TYPE: PRT
<213> ORGANISM: Saccharomyces cerevisiae

<400> SEQUENCE: 29

Arg His Gly Glu Lys Trp Phe Leu Asp Asp Phe Thr Asn Asn Gln Met
1               5                   10                  15
Asp Gln Asp Tyr
            20

<210> SEQ ID NO 30
<211> LENGTH: 16
<212> TYPE: PRT
<213> ORGANISM: herpes simplex virus

<400> SEQUENCE: 30

Met Leu Gly Asp Phe Asp Leu Asp Met Leu Gly Asp Phe Asp Leu Asp
1               5                   10                  15

<210> SEQ ID NO 31
<211> LENGTH: 22
<212> TYPE: DNA
<213> ORGANISM: Homo sapiens

<400> SEQUENCE: 31
agccttgaca aggcaaactt ga                                           22

<210> SEQ ID NO 32
<211> LENGTH: 22
<212> TYPE: DNA
<213> ORGANISM: Homo sapiens

<400> SEQUENCE: 32
ccctggcctc actggatact ct                                           22

<210> SEQ ID NO 33
<211> LENGTH: 21
<212> TYPE: DNA
<213> ORGANISM: Homo sapiens

<400> SEQUENCE: 33
accgttttgg caatccattt c                                            21

<210> SEQ ID NO 34
<211> LENGTH: 20
<212> TYPE: DNA
<213> ORGANISM: Homo sapiens

<400> SEQUENCE: 34
tattgcttgc agaataagcc                                              20

<210> SEQ ID NO 35
<211> LENGTH: 22
```

<212> TYPE: DNA
<213> ORGANISM: Homo sapiens

<400> SEQUENCE: 35
gaccgttttg gcaatccatt tc                                            22

<210> SEQ ID NO 36
<211> LENGTH: 20
<212> TYPE: DNA
<213> ORGANISM: Homo sapiens

<400> SEQUENCE: 36
tattgcttgc agaataagcc                                               20

<210> SEQ ID NO 37
<211> LENGTH: 27
<212> TYPE: DNA
<213> ORGANISM: Homo sapiens

<400> SEQUENCE: 37
acacaactgt gttcactagc aacctca                                       27

<210> SEQ ID NO 38
<211> LENGTH: 25
<212> TYPE: DNA
<213> ORGANISM: Homo sapiens

<400> SEQUENCE: 38
ggttgcccat aacagcatca ggagt                                         25

<210> SEQ ID NO 39
<211> LENGTH: 53
<212> TYPE: DNA
<213> ORGANISM: Homo sapiens

<400> SEQUENCE: 39
ccaatagtct tagagtatcc agtgaggcca ggggccggcg gctggctagg gat          53

<210> SEQ ID NO 40
<211> LENGTH: 28
<212> TYPE: DNA
<213> ORGANISM: Homo sapiens

<400> SEQUENCE: 40
ccggttgacc aatagtctta gagtatcc                                      28

<210> SEQ ID NO 41
<211> LENGTH: 235
<212> TYPE: DNA
<213> ORGANISM: Homo sapiens

<400> SEQUENCE: 41
cccttcccca cactatctca atgcaaatat ctgtctgaaa cggttcctgg ctaaactcca    60
cccatgggtt ggccagcctt gccttgacca atagccttga caaggcaaac ttgaccaata   120
gtcttagagt atccagtgag gccaggggcc ggcggctggc tagggatgaa gaataaaagg   180 aagcacccctt cagcagttcc acacactcgc ttctggaacg tctgaggtta tcaat       235

<210> SEQ ID NO 42
<211> LENGTH: 584
<212> TYPE: DNA
<213> ORGANISM: Homo sapiens

<400> SEQUENCE: 42

```
acactcgctt ctggaacgtc tgaggttatc aataagctcc tagtccagac gccatgggtc      60
atttcacaga ggaggacaag gctactatca caagcctgtg gggcaaggtg aatgtggaag     120
atgctggagg agaaaccctg gaaggctcc tggttgtcta cccatggacc cagaggttct      180
ttgacagctt tggcaacctg tcctctgcct ctgccatcat gggcaacccc aaagtcaagg     240
cacatggcaa gaaggtgctg acttccttgg gagatgccac aaagcacctg gatgatctca     300
agggcacctt tgcccagctg agtgaactgc actgtgacaa gctgcatgtg gatcctgaga     360
acttcaagct cctgggaaat gtgctggtga ccgttttggc aatccatttc ggcaaagaat     420
tcaccgctga ggtgcaggct tcctggcaga agatggtgac tgcagtggcc agtgccctgt     480
cctccagata ccactgagct cactgcccat gattcagagc tttcaaggat aggctttatt     540
ctgcaagcaa tacaaataat aaatctattc tgctgagaga tcac                      584
```

<210> SEQ ID NO 43
<211> LENGTH: 147
<212> TYPE: PRT
<213> ORGANISM: Homo sapiens

<400> SEQUENCE: 43

```
Met Gly His Phe Thr Glu Glu Asp Lys Ala Thr Ile Thr Ser Leu Trp
1               5                   10                  15

Gly Lys Val Asn Val Glu Asp Ala Gly Gly Glu Thr Leu Gly Arg Leu
            20                  25                  30

Leu Val Val Tyr Pro Trp Thr Gln Arg Phe Phe Asp Ser Phe Gly Asn
        35                  40                  45

Leu Ser Ser Ala Ser Ala Ile Met Gly Asn Pro Lys Val Lys Ala His
    50                  55                  60

Gly Lys Lys Val Leu Thr Ser Leu Gly Asp Ala Thr Lys His Leu Asp
65                  70                  75                  80

Asp Leu Lys Gly Thr Phe Ala Gln Leu Ser Glu Leu His Cys Asp Lys
                85                  90                  95

Leu His Val Asp Pro Glu Asn Phe Lys Leu Leu Gly Asn Val Leu Val
            100                 105                 110

Thr Val Leu Ala Ile His Phe Gly Lys Glu Phe Thr Pro Glu Val Gln
        115                 120                 125

Ala Ser Trp Gln Lys Met Val Thr Ala Val Ala Ser Ala Leu Ser Ser
    130                 135                 140

Arg Tyr His
145
```

<210> SEQ ID NO 44
<211> LENGTH: 626
<212> TYPE: DNA
<213> ORGANISM: Homo sapiens

<400> SEQUENCE: 44

```
acatttgctt ctgacacaac tgtgttcact agcaacctca acagacacc atggtgcatc       60 tgactcctga ggagaagtct gccgttactg ccctgtgggg caaggtgaac gtggatgaag     120
ttggtggtga ggccctgggc aggctgctgg tgtctaccc ttggacccag aggttctttg      180
agtcctttgg ggatctgtcc actcctgatg ctgttatggg caaccctaag gtgaaggctc     240
atggcaagaa agtgctcggt gcctttagtg atggcctggc tcacctggac aacctcaagg     300
gcacctttgc cacactgagt gagctgcact gtgacaagct gcacgtggat cctgagaact     360
```

```
tcaggctcct gggcaacgtg ctggtctgtg tgctggccca tcactttggc aaagaattca    420
ccccaccagt gcaggctgcc tatcagaaag tggtggctgg tgtggctaat gccctggccc    480
acaagtatca ctaagctcgc tttcttgctg tccaatttct attaaaggtt cctttgttcc    540
ctaagtccaa ctactaaact ggggatatt atgaagggcc ttgagcatct ggattctgcc    600
taataaaaaa catttatttt cattgc                                         626
```

<210> SEQ ID NO 45
<211> LENGTH: 147
<212> TYPE: PRT
<213> ORGANISM: Homo sapiens

<400> SEQUENCE: 45

```
Met Val His Leu Thr Pro Glu Glu Lys Ser Ala Val Thr Ala Leu Trp
1               5                   10                  15

Gly Lys Val Asn Val Asp Glu Val Gly Gly Glu Ala Leu Gly Arg Leu
                20                  25                  30

Leu Val Val Tyr Pro Trp Thr Gln Arg Phe Phe Glu Ser Phe Gly Asp
            35                  40                  45

Leu Ser Thr Pro Asp Ala Val Met Gly Asn Pro Lys Val Lys Ala His
        50                  55                  60

Gly Lys Lys Val Leu Gly Ala Phe Ser Asp Gly Leu Ala His Leu Asp
65                  70                  75                  80

Asn Leu Lys Gly Thr Phe Ala Thr Leu Ser Glu Leu His Cys Asp Lys
                85                  90                  95

Leu His Val Asp Pro Glu Asn Phe Arg Leu Leu Gly Asn Val Leu Val
            100                 105                 110

Cys Val Leu Ala His His Phe Gly Lys Glu Phe Thr Pro Pro Val Gln
        115                 120                 125

Ala Ala Tyr Gln Lys Val Val Ala Gly Val Ala Asn Ala Leu Ala His
    130                 135                 140

Lys Tyr His
145
```

<210> SEQ ID NO 46
<211> LENGTH: 1586
<212> TYPE: DNA
<213> ORGANISM: Homo sapiens

<400> SEQUENCE: 46

```
cacactcgct tctggaacgt ctgaggttat caataagctc ctagtccaga cgccatgggt     60
catttcacag aggaggacaa ggctactatc acaagcctgt ggggcaaggt gaatgtggaa    120
gatgctggag agaaaccct gggaaggtag gctctggtga ccaggacaag ggagggaagg    180
aaggaccctg tgcctggcaa aagtccaggt cgcttctcag gatttgtggc accttctgac    240
tgtcaaactt ttcttgtcaa tctcacaggc tcctggttgt ctaccatgg acccagaggt    300 tctttgacag cttttggcaac ctgtcctctg cctctgccat catgggcaac cccaaagtca    360
aggcacatgg caagaaggtg ctgacttcct tgggagatgc cacaaagcac ctggatgatc    420
tcaagggcac ctttgcccag ctgagtgaac tgcactgtga caagctgcat gtggatcctg    480
agaacttcaa ggtgagtcca ggagatgttt cagccctgtt gcctttagtc tcgaggcaac    540
ttagacaacg gagtattgat ctgagcacag cagggtgtga gctgtttgaa gatactgggg    600
ttgggggtga agaaactgca gaggactaac tgggctgaga cccagtggta atgttttagg    660
```

```
gcctaaggag tgcctctaaa aatctagatg gacaattttg actttgagaa aagagaggtg    720
gaaatgagga aaatgacttt tctttattag attccagtag aaagaacttt catctttccc    780 tcattttgt tgttttaaaa catctatctg gaggcaggac aagtatggtc gttaaaaga     840 tgcaggcaga aggcatatat tggctcagtc aaagtgggga actttggtgg ccaaacatac    900
attgctaagg ctattcctat atcagctgga cacatataaa atgctgctaa tgcttcatta    960
caaacttata tcctttaatt ccagatgggg gcaaagtatg tccaggggtg aggaacaatt   1020
gaaacatttg ggctggagta gattttgaaa gtcagctctg tgtgtgtgtg tgtgtgtgcg   1080
cgcgcgcgtg tgtgtgtgtg tgtcagcgtg tgtttctttt aacgtcttca gcctacaaca   1140
tacagggttc atggtggcaa gaagatagca agatttaaat tatggccagt gactagtgct   1200
tgaaggggaa caactacctg catttaatgg gaaggcaaaa tctcaggctt tgagggaagt   1260
taacataggc ttgattctgg gtggaagctt ggtgtgtagt tatctggagg ccaggctgga   1320
gctctcagct cactatgggt tcatctttat tgtctccttt catctcaaca gctcctggga   1380
aatgtgctgg tgaccgtttt ggcaatccat ttcggcaaag aattcacccc tgaggtgcag   1440
gcttcctggc agaagatggt gactgcagtg ccagtgccc tgtcctccag ataccactga    1500
gctcactgcc catgattcag agctttcaag gataggcttt attctgcaag caatacaaat   1560
aataaatcta ttctgctgag agatca                                        1586
```

<210> SEQ ID NO 47
<211> LENGTH: 12
<212> TYPE: PRT
<213> ORGANISM: Homo sapiens

<400> SEQUENCE: 47

Met Ser Arg Arg Lys Gln Ser Lys Pro Arg Gln Ile
1               5                   10

<210> SEQ ID NO 48
<211> LENGTH: 20
<212> TYPE: DNA
<213> ORGANISM: Homo sapiens

<400> SEQUENCE: 48
agtacaactc catgaccagc                                                 20

<210> SEQ ID NO 49
<211> LENGTH: 19
<212> TYPE: DNA
<213> ORGANISM: Homo sapiens

<400> SEQUENCE: 49
tcacatgtgt gagaggggc                                                  19

<210> SEQ ID NO 50
<211> LENGTH: 19
<212> TYPE: DNA
<213> ORGANISM: Homo sapiens

<400> SEQUENCE: 50
taagcttcca aggccctcc                                                  19

<210> SEQ ID NO 51
<211> LENGTH: 19
<212> TYPE: DNA
<213> ORGANISM: Homo sapiens

<400> SEQUENCE: 51
ctcctccggg ttttgctcc                                                19

<210> SEQ ID NO 52
<211> LENGTH: 20
<212> TYPE: DNA
<213> ORGANISM: Homo sapiens

<400> SEQUENCE: 52
aattacccat ccttcctgcc                                               20

<210> SEQ ID NO 53
<211> LENGTH: 23
<212> TYPE: DNA
<213> ORGANISM: Homo sapiens

<400> SEQUENCE: 53
ttaaaaatgc ctcttcatgt gta                                           23

<210> SEQ ID NO 54
<211> LENGTH: 20
<212> TYPE: DNA
<213> ORGANISM: Homo sapiens

<400> SEQUENCE: 54
tccactcgga aggactatcc                                               20

<210> SEQ ID NO 55
<211> LENGTH: 21
<212> TYPE: DNA
<213> ORGANISM: Homo sapiens

<400> SEQUENCE: 55
ttacgcacaa gagttccgta g                                             21

<210> SEQ ID NO 56
<211> LENGTH: 199
<212> TYPE: DNA
<213> ORGANISM: Homo sapiens

<400> SEQUENCE: 56
cctgcactga ggtcctggag gggcgccagt tgtgtctccc ggttttcccc ttccacagac    60
accattgcca ccaccattag gcaaacatcc ttcgcctcag tttctccccc cacctccctc   120
tcctccaccc atccagggggg cggggccaga ggtcaaggct agtgggtgga ctggggaggg  180 agagagggt tgagtagtc                                                 199

<210> SEQ ID NO 57
<211> LENGTH: 200
<212> TYPE: DNA
<213> ORGANISM: Homo sapiens

<400> SEQUENCE: 57
gctctgggag cctcctcccc ctcctcgcct gcccctcct ccccggcct ccccgcgcg       60 gccggcggcg cgggaggccc cgccccttt catgcaaaac ccggcagcga ggctgggctc    120
gagtggagga gccgccgcgc gctgattggt cgctagaaac ccatttattc cctgacagcc   180
cccgtcacat ggatggttgt                                               200

<210> SEQ ID NO 58
<211> LENGTH: 200

```
<212> TYPE: DNA
<213> ORGANISM: Homo sapiens

<400> SEQUENCE: 58
cccagccccg cccgcgcccc tccttcccct ccccgccccc cacgtgcgcc gagtttgttg      60
atttagctgc catagcaacg atggaaggga gcctcggggg gggcggagag aagaaaggga     120
ggggcggggc atgggagaag gcggaggaaa aggctgtagc gaaggaagtt ataagtaagg     180
aacgcgcgcc ggcggccggc                                                 200

<210> SEQ ID NO 59
<211> LENGTH: 200
<212> TYPE: DNA
<213> ORGANISM: Homo sapiens

<400> SEQUENCE: 59
ttactctgtt tacatcctag agctagagtg ctcggctgcc cggctgagtc tcctccccac      60
cttccccacc ctcccaccc tcccataag cgcccctccc gggttcccaa agcagagggc     120 gtggggaaa agaaaaaaga tcctctctcg ctaatctccg cccaccggcc ctttataatg     180
cgagggtctg gacggctgag                                                 200

<210> SEQ ID NO 60
<211> LENGTH: 200
<212> TYPE: DNA
<213> ORGANISM: Homo sapiens

<400> SEQUENCE: 60
tcaaacctca aggttctgag aagggacacc ccagaggtgt cagagaccgg agttgtgggg      60
gagggccgga gctggagccg gagggaaagg gaggggaaag gagagggagg ggaggggagg     120
gggctgcccg cggggggttg ggtcattgtc ttttagaatt tgggagcctt tgaaaagccg     180
tgggccctcc caccgctatt                                                 200

<210> SEQ ID NO 61
<211> LENGTH: 200
<212> TYPE: DNA
<213> ORGANISM: Homo sapiens

<400> SEQUENCE: 61
agtatttgtt gctgggtttg tcttcaggtt ctgttgctcg gttttctagt tccccaccta      60
gtctgggtta ctctgcagct acttttgcat tacaatggcc ttggtgagac tggtagacgg     120
gattaactga gaattcacaa gggtgggtca gtaggggtg tgcccgccag gaggggtggg     180
tctaaggtga tagagccttc                                                 200

<210> SEQ ID NO 62
<211> LENGTH: 200
<212> TYPE: DNA
<213> ORGANISM: Homo sapiens

<400> SEQUENCE: 62
ccgactccgc acgcctggag cggcaatact gcctgcccta gaaggccagc ggcgagtgct      60
cgccactagg gtcccaggga gggtttggaa aactgatgag ttaagtgagc gaccccaggg     120
gacagagggc gagtcgagag tcggccaatg gctgcggtgg gcggggagaa gacgacgcgg     180
ggatctgcgt gggccgggtc                                                 200

<210> SEQ ID NO 63
```

```
<211> LENGTH: 200
<212> TYPE: DNA
<213> ORGANISM: Homo sapiens

<400> SEQUENCE: 63
tctggggcct ctggaagctc ctaaatcagg tgagacgcgc aagcaggctg gaacctgcat    60
ccccaggccc agccgcgcgc aggcaccctc gccgaccctc cgctctcccg agccgctcca   120
ggacccgccc gctgtggccc cgccccggca ccctccaggc cccgccccgc gctgccccgc   180
cccttccgcc gcgcaggccc                                               200

<210> SEQ ID NO 64
<211> LENGTH: 1200
<212> TYPE: DNA
<213> ORGANISM: Homo sapiens

<400> SEQUENCE: 64
ggctgttgat gcattgaggg atagcgccac acacacattc aataaatttg aggagctgag    60
agggtgactg gccccctgaag gcacagtgcc agaggtctgt ggagaggggg tcaagcacct   120
gggttcctga agaacatgga ggtgtgggag tgattccaga cagctgggat gtgcagagcc   180
tgagagagtc ccagggagcg ggttgggagt tgaaagttgg gtgtggtggc tcacgccttt   240
aatcatgaca ctgggcggca gaggcggag gatttcttga ggacaggaat tcaagaccag   300
cctgggtaac atagcaaggc cccatctcta ctaaaaataa aaaactaac agggcacagt   360
ggtccaagcc tgtagtccca gccacttagg aggctggagc agaaggattg ctttggccca   420
gtagatcgag gctacattga gccatcattg tactccactg cactccagtc tgggcaacaa   480
agtgagaccc tgtcttaaaa aataaaaata aaaaagtttt ctgtggggga cctgcactga   540
ggtcctggag gggcgccagt tgtgtctccc ggttttcccc ttccacagac accattgcca   600
ccaccattag gcaaacatcc ttcgcctcag tttctccccc cacctccctc tcctccaccc   660
atccaggggg cggggccaga ggtcaaggct agtgggtggg actggggagg gagagagggg   720
ttgagtagtc ccttcgcaag ccctcatttc accaggcccc cggcttgggg cgccttcctt   780
ccccatggcg ggacacctgg cttcggattt cgccttctcg cccctccag gtggtggagg   840
tgatgggcca gggggccgg agccgggctg ggttgatcct cggacctggc taagcttcca   900
aggccctcct ggagggccag gaatcgggcc gggggttggg ccaggctctg aggtgtgggg   960
gattccccca tgccccccgc cgtatgagtt ctgtgggggg atggcgtact gtgggcccca  1020
ggttggagtg gggctagtgc cccaaggcgg cttggagacc tctcagcctg agggcgaagc  1080
aggagtcggg gtggagagca actccgatgg ggcctccccg gagccctgca ccgtcacccc  1140
tggtgccgtg aagctggaga aggagaagct ggagcaaaac ccggaggagg caagtgagct  1200

<210> SEQ ID NO 65
<211> LENGTH: 135
<212> TYPE: PRT
<213> ORGANISM: Homo sapiens

<400> SEQUENCE: 65

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
            20                  25                  30

Arg Thr Trp Leu Ser Phe Gln Gly Pro Pro Gly Gly Pro Gly Ile Gly
        35                  40                  45
```

Pro Gly Val Gly Pro Gly Ser Glu Val Trp Gly Ile Pro Pro Cys Pro
    50                  55                  60

Pro Pro Tyr Glu Phe Cys Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
            115                 120                 125

Leu Glu Gln Asn Pro Glu Glu
    130                 135

<210> SEQ ID NO 66
<211> LENGTH: 1100
<212> TYPE: DNA
<213> ORGANISM: Homo sapiens

<400> SEQUENCE: 66
aagagaggag agcggaagag cgcagtacgg gagcggcacc agaggggctg gagttggggg      60
ggagtgctgt ggatgagcgg gagaacaatg acacaccaac tcctgcactg ctgtttcca     120
gaaatacgag ttggacagcc gccctgagcc acccactgtg ccctgcccca ccccgcacc     180
ttagctgctt cccgcgtccc atcctcattt aagtaccctg caccaaaaag taatcaata     240
ttaagtttaa agaaaaaaaa acccacgtag tcttagtgct gtttaccac ttccttcgaa      300
aaggcgtgtg gtgtgacctg ttgctgcgag aggggataca aaggtttctc agtggctggc     360
aggctggctc tgggagcctc ctccccctcc tcgcctgccc cctcctcccc cggcctcccc     420
cgcgcggccg gcggcgcggg aggccccgcc cccttttcatg caaaacccgg cagcgaggct     480
gggctcgagt ggaggagccg ccgcgcgctg attggtcgct agaaacccat ttattccctg     540
acagcccccg tcacatggat ggttgtctat taacttgttc aaaaaagtat caggagttgt     600
caaggcagag aagagagtgt ttgcaaaagg gggaaagtag tttgctgcct ctttaagact     660
aggactgaga gaaagaagag gagagagaaa gaaagggaga gaagtttgag ccccaggctt     720
aagcctttcc aaaaaataat aataacaatc atcggcggcg gcaggatcgg ccagaggagg     780
agggaagcgc ttttttttgat cctgattcca gtttgcctct ctctttttttt ccccaaatt     840
attcttcgcc tgatttttcct cgcggagccc tgcgctcccg acaccccgc ccgcctcccc     900
tcctcctctc cccccgcccg cggccccccc aaagtcccgg ccgggccgag ggtcggcggc     960
cgccggcggg ccgggcccgc gcacagcgcc cgcatgtaca acatgatgga gacggagctg    1020
aagccgccgg gcccgcagca aacttcgggg ggcggcggcg gcaactccac cgcggcggcg    1080
gccggcggca accagaaaaa                                                1100

<210> SEQ ID NO 67
<211> LENGTH: 36
<212> TYPE: PRT
<213> ORGANISM: Homo sapiens

<400> SEQUENCE: 67

Met Tyr Asn Met Met Glu Thr Glu Leu Lys Pro Pro Gly Pro Gln Gln
1               5                   10                  15

Thr Ser Gly Gly Gly Gly Asn Ser Thr Ala Ala Ala Ala Gly Gly
            20                  25                  30

Asn Gln Lys Asn

<210> SEQ ID NO 68
<211> LENGTH: 1000
<212> TYPE: DNA
<213> ORGANISM: Homo sapiens

<400> SEQUENCE: 68

```
cggctccagc ccgccagctg cctggctggc gtcacggccc ggcccagccc cgcccgcgcc    60
cctccttccc ctcccccgcc cccacgtgcg ccgagtttgt tgatttagct gccatagcaa   120
cgatggaagg gagcctcggg gggggcggag agaagaaagg gaggggcggg gcatgggaga   180
aggcggagga aaaggctgta gcgaaggaag ttataagtaa ggaacgcgcg ccggcggccg   240
gcagtttccc gaccagagag aacgaacgtg tctgcgggcg cgcggggagc agaggcggtg   300
gcgggcggcg gcggcaccgg gagccgccga gtgaccctcc ccgcccctc tggcccccca   360
ccctcccacc cgcccgtggc ccgcgcccat ggccgcgcgc gctccacaca actcaccgga   420
gtccgcgcct tgcgccgccg accagttcgc agctccgcgc cacggcagcc agtctcacct   480
ggcggcaccg cccgcccacc gccccggcca cagcccctgc gcccacggca gcactcgagg   540
cgaccgcgac agtggtgggg gacgctgctg agtggaagag agcgcagccc ggccaccgga   600
cctacttact cgccttgctg attgtctatt tttgcgttta caacttttct aagaactttt   660
gtatacaaag gaactttta aaaagacgcg ttccaagtta tatttaatcc aaagaagaag   720
gatctcggcc aatttggggt tttggttttt ggcttcgttt cttctcttcg ttgactttgg   780
ggttcaggtg cccagctgc ttcgggctgc cgaggacctt ctgggccccc acattaatga   840
ggtaggtgag gcgcgcggcg ctgggagcag ggaggggtga ggaccggtgg gacgcgccgg   900
aacgacggcc gaaagccgcc cctgactctc ctgtctccgc tccctgcctt gctcgcaggc   960
agccacctgg cgagtctgac atggctgtca gcgacgcgct                        1000
```

<210> SEQ ID NO 69
<211> LENGTH: 14
<212> TYPE: PRT
<213> ORGANISM: Homo sapiens

<400> SEQUENCE: 69

Gln Pro Pro Gly Glu Ser Asp Met Ala Val Ser Asp Ala Leu
1               5                   10

<210> SEQ ID NO 70
<211> LENGTH: 900
<212> TYPE: DNA
<213> ORGANISM: Homo sapiens

<400> SEQUENCE: 70

```
atgatttata ctcacaggac aaggatgcgg tttgtcaaac agtactgcta cggaggagca    60
gcagagaaag ggagagggtt tgagagggag caaaagaaaa tggtaggcgc gcgtagttaa   120
ttcatgcggc tctcttactc tgtttacatc ctagagctag agtgctcggc tgcccggctg   180
agtctcctcc ccaccttccc caccctcccc accctcccca taagcgcccc tcccgggttc   240
ccaaagcaga gggcgtgggg gaaaagaaaa aagatcctct ctcgctaatc tccgccacc   300
ggcccttat aatgcgaggg tctggacggc tgaggacccc cgagctgtgc tgctcgcggc   360
cgccaccgcc gggccccggc cgtccctggc tcccctcctg cctcgagaag gcagggctt   420
ctcagaggct tggcgggaaa aagaacggag ggagggatcg cgctgagtat aaaagccggt   480
```

```
tttcggggct ttatctaact cgctgtagta attccagcga gaggcagagg gagcgagcgg    540
gcggccggct agggtggaag agccgggcga gcagagctgc gctgcgggcg tcctgggaag    600
ggagatccgg agcgaatagg gggcttcgcc tctggcccag ccctcccgct gatccccag    660 ccagcggtcc gcaacccttg ccgcatccac gaaactttgc ccatagcagc gggcgggcac    720
tttgcactgg aacttacaac acccgagcaa ggacgcgact ctcccgacgc ggggaggcta    780
ttctgcccat tggggacac ttccccgccg ctgccaggac ccgcttctct gaaaggctct    840
ccttgcagct gcttagacgc tggattttt tcgggtagtg gaaaaccagg taagcaccga    900
```

<210> SEQ ID NO 71
<211> LENGTH: 10
<212> TYPE: PRT
<213> ORGANISM: Homo sapiens

<400> SEQUENCE: 71

Met Asp Phe Phe Arg Val Val Glu Asn Gln
1               5                   10

<210> SEQ ID NO 72
<211> LENGTH: 600
<212> TYPE: DNA
<213> ORGANISM: Homo sapiens

<400> SEQUENCE: 72

```
gccaggctca cacctccctc ccccaactct ctggaatgta taattatctg cccgggggggt    60 gggggtggtg tgtgtgtgtg tgtgtgtgtg tgtgtgcagt cacgtggttt                120
taaaactacc ccccccacca ggtccccac ctgtatctgc tttggggacc cctactgagt    180
ccaaagtgca ggatctcaaa ttccggggta ctcaagtctt ctagggcaga cagacccatc    240
tccagttgtg cgtgtgggga ggggtgtca aacctcaagg ttctgagaag ggacacccca    300
gaggtgtcag agaccggagt tgtggggag ggccggagct ggagccggag ggaaaggggag    360 gggaaaggag agggagggga ggggaggggg ctgcccgcgg ggggttgggt cattgtcttt    420
tagaatttgg gagcctttga aaagccgtgg gccctcccac cgctattgtg cgggggaaga    480
tgtagcagct tcttctccga accaacccctt tgccttcgga cttctccggg gccagcagcc    540
gcccgaccag gggcccgggg ccacgggctc agccgacgac catgggctcc gtgtccaacc    600
```

<210> SEQ ID NO 73
<211> LENGTH: 6
<212> TYPE: PRT
<213> ORGANISM: Homo sapiens

<400> SEQUENCE: 73

Met Gly Ser Val Ser Asn
1               5

<210> SEQ ID NO 74
<211> LENGTH: 700
<212> TYPE: DNA
<213> ORGANISM: Homo sapiens

<400> SEQUENCE: 74

```
tacagacacc caccaccatg cgtggctaat ttttgtattt ttagtagaga ggggtttcg     60 ccatgttggc caggctggtt tcaaactcct gacttcaggt gatccgcctg ccacggcctc    120
ccaatttact gggattacag gggtgggcca ccgcgcccgg cctttttctt aattttaaa    180 aatattaaag ttttatccca ttcctgttga accatattcc tgatttaaaa gttggaaacg    240
```

```
tggtgaacct agaagtattt gttgctgggt ttgtcttcag gttctgttgc tcggttttct    300
agttccccac ctagtctggg ttactctgca gctacttttg cattacaatg gccttggtga    360
gactggtaga cgggattaac tgagaattca caagggtggg tcagtagggg gtgtgcccgc    420
caggaggggt gggtctaagg tgatagagcc ttcattataa atctagagac tccaggattt    480
taacgttctg ctggactgag ctggttgcct catgttatta tgcaggcaac tcactttatc    540
ccaatttctt gatactttc cttctggagg tcctatttct ctaacatctt ccagaaaagt     600
cttaaagctg ccttaacctt ttttccagtc cacctcttaa atttttttcct cctcttcctc   660 tatactaaca tgagtgtgga tccagcttgt ccccaaagct                          700

<210> SEQ ID NO 75
<211> LENGTH: 10
<212> TYPE: PRT
<213> ORGANISM: Homo sapiens

<400> SEQUENCE: 75

Met Ser Val Asp Pro Ala Cys Pro Gln Ser
1               5                   10

<210> SEQ ID NO 76
<211> LENGTH: 2000
<212> TYPE: DNA
<213> ORGANISM: Homo sapiens

<400> SEQUENCE: 76
ccaacgctcc cacgtgtcac tgccggggac tcgcgaggcg aagcttccca gcgctcaagg     60
cgctcccgcc tcgtcccag gtatcaggaa cagacaccca ccaggtccac cagcgggtca    120
gacgccgcct tcgggcaggc tgggatcttc gaactgggaa gcggagagta aggggctcga    180
ccccgggacg cgagtccggc cttctggact ccggttcagg gtgtgtgtgc gcgcggaggg    240
gcttatctgg gggccctggg tagcacacgt gttcggtttt tttctccccg actccgcacg    300
cctggagcgg caatactgcc tgccctagaa ggccagcggc gagtgctcgc cactagggtc    360
ccagggaggg tttggaaaac tgatgagtta agtgagcgac cccaggggac agagggcgag    420
tcgagagtcg gccaatggct gcggtgggcg gggagaagac gacgcgggga tctgcgtggg    480
ccgggtcaat tccctaccct cgacctgtcg atgcccgcg gccccgcccg ccctcttaag    540
cctggctcag ccctcagggc ccgcccgaag tctaccgagc ccgagtggcc taccgagccc    600
gagtggcccc gcagcgtcca ggaggcgccc gctccgcgt ggcgctcttg gaggtggtgt    660
cggaggtagg cacgggacag gacgcgcctg gggccegggg cggtggtctt ccagggccgt    720
tggggagggc ggcagcactc gctggcgcag ttcgttttgg atggtcgttc tgccctctcg    780
ggggctttga atcccaagtt gcagatccct gaggtcggag gaggctagga aagggcgcc    840 tttggaggat cgggaggaga cgggccgctg cctgtgtcgt ggctgacctc ttctcctgac    900
cccgtgttct ttaatttctg agtcatgacc ctgcttggtt ttcttattgg gctcattgat    960
ctcaagaccc gccggccctg aaggggcttc attcttcagc ctcggtgaac ttgctgcctg   1020
tctattaaaa cgccatcctt tccggcggt gcggggcgg gaggactggc agtcgccgag    1080
gctcttcgct cccacctggc cagggctcgt ccacgcggct cccgaggggc taccccaggc   1140
cccaatagtc ctggtagaat gattggagtt tccgaggaac ccggggaatg tggcggacgc    1200
tgcccgcgag ggaaaagagg ttcaggcggc gcatcctagg gcagccaaaa gtggcgcgcc    1260
cctcccctgc gggcagtcag gaccgccagg acccgcgggg tcacaccgct gggccagagc   1320
```

```
aggtcgcggg gtccctggac ctgcccgggg gctctgggag cgcgtctcca tctgcgcggt    1380
gcgacccagg gtcctcggct cttccctccc agccgagggc ccaggagcgc ctggagctgt    1440
cgcttgctcc attgccctcc gaccgcctgc gctcggctcc cggcccagcc ccgaggttgg    1500
cagggccccg cggctcccac agaccctacc aacgagtttt gtaggactga aagaaggaa    1560 ggaaagggaa cttcaatggg ttttgcagga accgggttgg gggccgaaag cggagagcgg    1620
gtgtgggaag gcggccgggc ttagggaagg ggtgcttgga gagggaaggg gaaggcaaca    1680
ctaacccgga atttagagta gggcaggatc ccggcagatt tccgtttggg cttttttgt     1740 gtttgcttct attgctgttt tttcgttttg tcttaattgt gggagcgggc tggcgggatc    1800
ggactggggg cgtttatcct gttcccttgg atctggggct ggctggggtg gaggaggctg    1860
gtggggaggc gcgggtcgga ccccgggaag ctcccgcgcg tgtcctcag cggcgcccgc     1920 ttttctgcag agccgccgag cgtgcggtcc cgggatggct ctaccccggc caagtgaggc    1980
cgtgcctcag gacaaggtgt                                                2000

<210> SEQ ID NO 77
<211> LENGTH: 15
<212> TYPE: PRT
<213> ORGANISM: Homo sapiens

<400> SEQUENCE: 77

Met Ala Leu Pro Arg Pro Ser Glu Ala Val Pro Gln Asp Lys Val
1               5                   10                  15

<210> SEQ ID NO 78
<211> LENGTH: 3500
<212> TYPE: DNA
<213> ORGANISM: Homo sapiens

<400> SEQUENCE: 78
aaactactct cttccaggaa gggaagaaca ttagctcggc cggccggctt ctctggtccc      60
atccacacac agaactgagg atggtctctg cgccactgct gggagtacct ggaataagta     120
gtgtgaagcc gtactaagca aaacccagtg aataacagga aaggggcctt catatctaag     180
aagaggaaaa tgatggagtt taactttaaa atgtgatcct tcgatgtgtt tacattcttt     240
ctggacatcg agggcccggg gacgggaagg aggaatgaag gaactcggaa gcacaggctg     300
aggtcgcgtt ctactcatgt cctcaactgt aaaatgggca ctaatagtgc atagctcaca     360
gggctgcagc acaaagacgg tgggtagaaa gtgcttagca tagggcctgg ggcagggtat     420
gctctctgca aacgtcagct aatagacgtg ccttcgctca cgggctatgg aactttgatt     480
cgcggtcagg caaagacagg cactgtctgg ggcctctgga agctcctaaa tcaggtgaga     540
cgcgcaagca ggctggaacc tgcatcccca ggcccagccg cgcgcaggca ccctcgccga     600
ccctccgctc tcccgagccg ctccaggacc cgcccgctgt ggccccgccc cggcaccctc     660 caggcccccgc cccgcgctgc cccgcccctt cgccgcgcgca ggcccagagc gtgcgcgcac    720
ccagactcct tgcgggagcg agtgcgtctg ggagcccgcg gccggagaag ggctgcgggt    780 taggggccg cgcgccgcgg ttcaggtgag gcgggcaag gggcggcgaa agggttgaag      840
tgtctcctgg gagtggaggg agcgggagcg ggcggctggg tccgcgaggt cgctgcccgt    900
gtgggcgtgg ggagcgggag cggggcgtgg ggagcggtgc gacgcgtgag gctggggtt    960 agggttaggc acggcgtggg ggaggggcgg ggccgagccg tgcagttctg aggattggac    1020
ccgggccttg ggccagccgg gctggcaccg gaggggaatt tgctgcagag ttgagggctt    1080
```

```
tggagccggc ggttgctctg gaaggacccg agggtttagc ttctgcgttg gggagggtcc    1140
agcggggaaa gttagaccag gtgctgaaag ccagtgatga gaggccgaga ggccttcgtg    1200
gtctagtgaa gaggttcaga acgcccgaag atctggaaat ccttggcttc cggggtccaa    1260
ctccctggca gctgcctggt tttggtattt tgagattctg ttcagaatag tggcagtgca    1320
aaggttgtca gtggactaga ttaactttag ctagacacgc accgtcactg aagaaacttg    1380
tgagcaagtt gtatagagac ctcctaagag gcaggtagga cactgacttt gcagttgata    1440
gtctgttcta tgccagttct gttaagaagg ttttattctg agcatcaggt tgcttctgca    1500
attttttttt ggtgctattt tgaagttttg ttaaactcac atgctatgtg ctgtctcacc    1560
cgcttcactt atttaggcat aggcatgatg aggatgtcat ttcaccatgt gctgaagggt    1620
gatgaggggg cacagttgct tggggaccac ccacgtgact tgactcaacg cttaagtttc    1680
tgctatatct ttacatggat ctgaaatctc ttcaagggag cttgaaataa tttagtggaa    1740
catgcttcat tttacatata gttattctag aactgttctt tatcattgga gaattttgga    1800
aaagaaaagt acctgtatta cgtaattcac actgtcactc atctagagat tattcattgc    1860
aggattccag aattggaaat aacgggaggg aggacctggt ccagcttccc ttcctcaaat    1920
aaggaaattg acacctggcg tggtaagatt tgtggaatgt ggtgtttgtg gaatgtggaa    1980
tatggaattc tggtgttttg actgttaaca tccttttttc ttttcatttt agtatgcttt    2040
ttagcccact ttgtaggaat aggagctgga aaggatggat ttagtaaatg ttggtagagt    2100
gattgagttt aagctccctg tggtcctgtt agcattgtgc agtcctgtgc tatcaacttg    2160
acccctaatc ccagccatca gtctgaaaat gttgtggtat gtagttttct gaaggtgatc    2220
agcagtgttc tgttattaca cgaaggagaa aagtagcatt aatttacatg attatacgga    2280
tcaaatggac caactaaagg cagattggcc attgacttta ctggtggtta tggtcaggtg    2340
tgtggaacct caggaatttta tatggactaa taaagtcata tcagtaaggt tcgttttat    2400 tatttaaatg ttgcgaggtt atacaagagg tattgtgtgt agcattaagc acatgggttt    2460
gcaggcaggt agacctgagt ttcagtactg cctctggggt tgggcaagtt actgacctac    2520
tctgattttc agttttaatt ccgatgtaat aacccatgac cttactttgc acagttgtag    2580
gaattaaatg agatatgtga aaggcctggc ttttaatagg ccctcataaa gtgactgtta    2640
gcatttgcat tttactagtg tatgttgatt ttcagcaaat tttcttttgt gaaagaacaa    2700
caaacaatat tctttctctt tttcctttcc tttttttttt ttttgagac agggtctctg    2760 ttgcccaggc tggagtgcag tagcgtgatc acggcttatt gtaccctctg catctcgtgt    2820
tcaagcgatc ctcccacctc agccttctga gtagctggga ctacaggcgt gcgccaccac    2880
gcctggctga tttttttttt ttttttttt tgtagagaag gggttttgcc atgttcgcta    2940
ggctggtctc aaactcatgg attcaagggg actgcccgcc tggacctccc aaagtactga    3000
gattgtaggt gtgagttact gcacccagcc aacaacaaag aattaattgc taaaaaacag    3060
ttgttacaga aattacattg tgggagagtg attattggtc tgggaagtgt aaattataga    3120
ttgtgatctg tttatcattt attctcagtc tcattttact catctgtaaa atgaaggcat    3180
atgaaattta tgaatttagg agttactgta ggagcattct gagaaaagag ctcttccagg    3240
taagacttga aaattccagt gggaatgctg tggtgaaagg gagggaggag agctgtttag    3300
ctgtaattag ggtgcaagga taaggtgtaa gaactggctg gaggttgaat gttttcctgg    3360
aggagtgtta gcatcaacta gatccctgga atttctgcct ttctgtctca agatgcatgt    3420
```

```
ctttgtccag agtacctgtg gagaagaaac aatggattcc ttagaccata tgctgacaga    3480
tcctctggaa cttggtccgt                                                3500
```

<210> SEQ ID NO 79
<211> LENGTH: 16
<212> TYPE: PRT
<213> ORGANISM: Homo sapiens

<400> SEQUENCE: 79

Met Asp Ser Leu Asp His Met Leu Thr Asp Pro Leu Glu Leu Gly Pro
1               5                   10                  15

<210> SEQ ID NO 80
<211> LENGTH: 15
<212> TYPE: DNA
<213> ORGANISM: Artificial Sequence
<220> FEATURE:
<223> OTHER INFORMATION: PRalpha PNA Sequence

<400> SEQUENCE: 80

```
ctttctcctc cctct                                                     15
```

<210> SEQ ID NO 81
<211> LENGTH: 17
<212> TYPE: DNA
<213> ORGANISM: Artificial Sequence
<220> FEATURE:
<223> OTHER INFORMATION: PRalpha PNA Sequence

<400> SEQUENCE: 81

```
cctttccct cctccct                                                    17
```

<210> SEQ ID NO 82
<211> LENGTH: 19
<212> TYPE: DNA
<213> ORGANISM: Artificial Sequence
<220> FEATURE:
<223> OTHER INFORMATION: PRbeta PNA Sequence

<400> SEQUENCE: 82

```
tgtctggcca gtccacagc                                                 19
```

<210> SEQ ID NO 83
<211> LENGTH: 13
<212> TYPE: DNA
<213> ORGANISM: Artificial Sequence
<220> FEATURE:
<223> OTHER INFORMATION: PRbeta PNA Sequence

<400> SEQUENCE: 83

```
tgtctggcca gtc                                                       13
```

<210> SEQ ID NO 84
<211> LENGTH: 15
<212> TYPE: DNA
<213> ORGANISM: Artificial Sequence
<220> FEATURE:
<223> OTHER INFORMATION: PRbeta PNA Sequence

<400> SEQUENCE: 84

```
tgtctggcca gtcca                                                     15
```

<210> SEQ ID NO 85
<211> LENGTH: 15
<212> TYPE: DNA

```
<213> ORGANISM: Artificial Sequence
<220> FEATURE:
<223> OTHER INFORMATION: IL-2Ralpha PNA Sequence

<400> SEQUENCE: 85
tctccctctc cttttt                                                       15

<210> SEQ ID NO 86
<211> LENGTH: 13
<212> TYPE: DNA
<213> ORGANISM: Artificial Sequence
<220> FEATURE:
<223> OTHER INFORMATION: IL-2Ralpha PNA Sequence

<400> SEQUENCE: 86
ttttcctctc cct                                                          13

<210> SEQ ID NO 87
<211> LENGTH: 10
<212> TYPE: DNA
<213> ORGANISM: Artificial Sequence
<220> FEATURE:
<223> OTHER INFORMATION: lacUV5 PNA Sequence

<400> SEQUENCE: 87
tttttctttt                                                              10

<210> SEQ ID NO 88
<211> LENGTH: 15
<212> TYPE: DNA
<213> ORGANISM: Artificial Sequence
<220> FEATURE:
<223> OTHER INFORMATION: MUT PNA78 Sequence

<400> SEQUENCE: 88
tactataaaa ctatt                                                        15
```

US 8,927,502 B2

EMBEDDED CHIMERIC PEPTIDE NUCLEIC ACIDS AND USES THEREOF

This application is a continuation-in-part of PCT International Application No. PCT/US2011/025128, filed Feb. 16, 2011, claiming priority of U.S. Provisional Application No. 61/338,316, filed Feb. 16, 2010; and a continuation-in-part of PCT International Application No. PCT/US2011/062423, filed Nov. 29, 2011, claiming priority of U.S. Provisional Application No. 61/534,240, filed Sep. 13, 2011, and 61/417,760, filed Nov. 29, 2010, the contents of each of which are hereby incorporated by reference in their entireties.

The research leading to the present invention was supported, in part, by grant number HL073437, awarded by the National Institutes of Health. Accordingly, the U.S. Government has certain rights in this invention.

This application incorporates-by-reference nucleotide and/or amino acid sequences which are present in the file named "140102_0028_82577_SEQUENCELISTING_REB.TXT", which is 39.1 kilobytes in size, and which was created Jan. 2, 2014 in the IBM-PC machine format, having an operating system compatibility with MS-Windows, which is contained in the text file filed Jan. 2, 2014 as part of this application.

Throughout this application, certain publications are referenced in brackets. The disclosures of these publications in their entireties are hereby incorporated by reference into this application in order to describe more fully the state of the art to which this invention relates.

TECHNICAL FIELD

The present invention provides novel embedded chimeric peptide nucleic acid molecules (ecPNAs) comprising (i) a PNA targeting a promoter region of a gene, wherein said PNA is conjugated to (ii) at least one cell and/or nuclear entry sequence and (iii) a transcription activation or repression domain. The ecPNAs of the invention can modulate gene expression and are useful for treating diseases requiring changes in transcription and for induction of inducible pluripotent stem (iPS) cells.

BACKGROUND OF INVENTION

Detection of DNA sequences such as DNA sequences within genes has been used for various purposes including research and disease diagnosis. Compounds useful for detecting DNA sequences include DNA and RNA oligonucleotide probes, typically labeled with some detectable marker such as a radioisotope, a fluorescent dye, or an immunogenic peptide. Nevertheless, there is a continuing need for compounds which can be employed for such purposes. The compounds of the present invention fulfill this need.

Certain of the compounds of this invention may also be used to regulate transcription and expression of genes including genes the regulated expression of which is implicated in, or can be useful in, the treatment or amelioration of disease.

Correct regulation of gene expression is required for fundamental processes in differentiation and development. [See Davidson, E. H., Gene Activity in Early Development, Edn. Third. (Academic Press, Inc., Orlando; 1986)]. In a number of cases, the transcriptional onset and decline of a series of closely related genes are tightly and sequentially controlled, a process that is critical for attaining the correct genotypic readout and proper phenotypic effect. [See Bresnick, E. H., Martowicz, M. L., Pal, S. & Johnson, K. D., Developmental control via GATA factor interplay at chromatin domains. J Cell Physiol 205, 1-9 (2005), Stamatoyannopoulos, G., The molecular basis of blood diseases, Edn. 3rd. (W.B. Saunders, Philadelphia; 2001); and Krumlauf, R, Noordermeer D., de Laat W., Joining the loops: β-globin gene regulation. IUMMB Life 60, 824-833 (2008); and Krumlauf, R., Hox genes in vertebrate development. Cell 78, 191-201 (1994).]A particularly well-studied example of this process is the developmental control of the hemoglobin proteins, particularly those encoded by the genes within the β-like globin locus. [See Stamatoyannopoulos, G., The molecular basis of blood diseases, Edn. 3rd. (W.B. Saunders, Philadelphia; 2001); Krumlauf, R., Hox genes in vertebrate development. Cell 78, 191-201 (1994); and Schechter, A. N., Hemoglobin research and the origins of molecular medicine. Blood 112, 3927-3938 (2008).] These variants exhibit a sequential erythroid-restricted pattern of expression during development, beginning with the yolk sac ε-globin, switching to the fetal γ-globin, and ending with the adult β-globin.

The critical requirement for correct regulation of this locus is demonstrated by the moderate to life-threatening clinical manifestations exhibited by the β-thalassemias. β-thalassemia is primarily caused by mutations in the β-globin gene that lead to reduced or complete loss of β-globin expression. Along with other hemoglobinopathies (such as sickle cell disease), they give rise to the most common single gene genetic disorder worldwide. [See Weatherall, D. J., in The Molecular Bases of Blood Diseases. (eds. G. Stamatoyannopoulos, A. W. Nienhuis, P. W. Majerus & H. Varmus) 207-205 (W.B. Saunders Co., Philadelphia; 1994).] Pharmacological reactivation of the silent fetal (γ) globin chain provides a therapeutic benefit to these patients by compensating for absent adult β-globin chains (in β-thalassemia) or by interfering with the polymerization of mutant hemoglobins (in sickle cell disease); however, these are not always free from complications. [See Weatherall D. J., in The Molecular Bases of Blood Diseases. (eds. G. Stamatoyannopoulos, A. W. Nienhuis, P. W. Majerus & H. Varmus) 157-256 (W. B. Saunders Co., Philadelphia; 1994); and Atweh, G. F. & Schechter, A. N., Pharmacologic induction of fetal hemoglobin: raising the therapeutic bar in sickle cell disease. Curr Opin Hematol 8, 123-130 (2001).] As a result, there remain compelling reasons to search for novel approaches and reagents that achieve reactivation with low toxicity and high penetrance.

Regulation of gene expression is also of particular importance for the generation of induced pluripotent stem (iPS) cells. iPS cells are pluripotent stem cells expressing many of the genetic and phenotypic characteristics of embryonic stem (ES) cells. iPS cells have the same gross morphology as ES cells, proliferative properties, form teratomas after transplantation into nude mice, and have the ability to differentiate along all 3 germ layers in vitro. Their responses to key factors such as retinoic acid and leukemia inhibitory factor (LIF) are also the same as those observed for ES cells [Okita et al, Generation of germline-competent induced pluripotent stem cells. Nature 448: 313-317 (2007)]. Generation of iPS cells is useful for both in vitro study of stem cells (e.g., factors controlling stem cell differentiation) and for the application of iPS cells for the treatment of disease. For example, the ability to reprogram cells from human blood would be useful for the generation of patient-specific stem cells for treatment of diseases in which the disease-causing somatic mutations are restricted to cells of the hematopoietic lineage.

Currently, methods for generating iPS cells from somatic cells are limited, and novel methods are needed. iPS cells have the potential to revolutionize medicine, as they can theoretically generate any differentiated tissue from the selfsame individual and thus avoid tissue rejection and other complications. An original protocol for generating iPS cells established iPS cells from murine and human fibroblasts by introducing four specific transcription factors, SOX2, OCT4, KLF4, and c-MYC, into the cells by viral transduction. [See, Lowry, W. E., et al. Generation of human induced pluripotent stem cells from dermal fibroblasts. Proc. Natl. Acad. Sci. USA 105, 2883-2888 (2008); Maherali, N., et al. Directly reprogrammed fibroblasts show global epigenetic remodeling and widespread tissue contribution. Cell Stem Cell; 1, 55-70 (2007); Park, et al. Reprogramming of human somatic cells to pluripotency with defined factors. Nature 451, 141-146 (2008); Takahashi, K., and Yamanaka, S. Induction of Pluripotent Stem cells from Mouse Embryonic and Adult Fibroblast Cultures by Defined Factors. Cell, 126, 663-676 (2006); Takahashi, K. et al. Induction of Pluripotent Stem Cells from Adult Human Fibroblasts by Defined Factors. Cell 131, 861-872 (2007); Yu, J. et al. Induced pluripotent stem cell lines derived from human somatic cells. Science; 318, 1917-1920 (2007); Stadtfeld and Hochedlinger, Induced pluripotency: history, mechanisms, and applications. Genes Dev; 24:2239-2263 (2010); and Hochedlinger and Plath, Epigenetic reprogramming and induced pluripotency. 136; 509-523 (2009).]

Recently, iPS cells were generated from CD34+ mobilized human peripheral blood cells using retroviral transduction of OCT4, SOX2, KLF4, and c-MYC [see, Loh, Y. et al. Generation of induced pluripotent stem cells from human blood. Blood; 113(22):5476-5479 (2009)], and from CD133+ human cord blood (CB) cells [see, Giorgetti, A. et al. Generation of induced pluripotent stem cells from human cord blood using OCT4 and SOX2. Cell Stem Cell; 5:353-357 (2009)]. iPS cells were generated from CD133+ CB cells by retroviral transduction of CB cells with OCT4 and SOX2. CB cells are considered an alternative to bone marrow (BM) as a source of hematopoietic stem cells for transplantation. CB cells can be collected without any risk for the donor, are young cells expected to carry minimal somatic mutations, and possess the immunological immaturity of newborn cells [see, Rocha et al., et al. Transplants of Umbilical-Cord Blood or Bone Marrow from Unrelated Donors in Adults with Acute Leukemia. N. Engl. J. Med. 351, 2276-2285 (2004)]. These properties allow for less stringent criteria for HLA-donor-recipient selection, which represents a decisive benefit for transplantation and has resulted in more than 400,000 immunologically characterized CB units being currently available worldwide through a network of CB banks [see, Gluckman, E., and Rocha, V. Cord blood transplantation: state of the art. Haematologica; 94, 451-454 (2009)].

These approaches brought closer the possibility of using patient-specific cells in cell-based therapy. At least three limitations of those methods, however, were immediately recognizable: (i) the genes were transduced virally; (ii) at least one of the factors, c-Myc, is a known oncogene; and (iii) the process was inefficient. In particular, in the above described studies, retroviral transduction was used to introduce the genes required for iPS cell generation. The use of viruses to deliver the reprogramming factors entails permanent genetic alterations that render the cells inappropriate for many in vitro and in vivo applications. Retroviral gene transduction is associated with a number of limitations (low efficiency), and potential danger for use in human therapy, including the risk of production of replication competent virus, which can infect humans [reviewed in Kurian, K. M. et al. (2000) J Clin Pathol: Mol Pathol; 53:173-176; Stadtfeld and Hochedlinger (2010) Genes Dev; 24:2239-2263].

Thus, what is needed in the art are novel, efficient ways for inducing a selected target gene or genes in a cell without the use of retroviral transduction and without genetically perturbing the recipient cell.

Peptide nucleic acids (PNAs) are oligonucleotide analogues in which the phosphodiester backbone of DNA is replaced by an achiral uncharged polyamide backbone. [See Nielsen, P. E., Egholm, M., Berg, R. H. & Buchardt, O., Sequence-selective recognition of DNA by strand displacement with a thymine-substituted polyamide. Science 254, 1497-1500 (1991).] They are true DNA mimics, as they form Watson-Crick bonds with DNA and RNA, but are of higher thermal stability than natural duplexes due to the lack of electrostatic repulsion. [See Kaihatsu, K., Janowski, B. A. & Corey, D. R., Recognition of chromosomal DNA by PNAs. Chem. Biol 11, 749-758 (2004).] They are also resistant to proteases and nucleases, and thus afford a significantly greater biological stability in culture and in vivo. [See Pooga, M., Land, T., Bartfai, T. & Langel, U., PNA oligomers as tools for specific modulation of gene expression. Biomol Eng 17, 183-192 (2001).] A unique aspect of PNAs is that amino acids can be covalently added to the peptide backbone at either end of the sequence of bases. The PNA/DNA interaction may occur through triple helical (Hoogsteen) base paring (PNA/DNA/PNA) or via a single strand invasion. [See Kaihatsu, K., Janowski, B. A. & Corey, D. R., Recognition of chromosomal DNA by PNAs. Chem. Biol 11, 749-758 (2004); and Zhang, X., Ishihara, T. & Corey, D. R., Strand invasion by mixed base PNAs and a PNA-peptide chimera. Nucleic Acids Res 28, 3332-3338 (2000).] In a single strand invasion, PNA, which can be of mixed sequence design, hybridizes with one strand of DNA through Watson-Crick base pairing and simply replaces the other strand of the double helix.

PNA molecules are thus promising candidates for clinical use as agents to modulate gene expression. For the most part, PNAs have been used as an antigene agent because they have the capacity for down-regulating gene expression in cultured cells and in animals. [See Nielsen, P. E., Peptide nucleic acids as antibacterial agents via the antisense principle. Expert Opin Investig Drugs 10, 331-341 (2001); Cutrona, G. et al., Effects in live cells of a c-myc anti-gene PNA linked to a nuclear localization signal. Nat Biotechnol 18, 300-303 (2000); Janowski, B. A. et al. Inhibiting transcription of chromosomal DNA with antigene peptide nucleic acids. Nat Chem Biol 1, 210-215 (2005); Hu, J. et al., Allele-specific silencing of mutant huntingtin and ataxin-3 genes by targeting expanded CAG repeats in mRNAs. Nat Biotechnol 27, 478-484 (2009); and Nielsen, P. E., PNA Technology. Mol Biotechnol 26, 233-248 (2004).]

PNA molecules have also been used as probes for targeted nucleic acid binding, and to follow the subcellular trafficking of plasmid DNA. Additionally, conjugation of markers such as fluorophores to PNA molecules has been described for these purposes. [See also Zhilina et al., Peptide Nucleic Acid Conjugates: Synthesis, Properties and Applications. Current Topics in Medicinal Chemistry 4:1119-1131 (2005)]. PNA molecules have also been utilized for single base pair mutation analysis by PNA directed PCR clamping. [See also Orum et al., Single base pair mutation analysis by PNA directed PCR clamping. Nucleic Acids Research 21(23):5332-5336 (1993)] However, there is a need for improved PNA structures capable of efficiently detecting the presence of DNA within the nucleus of cells.

PNAs have been modified to maximize cellular/nuclear entry in order to increase the efficiency for in vivo applications. [See Cutrona, G. et al., Effects in live cells of a c-myc anti-gene PNA linked to a nuclear localization signal. Nat Biotechnol 18, 300-303 (2000); Nielsen, P. E., Addressing the challenges of cellular delivery and bioavailability of peptide nucleic acids (PNA). Q Rev Biophys 38, 345-350 (2005); and Braun, K. et al., A biological transporter for the delivery of peptide nucleic acids (PNAs) to the nuclear compartment of living cells. J Mol Biol 318, 237-243 (2002).] However, currently there is no established PNA conjugated system that combines these varied modifications and has been demonstrated to stably and efficiently enter, target, and transcriptionally activate an endogenous chromosomal locus in living cells.

Thus, there remains a great need in the art for novel, efficient and non-toxic compounds which can affect gene expression. Such compounds would be particularly useful in treatment of β-globin disorders, which can be treated by upregulating γ-globin transcription in bone marrow cells, and for the generation of iPS cells, for example by the induction of genes such as OCT4, SOX2, c-MYC, and/or KLF4.

SUMMARY OF THE INVENTION

The present invention addresses these and other needs by providing novel embedded chimeric peptide nucleic acid (ecPNA) molecules.

The present invention relates to an ecPNA having the general structure:

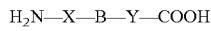

and uses thereof, wherein X is A or C and Y is A or C with the proviso that when X is A, Y is C, and when X is C, Y is A; wherein A represents an oligopeptide structure, the sequence of which comprises a sequence which renders the ecPNA able to enter the nucleus of a cell; wherein B represents a peptide nucleic acid (PNA) structure at least 12 nucleotides in length, the sequence of which is capable of hybridizing with a DNA within the nucleus of the cell, which DNA is within a promoter region of a gene; wherein C represents an oligopeptide structure; and wherein each — represents a chemical linkage between the structures at each side thereof, which may be the same as or different from each other such linkage.

The present invention also relates to an ecPNA having the general structure:

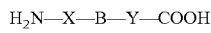

and uses thereof, wherein X is D or C and Y is D or C with the proviso that when X is D, Y is C, and when X is C, Y is D; wherein D represents a compound which renders the ecPNA able to bind to a receptor on a cell; wherein B represents a peptide nucleic acid (PNA) structure at least 12 nucleotides in length, the sequence of which is capable of hybridizing with a DNA within the nucleus of the cell, which DNA is within a promoter region of a gene; wherein C represents an oligopeptide structure; and wherein each — represents a chemical linkage between the structures at each side thereof, which may be the same as or different from each other such linkage.

Aspects of the present invention provide a method for generating an inducible pluripotent stem (iPS) cell from a source cell comprising administering to the source cell an effective amount for inducing the iPS cell of at least one of the ecPNA molecules of the invention, wherein the ecPNA molecule upregulates transcription of a target gene selected from the group consisting of OCT4, SOX2, c-MYC, KLF4, LIN28, NANOG, PRDM14, and NFRKB. In certain embodiments, the source cell is selected from the group consisting of a CD34+ peripheral blood cell, a CD34+ bone marrow cell, a CD133+ cord blood cell, a neural cell and a fibroblast.

In some embodiments, the ecPNA molecule for generating iPS cell comprises a PNA molecule having a nucleic acid sequence that is complementary to a sequence comprised in the 200 base pair (bp) region upstream of the transcription start site of the target gene. In some embodiments, the PNA molecule is about 12 to about 15 nucleotides (nt) in length.

In yet other embodiments, the method for generating an iPS cell comprises administering at least two ecPNA molecules according to the present invention.

In certain of the above embodiments for methods for generating an iPS cell, one of the two ecPNA molecules upregulates transcription of OCT4 gene. In yet other embodiments, one of the two ecPNA molecules upregulates transcription of SOX2 gene. In still other embodiments, one of the two ecPNA molecules upregulates transcription of OCT4 gene and the other of the two ecPNA molecules upregulates transcription of SOX2 gene.

In certain of the above embodiments, the source cell is a human cell.

In some of the above embodiments, the method for generating an iPS cell further comprises conjoint administration of a second agent selected from the group consisting of hydroxyurea, a short chain fatty acid (SCFA) inducer, 5-azacytidine, and a histone deacetylase inhibitor. In certain embodiments, the short chain fatty acid (SCFA) inducer is butyrate. In other embodiments, the histone deacetylase inhibitor is suberoylanilide hydroxamic acid (SAHA).

The invention is described in detail below, with reference to the accompanying figures and by way of non-limiting examples.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 depicts in vitro target binding specificity of four PNAs designed to interact with the human γ-globin promoter.

FIG. 2 depicts cellular and nuclear localization of PNA78 and its derivatives. All PNA molecules contained a biotin tag at their 5'-end and were visualized with streptavidin-FITC.

FIG. 3 depicts in vivo target binding of PNA78/TAT in K562 cells. Specifically, FIG. 3(b), right panel, depicts quantitative chromatin association analysis of K562 cells after exposure to WT PNA78/TAT or MUT PNA78/TAT. 'No PNA' and 'TAT alone' served as controls. The results of quantitative analysis of the γ-globin promoter DNA in the precipitated material is shown.

FIG. 4 depicts in vivo transcriptional activity of chimeric PNA78 derivatives. In FIG. 4(a), a transient assay was performed in K562 cells that had been transfected with plasmid containing the γ-globin promoter (−299~+36) upstream of the luciferase reporter (shown below) followed by exposure to PNA78/TAT, PNA78/NLS, TAT alone, or buffer. Activity values were normalized to a cotransfected Renilla control. In FIG. 4(b), K562 cells were transiently transfected with a luciferase reporter containing either wild type (wt) γ-globin promoter sequence or one that was mutated at the PNA target region (mut) (AATAGTTTTATAGTA; SEQ ID NO: 5), followed by exposure to PNA78/TAT or buffer. Values were normalized to a cotransfected Renilla control.

FIG. 5 shows that PNA78 conjugated to a minimal activation domain reactivates dormant γ globin expression in vivo in mouse adult bone marrow cells (MBC) containing the human βYAC. Cells were treated with each of four modified PNA78 molecules (PNA78/TAT, VP2/PNA78/TAT, Bio-ATF/PNA78/TAT, ATF-Bio/PNA78/TAT), 'TAT alone', or buffer ('no PNA') and analyzed by confocal microscopy (a) or by quantitative RT-PCR (b) 16 hours after PNA treatment. FIG. 5(a) depicts a confocal image of MBC-βYAC showing nuclear-entering efficiency.

FIGS. 7-10 show the nucleic acid and amino acid sequences of human OCT4 (FIG. 7) (SEQ ID NO: 64 and SEQ ID NO: 65), SOX2 (FIG. 8) (SEQ ID NO: 66 and SEQ ID NO: 67), KLF4 (FIG. 9) (SEQ ID NO: 68 and SEQ ID NO: 69), and c-MYC (FIG. 10) (SEQ ID NO: 70 and SEQ ID NO: 71). The bolded, underlined nucleic acid residues are the 200 bp region upstream of the transcription start site. This 200 bp region is the region targeted by the ecPNA molecules of the invention. The start codon, ATG is underlined, bolded and italicized and the transcription start site is italicized.

FIG. 11 shows the analysis of human peripheral blood CD34+ cells at different time points after induction of erythroid differentiation by erythropoietin (Epo).

FIG. 12 shows the analysis of human peripheral blood CD34+ cells during the SCF/Epo phase of culture.

FIG. 13 is an analysis of the effect of PNA78 conjugated to a minimal activation domain on activating γ globin expression in differentiating adult human peripheral blood (H-PB) CD34+ cells.

FIG. 14(a) shows forward scatter ("FSC") and side scatter ("SSC") profiles of the indicated cells. FIG. 14(b) shows the CD34 and CD36 expression profiles of the cells and FIG. 14(c) shows the CD36 and CD235a expression profiles of the indicated cells.

FIGS. 15-18 show the nucleic acid and amino acid sequences of human LIN28 (FIG. 15) (SEQ ID NO: 72 and SEQ ID NO 73), NANOG (FIG. 16) (SEQ ID NO: 74 and SEQ ID NO: 75), PRDM14 (FIG. 17) (SEQ ID NO: 76 and SEQ ID NO: 77) and NFRKB (FIG. 18) (SEQ ID NO: 78 and SEQ ID NO: 79). The bolded, underlined nucleic acid residues are the 200 bp region upstream of the transcription start site. This 200 bp region is the region targeted by the ecPNA molecules of the invention. The start codon ATG is underlined, bolded and italicized and the transcription start site is italicized.

DETAILED DESCRIPTION OF THE INVENTION

Figure 1A:
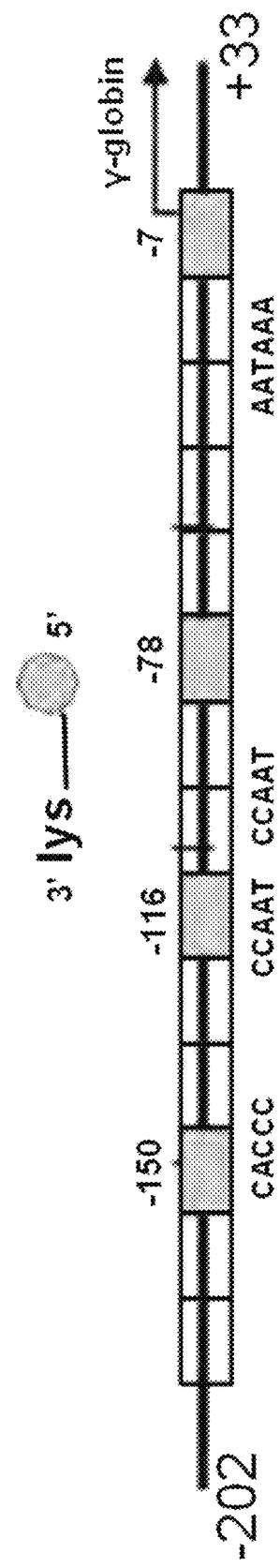
In FIG. 1(a), PNA150 (SEQ ID NO: 4), PNA116 (SEQ ID NO: 3), PNA78 (SEQ ID NO: 1), and PNA7 (SEQ ID NO: 2) were designed to target the proximal promoter region (−202 to +33) of the human fetal γ-globin gene at specific sites indicated by the filled in boxes. The relative location of known promoter elements within this region is also indicated. Orientation of the PNA molecule relative to the promoter sequence is shown above, with a lys at its 3'-end and a biotin molecule (circle) attached at the 5'-end.

The present invention relates to an ecPNA having the general structure:

and uses thereof, wherein X is A or C and Y is A or C with the proviso that when X is A, Y is C, and when X is C, Y is A; wherein A represents an oligopeptide structure, the sequence of which comprises a sequence which renders the ecPNA able to enter the nucleus of a cell; wherein B represents a peptide nucleic acid (PNA) structure at least 12 nucleotides in length, the sequence of which is capable of hybridizing with a DNA within the nucleus of the cell, which DNA is within a promoter region of a gene; wherein C represents an oligopeptide structure; and wherein each — represents a chemical linkage between the structures at each side thereof, which may be the same as or different from each other such linkage.

In some embodiments, X is A and Y is C. In other embodiments, X is C and Y is A.

The present invention also relates to an ecPNA having the general structure:

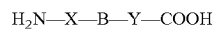

and uses thereof, wherein X is D or C and Y is D or C with the proviso that when X is D, Y is C, and when X is C, Y is D; wherein D represents a compound which renders the ecPNA able to bind to a receptor on a cell; wherein B represents a peptide nucleic acid (PNA) structure at least 12 nucleotides in length, the sequence of which is capable of hybridizing with a DNA within the nucleus of the cell, which DNA is within a promoter region of a gene; wherein C represents an oligopeptide structure; and wherein each — represents a chemical linkage between the structures at each side thereof, which may be the same as or different from each other such linkage.

In some embodiments, X is D and Y is C. In other embodiments, X is C and Y is D.

In some embodiments, D comprises a polypeptide sequence that binds to a receptor on a cell.

In some embodiments, D binds to the erythropoietin (Epo) receptor. In some embodiments, D is an analogue of Epo. In some embodiments D is an Epo mimetic peptide.

In some embodiments, the gene is a gene, the regulation of the transcription and expression of which is desired.

In certain embodiments, the oligopeptide structure C is detectable when the ecPNA is bound to the DNA.

In some embodiments, the sequence of C comprises a sequence which renders the ecPNA able to regulate the transcription and expression of the gene.

In certain embodiments, each — may be a chemical bond or a chemical linker.

In some embodiments, at least one — is a chemical bond.

In certain embodiments, the chemical bond is a covalent bond, an amide bond, or a peptide bond.

In some embodiments, at least one — is a chemical linker.

In some embodiments of the invention, the chemical linker comprises an amino acid, biotin, an ether (O), a stable polyether (OO), AEEA (2-aminoethoxy-2-ethoxyacetic acid), or a cleavable disulfide linkage.

In some embodiments of the invention, the sequence of C renders the ecPNA able to regulate the transcription and expression of the gene by activating transcription of the gene.

In some embodiments of the invention, the sequence of C renders the ecPNA able to regulate the transcription and expression of the gene by upregulating transcription of the gene.

In some embodiments, the sequence of C renders the ecPNA able to regulate the transcription and expression of the gene by downregulating the transcription of the gene.

In some embodiments, the sequence of C renders the ecPNA able to regulate the transcription and expression of the gene by repressing transcription of the gene.

In some embodiments of the invention, A comprises a sequence selected from the group consisting of the following sequences: YGRKKRRQRRR (SEQ ID NO: 6), GRKKRRQRRRPPQ (SEQ ID NO: 7), YARKARRQARR (SEQ ID NO: 8), YARAAARQARA (SEQ ID NO: 9), YARAARRAARR (SEQ ID NO: 10), YARAARRAARA (SEQ ID NO: 11), PKKKRKV (SEQ ID NO: 12), RQIKIWFQNRRMKWKK (SEQ ID NO: 13), KKWKMRRNQF-WIKIQR (SEQ ID NO: 14), RQIKIWFQNRRMKWKK (SEQ ID NO: 15), RQIKIWFPNRRMKWKK (SEQ ID NO: 16), RQPKIWFPNRRMPWKK (SEQ ID NO: 17), RQIKI- WFQNMRRKWKK (SEQ ID NO: 18), RQIRIWFQNRRM-RWRR (SEQ ID NO: 19), RRWRRWWRRWWRRWR (SEQ ID NO: 20), RQILIWFQNRRMKWKK (SEQ ID NO: 22), LLIILRRRIRKQAHAHSK (SEQ ID NO: 23), KLA-LKLALKALKAALKLA (SEQ ID NO: 24), and AGYLLGKINLKALAALAKKIL (SEQ ID NO: 25).

In certain embodiments of the invention, C comprises a sequence selected from the group consisting of the following sequences: DFDLDMLGDFDLDMLG (SEQ ID NO: 26), MLGDFDLDMLGDFDLD (SEQ ID NO: 30), CGSDALD-DFDLDML (SEQ ID NO: 27), PEF-PGIELQELQELQALLQQ (SEQ ID NO: 28), and RHGEK-WFLDDFTNNQMDQDY (SEQ ID NO: 29).

In some embodiments, C comprises a sequence selected from the group consisting of the sequence of an engrailed repression domain, the sequence of the HID (HDAC interaction domain) of the Sin3A protein, and MSRRKQSKPRQI (SEQ ID NO: 47).

In some embodiments of the invention there is a chemical linker between A and B or between B and C and the chemical linker is selected from the group consisting of a stable polyether, AEEA (2-aminoethoxy-2-ethoxyacetic acid), and a cleavable disulfide linkage.

In certain embodiments of the invention, the gene is a γ-globin gene.

In some embodiments, the PNA structure comprises the sequence TACTCTAAGACTATT (PNA78: SEQ ID NO: 1).

In some embodiments, the ecPNA has the structure $H_2N$-CGSDALDDFDLDML-Biotin-O-B-O-YGRKKRRQRRR ((SEQ ID NO: 27)-Biotin-O-B-O-(SEQ ID NO: 6)).

In other embodiments, the ecPNA has the structure $H_2N$-CGSDALDDFDLDML-Biotin-O-TACTCTAAGACTATT-O-YGRKKRRQRRR ((SEQ ID NO: 27)-Biotin-O-(SEQ ID NO: 1)-O-(SEQ ID NO: 6)).

In certain embodiments, the ecPNA has the structure Biotin-OO-DFDLDMLGDFDLDMLG-O-TACTCTAA-GACTATT-O-YGRKKRRQRRR (Biotin-OO-(SEQ ID NO: 26)-O-(SEQ ID NO: 1)-O-(SEQ ID NO: 6)).

In some embodiments, at least one amino acid is in the form of a D-isomer.

A composition comprising the any ecPNA disclosed herein and a carrier is also included as an embodiment of the present invention.

Certain embodiments include methods of detecting the presence of a DNA within the nucleus of a cell which comprises contacting the cell with the ecPNA of claim 1 under conditions such that the ecPNA enters the cell and the PNA structure B hybridizes to the DNA to form a hybridization product, and then detecting the resulting hybridization product.

Embodiments of the invention include methods for upregulating transcription of a γ-globin gene in a mammalian bone marrow cell comprising contacting the cell with an ecPNA of the invention comprised of a sequence that is capable of upregulating or activating the transcription of a gene.

In some embodiments, the mammalian bone marrow cell is an adult erythroid cell.

Embodiments of the invention include methods for treating a β-globin disorder in a mammal comprising administering to said mammal a therapeutically effective amount of any ecPNA disclosed herein.

In some embodiments of the invention, the β-globin disorder is sickle cell anemia or β-thalassemia.

Some embodiments further comprise administering to an animal a second agent selected from the group consisting of hydroxyurea, a short chain fatty acid (SCFA) inducer, 5-azacytidine, and a histone deacetylase inhibitor.

In some embodiments of the invention, the short chain fatty acid (SCFA) inducer is butyrate.

In some embodiments of the invention, the histone deacetylase inhibitor is suberoylanilide hydroxamic acid (SAHA).

In some embodiments of the invention, B is from 12 to 15 nucleotides in length.

Certain embodiments of the present invention are based on the demonstration herein that peptide nucleic acid (PNA) molecules can be used to effectively modulate specific gene expression by conjugating them to two peptide sequences: (1) a cell and/or nuclear entry sequence and (2) a transcription activation or repression domain. The embedded chimeric peptide nucleic acid (ecPNA) molecules of the present invention are designed to bind to a specific DNA sequence in a chromosome, thereby providing increased specificity. The presence of cell and/or nuclear entry sequence facilitates greater efficiency of ecPNA cell and/or nuclear entry. Rather than relying on a triplex structure to passively lead to transcriptional increase, as described in the prior art, the ecPNAs of the present invention include a transcriptional activation domain which directly activates transcription of a target gene. Furthermore, the novel ecPNAs of the present invention can include a transcriptional repression domain, which directly represses transcription of a target gene, a function not provided by the triplex structures of the prior art.

As demonstrated in the Examples section, below, two specific ecPNA constructs of the invention ATF-Bio/PNA78/TAT and VP2/PNA78/TAT produced therapeutically significant increases (7-fold and 2-fold, respectively) in γ-globin gene expression in mouse bone marrow cells engineered to carry a yeast artificial chromosome that contains the complete human β-like globin locus (6-YAC). Thus, the ecPNA molecules of the invention can be used for the treatment of diseases, e.g., diseases or disorders associated with β-globin defects.

Further, in certain embodiments of the invention, the ecPNA molecules can be used to activate or repress gene expression (transcription) for the induction of inducible pluripotent stem (iPS) cells. In a specific embodiment, ecPNA molecules are used to induce transcription of OCT4 or SOX2 or both OCT4 and SOX2 in primary human CD34+ blood cells, bone marrow cells, neural cells and/or cord blood (CB) cells as a means to generate iPS cells. In other embodiments, transcription of other genes, such as, but not limited to, c-MYC, KLF4, LIN28 and/or NANOG can also be activated using ecPNA molecules of the invention. In certain embodiments, expression of any gene or combination of genes that is suitable for the induction of iPS cells is activated using a combination of different ecPNA molecules (i.e., ecPNA molecules having different target genes) of the invention. In certain embodiments, an ecPNA molecule of the invention represses the expression (transcription) of a gene, e.g., a gene associated with differentiated cells, for the induction of iPS cells. In certain embodiments, a combination of ecPNA molecules is administered to a cell to induce iPS cells, wherein at least one of the ecPNA molecules in the combination activates gene expression and at least one of the ecPNA molecules represses gene expression, wherein the combination is suitable for the induction of iPS cells. The specific combination of genes to be activated or repressed will depend on the cell type and source.

In certain embodiments, and without limitation, the invention provides the advantage that neither viral vectors nor oncogenes are introduced, thereby providing a method with increased efficacy and safety compared to other methods. Specifically, there is no transduction or transfection protocol involved, as the ecPNA molecules of the invention, while not intending to be bound by one particular theory or mechanism, are thought to enter the cell and/or nucleus by macropinocytosis. Mammalian cells take up ecPNA molecules efficiently (50-95% after four hours of incubation). In addition, effects on gene expression can be seen within 24 hours. As a result, the ecPNA molecules of the invention provide a useful and efficient alternative to the present vectors and protocols being used to generate iPS cells.

While not intending to be bound by a specific mechanism or theory, the PNAs within ecPNAs of the present invention are believed to function via a single strand invasion by hybridizing with one strand of DNA of the target promoter sequence through Watson-Crick base pairing and replacing the other strand of the double helix. This way the PNAs of the present invention avoid the limitations that follow from a triplex-forming design of the PNAs of the prior art (e.g., requirement for homopurine in the target sequence and requirement for the use of base analogues, which limits the number of potential DNA binding sites).

By providing the novel ecPNA molecules, the present invention provides a sequence-specific and efficient (i.e., low-toxic) gene-activating/repressing tool which can be used in vitro, ex vivo or in vivo to repress the expression of harmful genes (e.g., oncogenes), or to upregulate the expression of useful genes (e.g., tumor suppressor genes or iPS cell genes), or to reactivate the expression of normally repressed genes (e.g., fetal-specific genes in adult cells, e.g., embryonic and/or stem cell genes). The ecPNAs of the present invention can thus be used to treat various diseases treatable by transcriptional modulation, which include, among others, various cancers and hemoglobin disorders, as well as to generate iPS cells. For example, diseases treatable by the molecules of the present invention include, but are not limited to, β-thalassemia (Cooley's anemia), sickle cell disease, chronic myelogenous leukemia (CML) and other myeloproliferative diseases, and acute myeloid leukemia.

In other embodiments, the iPS cells generated using the ecPNA molecules can be used to generate cellular models of diseases associated with somatic gene mutations in, e.g., the bone marrow compartment or stromal compartment. For example, iPS cells generated using the present ecPNA molecules can be used to model acquired blood diseases and blood disorders such as myelodysplastic syndromes, paroxysmal nocturnal hemoglobinuria, and others for which animal models are not available or difficult to create. In addition, iPS cells carrying, e.g., a leukemia-specific cytogenetic translocation can be used to analyze how cancer stem cells develop.

In other embodiments, the iPS cell generated according to the methods described herein can be used to treat a disease or condition in a subject. For example, iPS cells can be differentiated toward a desired cell lineage or type and administered to a patient in need of such treatment. As an example, and without limitation, a patient with spinal cord injury can be administered neural cells, e.g., to the site of spinal cord injury, that were differentiated from iPS cells in vitro (e.g., from a cell line) or ex vivo (e.g. from cells obtained from the patient or from a donor).

In other embodiments, iPS cells generated according to the methods described herein are administered to the patient without being differentiated (i.e., they are administered as iPS cells).

In certain embodiments, iPS cells are preferentially induced from a patient's own somatic cells (e.g., bone marrow or peripheral blood cells, or any other suitable cell type). While not intending to be bound by theory or mechanism, such methods provide the added advantage of providing therapies that are less prone to immune rejection than, for example, therapies using embryonic stem cells, because the cells used in the therapies described herein can be derived entirely from a patient's own cells.

DEFINITIONS

The term "upregulate transcription" and is used to mean enhance transcription and expression of a gene, the expression of which occurs, but at levels less than desired. The term "activate expression" is used to mean activate a gene which otherwise being transcribed and expressed. As specified herein, the use of the ecPNAs of the present invention leads to at least about 2-fold increase of transcription, more preferably at least about 5-fold increase of transcription, and most preferably at least about 7-fold increase of transcription of a gene as measured by any suitable assay (e.g., quantitative mRNA analyses [e.g., qPCR or Northern blot analysis], and/or quantitative protein analyses [e.g., Western blot or immunofluorescence analysis]).

Similarly, the term "downregulate transcription" is used interchangeably to mean reduce the transcription and expression of a gene, the expression of which occurs at levels greater than desired. The term "repress transcription" is used to mean eliminate transcription and expression of a gene, the expression of which results in an undesired effect. As specified herein, the use of the ecPNAs of the present invention leads to at least about 2-fold decrease of transcription, more preferably at least about 5-fold decrease of transcription, and most preferably at least about 7-fold decrease of transcription of a gene as measured by any suitable assay (e.g., quantitative mRNA analyses [e.g., qPCR or Northern blot analysis], and/or quantitative protein analyses [e.g., Western blot or immunofluorescence analysis]).

As used herein, the term "detecting the presence" means marking the presence of a DNA with an oligopeptide of a compound of the invention in any way which may be detected. In certain embodiments of the invention, an oligopeptide of a compound of the invention may be detected through the use of an antibody.

As used herein, the term "target gene" means the gene for which the transcription is to be activated, upregulated, downregulated, or repressed by a compound of the present invention.

Within the meaning of the present invention, the term "co-administration" is used to refer to administration of an ecPNA and a second agent simultaneously in one composition, or simultaneously in different compositions, or sequentially within a certain time period.

As used herein, the term "inducible pluripotent stem (iPS) cell" refers to a type of pluripotent stem cell artificially derived from a non-pluripotent cell, typically an adult somatic cell, by inducing a "forced" expression of specific genes. iPS cells can also be derived by the repression of certain genes (e.g., genes associated with differentiated cells) in lieu of or in addition to by activating the expression of specific genes. The term, "induce/inducing an iPS cell", as used herein, means that a cell having the characteristics of an iPS cell (e.g., is a pluripotent stem cell) is generated. In certain embodiments, iPS cells are induced by forcing or activating the expression of SOX2 and OCT4, and optionally, KLF4 and/or cMYC, although induced expression and/or repression of other genes suitable for the induction of iPS cells are also possible. iPS cells can be identified based on the expression of one or more pluripotency markers, such as, but not limited to OCT4, SOX2, TRA-1-81, TRA-1-60, SSEA3, SSEA4, CRIPTO, REX1 and NANOG genes and/or proteins.

A "source cell", as the term is used herein, refers to a cell that can be used to obtain an iPS cell according to the methods described herein. For example, and without limitation, a human CD34+ peripheral blood cell is one source cell that can be used to induce an iPS cell, e.g., by the forced expression of OCT4 and/or SOX2.

The term "about" means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In the context of the present invention insofar as it relates to any of the disease conditions recited herein, the terms "treat", "treatment", and the like mean to relieve or alleviate at least one symptom associated with such condition, or to slow or reverse the progression of such condition. For example, in relation to β-globin disorders, the symptoms include anemia, tissue hypoxia, organ dysfunction, abnormal hematocrit values, ineffective erythropoiesis, abnormal reticulocyte count, abnormal iron load, splenomegaly, hepatomegaly, impaired peripheral blood flow, dyspnea, increased hemolysis, jaundice, anemic crises and pain such as angina pectoris, etc. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent, delay or treat, or all, as appropriate, development or continuance or aggravation of a disease in a subject.

As used herein the term "therapeutically effective" applied to dose or amount refers to that quantity of a compound or pharmaceutical composition that is sufficient to result in a desired activity upon administration to an animal in need thereof. Within the context of the present invention, the term "therapeutically effective" refers to that quantity of a compound or pharmaceutical composition that is sufficient to reduce or eliminate at least one symptom of a disease or disorder (e.g., a cancer or a β-globin disorder). Note that when a combination of active ingredients is administered the effective amount of the combination may or may not include amounts of each ingredient that would have been effective if administered individually.

The phrase "pharmaceutically acceptable", as used in connection with compositions of the invention, refers to molecular entities and other ingredients of such compositions that are physiologically tolerable and do not typically produce untoward reactions when administered to a mammal (e.g., a human). Preferably, as used herein, the term "pharmaceutically acceptable" means approved by a regulatory agency of the Federal or a state government or listed in the U.S. Pharmacopeia or other generally recognized pharmacopeia for use in mammals, and more particularly in humans.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B.

In accordance with the present invention, there may be employed conventional molecular biology, microbiology, and recombinant DNA techniques within the skill of the art. [See, e.g., Sambrook, Fritsch and Maniatis, Molecular Cloning: A Laboratory Manual, 2nd ed., Cold Spring Harbor Laboratory Press, Cold Spring Harbor, N.Y., 1989 (herein "Sambrook et al., 1989"); DNA Cloning: A Practical Approach, Volumes I and II (Glover ed. 1985); Oligonucleotide Synthesis (Gait ed. 1984); Nucleic Acid Hybridization (Hames and Higgins eds. 1985); Transcription And Translation (Hames and Higgins eds. 1984); Animal Cell Culture (Freshney ed. 1986); Immobilized Cells And Enzymes (IRL Press, 1986); B. Perbal, A Practical Guide To Molecular Cloning (1984); Ausubel et al. eds., Current Protocols in Molecular Biology, John Wiley and Sons, Inc. 1994; among others.]

Embedded Chimeric Peptide Nucleic Acid Molecules of the Invention

In a most general aspect, the present invention provides an isolated embedded chimeric peptide nucleic acid (ecPNA) molecule comprising (i) a PNA targeting a promoter region of a gene, wherein said PNA is conjugated to (ii) at least one cell or nuclear entry sequence and (iii) a transcription activation domain.

In a further general aspect, the present invention provides an ecPNA molecule comprising (i) a PNA targeting a promoter region of a gene, wherein said PNA is conjugated to (ii) at least one cell or nuclear entry sequence and (iii) a transcription repression domain.

In a further general aspect, the present invention provides an ecPNA molecule comprising (i) a PNA targeting a promoter region of a gene, wherein said PNA is conjugated to (ii) at least one compound which renders the ecPNA able to bind a receptor on a cell and (iii) a transcription repression domain.

In one specific aspect, the invention provides an ecPNA molecule comprising (i) a PNA targeting a promoter region of a γ-globin gene, wherein said PNA is conjugated to (ii) at least one cell or nuclear entry sequence and (iii) a transcription activation domain.

In yet another embodiment, the invention provides an ecPNA consisting essentially of (i) a PNA targeting a promoter region of a γ-globin gene, wherein said PNA is conjugated to (ii) at least one cell or nuclear entry sequence and (iii) a transcription activation domain.

In yet another embodiment, the invention provides an ecPNA molecule consisting essentially of (i) a PNA targeting a promoter region of a SOX2 gene, wherein said PNA is conjugated to (ii) at least one cell or nuclear entry sequence and (iii) a transcription activation domain.

In another embodiment, the invention provides an ecPNA molecule consisting essentially of (i) a PNA targeting a promoter region of an OCT4 gene, wherein said PNA is conjugated to (ii) at least one cell or nuclear entry sequence and (iii) a transcription activation domain.

In still another embodiment, the invention provides an ecPNA molecule consisting essentially of (i) a PNA targeting a promoter region of a KLF4 gene, wherein said PNA is conjugated to (ii) at least one cell or nuclear entry sequence and (iii) a transcription activation domain.

In yet another embodiment, the invention provides an ecPNA molecule consisting essentially of (i) a PNA targeting a promoter region of any one or more genes selected from c-MYC, LIN28, NANOG, PRDM14, and NFRKB, wherein said PNA is conjugated to (ii) at least one cell or nuclear entry sequence and (iii) a transcription activation domain.

Any PNA sequence which corresponds to a sequence comprised in the promoter sequence of a target gene can be used within the ecPNA molecules of the invention. In preferred embodiments, the PNA sequences are complementary to a sequence within the 200 base pair (bp) region that is upstream of the transcription start site of a target gene, as shown, e.g., in FIGS. 7-10 and 15-18. While not intending to be bound by theory, this 200 bp region is important for transcriptional regulation of gene expression.

In other embodiments, the PNA sequence is complementary to a sequence within the 400, 350, 300, or 250 base pair (bp) region that is upstream of the transcription start site of a target gene. In some embodiments, the PNA sequence can comprise a nucleic acid sequence that is complementary to a sequence that is downstream of the transcription start site of a target gene.

In certain embodiments, the PNA sequence can comprise one or more nucleic acid substitutions. For example, a nucleic acid residue can be substituted, e.g., with a different nucleic acid, for example, and without limitation, inosine, pseduoisocytosine, 2-thiouracil, and/or diaminopurine. PNA sequences containing such substitutions preferably although not necessarily retain similar activity (i.e., ability to activate or repress transcription of a target gene), compared to the PNA molecule without the one or nucleic acid substitutions. In certain embodiments, a PNA molecule comprises a sequence that is at least 70%, 75%, 80%, 85%, 90%, or 95% identical to a sequence that is complementary to a sequence within the 200 base pair (bp) region that is upstream of the transcription start site of a target gene.

Thus, in certain embodiments, a PNA sequence that targets human OCT4 will have a nucleic acid sequence of about 12 nucleotides (nt) to about 15 nt that is complementary to a sequence comprised in the following nucleic acid sequence:

```
                                                  (SEQ ID NO: 56)
CCTGCACTGAGGTCCTGGAGGGGCGCCAGTTGTGTCTCCCGGTTTTCCCCTTCCACAGACACCATTG
CCACCACCATTAGGCAAACATCCTTCGCCTCAGTTTCTCCCCCCACCTCCCTCTCCTCCACCCATC
CAGGGGGCGGGGCCAGAGGTCAAGGCTAGTGGGTGGACTGGGGAGGGAGAGAGGGGTTGAGTAGTC
(FIG. 7).
```

In certain embodiments, a PNA sequence that targets human SOX2 will have a nucleic acid sequence of about 12 nt to about 15 nt that is complementary to a sequence comprised in the following nucleic acid sequence:

```
                                                  (SEQ ID NO: 57)
GCTCTGGGAGCCTCCT
CCCCCTCCTCGCCTGCCCCCTCCTCCCCCGGCCTCCCCCGCGCGGCCGGCGGCGCGGGAG
GCCCCGCCCCCTTTCATGCAAAACCCGGCAGCGAGGCTGGGCTCGAGTGGAGGAGCCGC
CGCGCGCTGATTGGTCGCTAGAAACCCATTTATTCCCTGACAGCCCCCGTCACATGGATG
GTTGT (FIG. 8).
```

In certain embodiments, a PNA sequence that targets human KLF4 will have a nucleic acid sequence of about 12 nt to about 15 nt that is complementary to a sequence comprised in the following nucleic acid sequence:

```
                                                  (SEQ ID NO: 58)
CCCAGCCCCGCCCGCGCC
CCTCCTTCCCCTCCCCCGCCCCCACGTGCGCCGAGTTTGTTGATTTAGCTGCCATAGCAACGAT
GGAAGGGAGCCTCGGGGGGGGCGGAGAGAAGAAAGGGAGGGGCGGGGCATGGGAGAAGGCG
GAGGAAAAGGCTGTAGCGAAGGAAGTTATAAGTAAGGAACGCGCGCCGGCGGCCGGC (FIG. 9).
```

In certain embodiments, a PNA sequence that targets human c-MYC will have a nucleic acid sequence of about 12 nt to about 15 nt that is complementary to a sequence comprised in the following nucleic acid sequence:

```
                                                  (SEQ ID NO: 59)
TTACTCT
GTTTACATCCTAGAGCTAGAGTGCTCGGCTGCCCGGCTGAGTCTCCTCCCCACCTTCCCC
ACCCTCCCCACCCTCCCCATAAGCGCCCCTCCCGGGTTCCCAAAGCAGAGGGCGTGGGGG
AAAAGAAAAAAGATCCTCTCTCGCTAATCTCCGCCCACCGGCCCTTTATAATGCGAGGG
TCTGGACGGCTGAG (FIG. 10).
```

In certain embodiments, a PNA sequence that targets human LIN28 will have a nucleic acid sequence of about 12 nt to about 15 nt that is complementary to a sequence comprised in the following nucleic acid sequence:

```
                                                  (SEQ ID NO: 60)
TCAAA
CCTCAAGGTTCTGAGAAGGGACACCCCAGAGGTGTCAGAGACCGGAGTTGTGGGGGAGG
GCCGGAGCTGGAGCCGGAGGGAAAGGGAGGGGAAAGGAGAGGGAGGGGAGGGGAGGG
```

-continued
```
GGCTGCCCGCGGGGGGTTGGGTCATTGTCTTTTAGAATTTGGGAGCCTTTGAAAAGCCG
TGGGCCCTCCCACCGCTATT (FIG. 15).
```

In certain embodiments, a PNA sequence that targets human NANOG will have a nucleic acid sequence of about 12 nt to about 15 nt that is complementary to a sequence comprised in the following nucleic acid sequence:

```
                                                    (SEQ ID NO: 61)
CCGACTCCGCACGCCTGGAGCGGCAATACTGCCTGCCCTAGAAGGCCAGCGGCGAGTGCTCG
CCACTAGGGTCCCAGGGAGGGTTTCCAAAACTGATGAGTTAAGTGAGCGACCCCAGGGGACA
GAGGGCGAGTCGAGAGTCGGCCAATGGCTGCGGTGGGCGGGGAGAAGACGACGCGGGGATCT
GCGTGGGCCGGGTC
(FIG. 16).
```

In certain embodiments, a PNA sequence that targets human PRDM14 will have a nucleic acid sequence of about 12 nt to about 15 nt that is complementary to a sequence comprised in the following nucleic acid sequence:

```
                                                    (SEQ ID NO: 62)
AGTATTTGTTGCTGGGTTTGTCTTCAGGTTCTGTTGCTCGGTTTTCTAGTTCCCCACCTAGTCTG
GGTTACTCTGCAGCTACTTTTGCATTACAATGGCCTTGGTGAGACTGGTAGACGGGATTAACTG
AGAATTCACAAGGGTGGGTCAGTAGGGGGTGTGCCCGCCAGGAGGGGTGGGTCTAAGGTGAT
AGAGCCTTC (FIG. 17).
```

In certain embodiments, a PNA sequence that targets human NFRKB will have a nucleic acid sequence of about 12 nt to about 15 nt that is complementary to a sequence comprised in the following nucleic acid sequence:

```
                                                    (SEQ ID NO: 63)
TCTGGGGCCTCTGGAAGCTCCTAAATCAGGTGAGACGCGCAAGCAGGCTGGAACCTGCA
TCCCCAGGCCCAGCCGCGCGCAGGCACCCTCGCCGACCCTCCGCTCTCCCGAGCCGCTCC
AGGACCCGCCCGCTGTGGCCCCGCCCCGGCACCCTCCAGGCCCCGCCCCGCGCTGCCCCG
CCCCTTCCGCCGCGCAGGCCC (FIG. 18).
```

In some embodiments the PNA structure is from 12 nt to 15 nt in length, however, shorter or longer sequences may be possible. In certain embodiments, the PNA structure will be between 12 and 30 nucleotides in length, e.g. between 12 and 25 nucleotides, often between 12 and 30 nucleotides in length.

In some embodiments, the PNA of the ecPNA molecule comprises the sequence TACTCTAAGACTATT (PNA78) (SEQ ID NO: 1).

The sequence of the PNA structure may be capable of hybridizing with a DNA within the nucleus of a cell. In some embodiments, the sequence of the PNA structure will be may be complementary to a sequence within the promoter region of a gene. Non-limiting examples of gene promoters with respect to which complementary PNA sequences have been described are listed in Table 1. The references describing these PNAs are also cited in Table 1 and are hereby incorporated by reference into the present disclosure. In additional embodiments, the sequence of the PNA structure may be complementary to a sequence within a promoter region bound by a polymerase, such as T7, SP6, or T3 RNA polymerase. [See also Hamilton et al., Specific and nonspecific inhibition of transcription by DNA, PNA, and phosphorothioate promoter analog duplexes. Bioorganic & Medicinal Chemistry Letters 6(23):2897-2900 (1996); and Larsen and Nielsen, Transcription-mediated binding of peptide nucleic acid (PNA) to double-stranded DNA: sequence-specific suicide transcription. Nucleic Acids Res. 24:458-463 (1996).]

TABLE 1

Genes with Promoters for which PNAs have been Targeted

| Gene | PNA Sequence(s) | Reference |
|---|---|---|
| BCL2 | GGGCGGAGG<br>GCCAGGGA | Onyshchenko et al., Stabilization of G-quadruplex in BCL2 promotoer region in double-stranded DNA by invading short PNAs. Nucleic Acids Res.37(22):7570-80 (2009) |
| PRα | CTTTCTCCTCCCTCT<br>(SEQ ID NO: 80)<br>CCTCCCCC<br>CTTTTCCCTCCTCCCT<br>(SEQ ID NO: 81) | Kaihatsu, K., Janowski, B.A. & Corey, D.R., Recognition of chromosomal DNA by PNAs. Chem Biol 11, 749-758 (2004) |

TABLE 1-continued

Genes with Promoters for which PNAs have been Targeted

| Gene | PNA Sequence(s) | Reference |
|---|---|---|
| PRβ | TGTCTGGCCAGTCCACAGC (SEQ ID NO: 82) TGTCTGGCCAGTC (SEQ ID NO: 83) TGTCTGGCCAGTCCA (SEQ ID NO: 84) | Hu and Corey, Inhibiting gene expression with peptide nucleic acid (PNA)—peptide conjugates that target chromosomal DNA. Biochemistry 46(25):7581-9 (2007) |
| HER-2 | CTCCTCCTC CCTCCTCT | Stankova et al., Mechanism of PNA transport to the nuclear compartment. Ann NY Acad Sci. 1082:27-30 (2006) |
| IL-2Rα | TCTCCCTCTCCTTTT (SEQ ID NO: 85) TTTTCCTCTCCCT (SEQ ID NO: 86) | Vickers et al., Inhibition of NF-B specific transcriptional activation by PNA strand invasion. Nucleic Acids Research 23(15):2003-8 (1995) |
| lacUV5 | TTTTTCTTTT (SEQ ID NO: 87) | Mollegaard et al., Peptide nucleic acid. DNA strand displacement loops as artificial transcription promoters. PNAS 91(9):3892-5 (1994) |

Any oligopeptide may be used as a component of the compound of the invention since in principle any oligopeptide can be detectable. The oligopeptide structures of the compounds of this invention may be or include epitope tags such as V5-tag, Myc-tag, HA-tag, FLAG-tag, GST-tag, and His-tags or any other amino acid sequence for which antibodies with suitable specificity and affinity are generated. [See also Huang and Honda, C E D: a conformational epitope database. BMC Immunology 7:7 http://www.biomedcentral.com/1471-2172/7/7#B1. Retrieved Feb. 16, 2011 (2006); and Walker and Rapley, Molecular biomethods handbook. Pg. 467 (Humana Press, 2008).] One of ordinary skill in the art will understand essentially any oligopeptide may be used as a marker in the invention and thus be a component of the compounds of the present invention.

In general the oligopeptide of the invention will range from 5 to 50 amino acids in length, most typically from 5 to 30 amino acids in length, e.g. from 10-30 or from 12-25 amino acids in length.

Those skilled in the art will be aware of how to produce antibody molecules when provided with an oligonucleotide of the present invention. For example, polyclonal antisera or monoclonal antibodies can be made using standard methods. A mammal, (e.g., a mouse, hamster, or rabbit) can be immunized with an immunogenic form of the oligonpeptide which elicits an antibody response in the mammal. Techniques for conferring immunogenicity on a oligopeptide include conjugation to carriers or other techniques well known in the art. For example, the oligopeptide can be administered in the presence of an adjuvant. The progress of immunization can be monitored by detection of antibody titers in plasma or serum. Standard ELISA or other immunoassay can be used with the immunogen as antigen to assess the levels of antibodies. Following immunization, antisera can be obtained, and, if desired IgG molecules corresponding to the polyclonal antibodies may be isolated from the sera.

To produce monoclonal antibodies, antibody producing cells (lymphocytes) can be harvested from an immunized animal and fused with myeloma cells by standard somatic cell fusion procedures thus immortalizing these cells and yielding hybridoma cells. Such techniques are well known in the art. Hybridoma cells can be screened immunochemically for production of antibodies which are specifically reactive with the oligopeptide, and monoclonal antibodies isolated.

To enhance their immunogenicity, it is well-known to conjugate small oligopeptide fragments to a hapten, such as, for example, dinitrophenyl (DNP), m-maleimidobenzoyl-N-hydroxyl-N-hydroxysuccinimide ester (MBS), or m-amino benzene sulphonate. A "hapten" is a non-immunogenic molecule that will react with a preformed antibody induced by an antigen or carrier molecule. Alternatively, the immunogenicity of oligopeptides may be enhanced by conjugating the oligopeptide to a carrier molecule, such as, for example, an antigenic oligopeptide, that may be conjugated to a hapten. As will be known to those skilled in the art, a "carrier" is generally an antigenic molecule. Preferred carrier molecules for this purpose include ovalbumin, KLH, and PHA.

The term "antibody" as used herein, is intended to include fragments thereof which are also specifically reactive to an oligopeptide as described herein.

Immunoassays are useful in detecting the presence of an oligopeptide as disclosed herein, in a cell. Such an immunoassay is of particular use in detecting the presence of a DNA in a cell in certain embodiments of the invention. Immunoassays are also useful for the quantitation of said DNA in a cell. The invention described herein extends to all such uses of immunointeractive molecules and diagnostic assays requiring said immunoassays for their performance.

A wide range of immunoassay techniques may be such as those described in U.S. Pat. Nos. 4,016,043, 4,424,279 and 4,018,653. These methods may be employed for detecting the presence of a DNA in some embodiments the invention.

Any cell or nuclear entry sequence can be used within the ecPNA molecules of the invention. In a preferred embodiment, the cell or nuclear entry sequence comprises at least one sequence selected from the group consisting of: (a) a TAT peptide having the sequence YGRKKRRQRRR (SEQ ID NO: 6), (b) a TAT peptide variant having the sequence selected from GRKKRRQRRRPPQ (SEQ ID NO: 7), YARKARRQARR (SEQ ID NO: 8), YARAAARQARA (SEQ ID NO: 9), YARAARRAARR (SEQ ID NO: 10), and YARAARRAARA (SEQ ID NO: 11), (c) an NLS peptide having the sequence PKKKRKV (SEQ ID NO: 12), (d) a penetratin peptide having the sequence selected from RQIKIWFQNRRMKWKK (SEQ ID NO: 13), KKWKMRRNQFWIKIQR (SEQ ID NO: 14), RQIKIWFQNRRMKWKK (SEQ ID NO: 15), RQIKIWFPNRRMKWKK (SEQ ID NO: 16), RQPKIWFPNRRMPWKK (SEQ ID NO: 17), RQIKIWFQNMRRKWKK (SEQ ID NO: 18), RQIRIWFQNRRM- RWRR (SEQ ID NO: 19), and RRWRRWWRRWWRRWR (SEQ ID NO: 20), (e) an Antennapedia domain pAntp(43-58) having the sequence RQILIWFQNRRMKWKK (SEQ ID NO: 22), (f) pVEC(615-632) having the sequence LLIILR-RRIRKQAHAHSK (SEQ ID NO: 23), (g) a model amphipathic peptide (MAP) having the sequence KLALKLALKA-LKAALKLA (SEQ ID NO: 24); and (h) a transportan 10 peptide having the sequence AGYLLGKINLKALAALAK-KIL (SEQ ID NO: 25).

Any transcription activation or repression domain can be used within the ecPNAs of the invention. In a preferred embodiment, the transcription activation domain comprises at least one sequence selected from the group consisting of: (a) a VP2 domain having the sequence DFDLDMLGD-FDLDMLG (SEQ ID NO: 26) or the sequence MLGDFDLD-MLGDFDLD (SEQ ID NO: 30), (b) an ATF-14 domain having the sequence CGSDALDDFDLDML (SEQ ID NO: 27), (c) an AH domain having the sequence PEF-PGIELQELQELQALLQQ (SEQ ID NO: 28), and (d) a Gal80BP domain having the sequence RHGEKWFLDDFT-NNQMDQDY (SEQ ID NO: 29). Preferred repression domains include the engrailed repression domain, the HID (HDAC interaction domain) from the Sin3A protein, and MSRRKQSKPRQI (SEQ ID NO: 47). MSRRKQSKPRQI is a repression motif shared by the transcriptional repression proteins FOG12 and Sall1. [See, Manwani and Bieker, Exp. Hem. 35:39-47 (2007); Lin et al., The N termini of Friend of GATA (FOG) proteins define a novel transcriptional repression motif and a superfamily of transcriptional repressors. J Biol Chem 279(53):55017-23 (2004); and Lauberth and Rauchman, A conserved 12-amino acid motif in SAll1 recruits the nucleosome remodeling and deacetylase corepressor complex. J Biol Chem 281(33)23922-31 (2006)]

Aspects of the invention relate to ecPNAs that downregulate the transcription of specific target genes. ecPNAs which downregulate the transcription of specific target genes may comprise the FOG12 repression motif, which has amino acids in the sequence: MSRRKQSKPRQI (SEQ ID NO: 47). When this motif is fused with the TAT-PNA78 sequence, the resultant TAT-PNA78-MSRRKQSKPRQI (referred to herein as "TAT-PNA78-FOG12")(TAT-PNA78-(SEQ ID NO: 47)) molecule represses, rather than activates, γ globin expression.

In one specific embodiment, the ecPNA molecule is ATF-Bio/PNA/TAT having the structure H$_2$N-CGSDALD-DFDLDML-Biotin-O-PNA-O-YGRKKRRQRRR ((SEQ ID NO: 27)-Biotin-O-PNA-O-(SEQ ID NO: 6)). In another specific embodiment, the ecPNA molecule is ATF-Bio/PNA78/TAT having the structure H$_2$N-CGSDALDDFDLDML-Biotin-O-TACTCTAAGACTATT-O-YGRKKRRQRRR ((SEQ ID NO: 27)-Biotin-O-(SEQ ID NO: 1)-O-(SEQ ID NO: 6)). In yet another specific embodiment, the ecPNA molecule is VP2/PNA78/TAT having the structure Biotin-OO-DFDLDMLGDFDLDMLG-O-TACTCTAAGAC-TATT-O-YGRKKRRQRRR (Biotin-OO-(SEQ ID NO: 26)-O-(SEQ ID NO: 1)-O-(SEQ ID NO: 6)). In the above structures, "O" represents the stable polyether linker, AEEA (2-aminoethoxy-2-ethoxyacetic acid). In a preferred embodiment, all TAT amino acids in such ecPNA molecules are in D-isomer form. In any of these embodiments, the inclusion of Biotin (Bio) is optional. Other markers useful for visualizing an ecPNA molecule, such as but not limited to GFP and other fluorescent markers, may also be optionally included in the ecPNA molecules.

In certain embodiments, the ecPNA molecule has TAT in the D or L form. In certain embodiments, the transactivating domain is in the D or L form.

Methods for producing PNA-peptide conjugates of the present invention are well known in the art and include, among others, solid-phase synthesis and fragment ligation [see, e.g., de Koning et al., Current Opinion in Chemical Biology, 2003, 7(6):734-740]. Linkers useful in the PNA-peptide conjugates of the present invention include, for example, stable polyether, AEEA (2-aminoethoxy-2-ethoxyacetic acid), cleavable disulfide linkages, or other linkers that are generally known in the art.

In some embodiments, an ecPNA molecule is used to activate γ-globin expression in a patient by ex vivo treatment of bone marrow cells prior to placement of the bone marrow cells back into the sickle or thalassemic patient.

Figure 21:
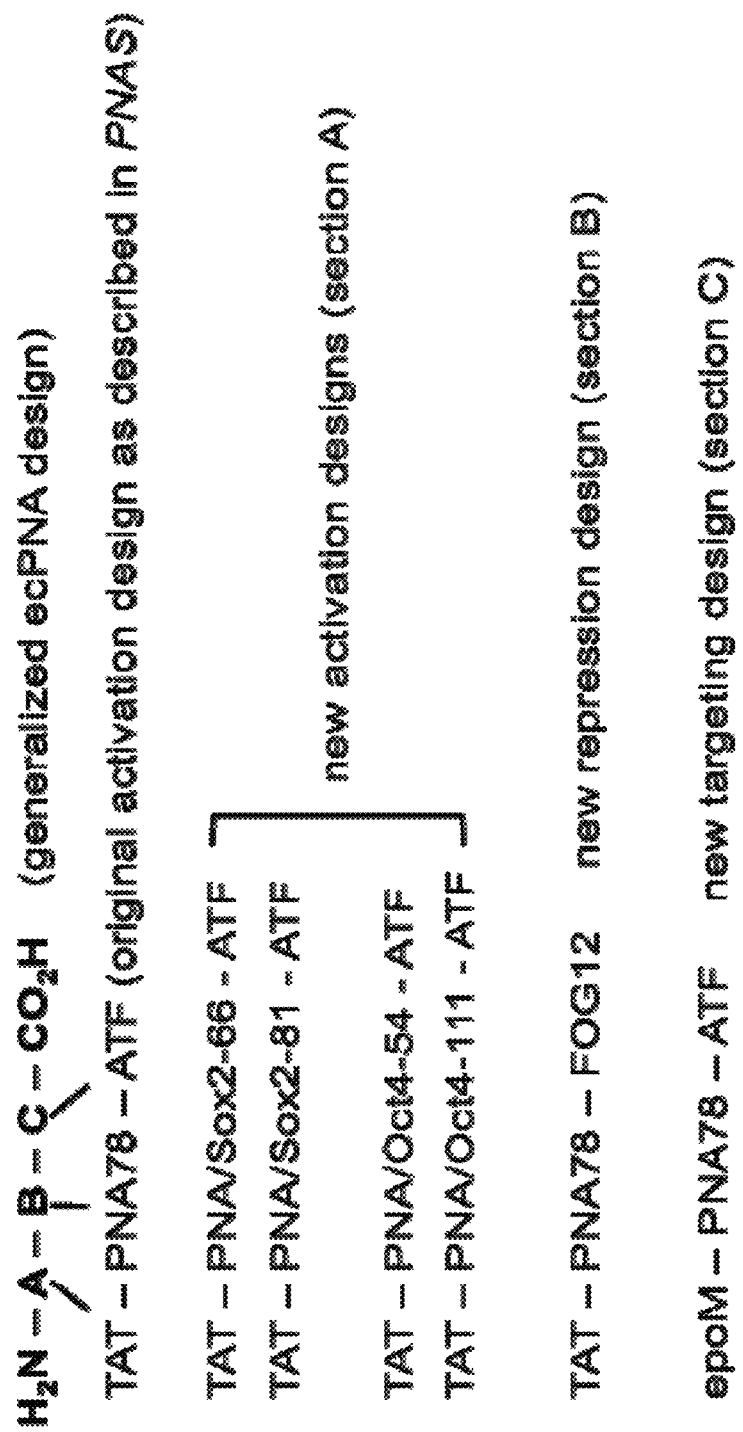
FIG. 21 shows a schematic of ecPNA molecules. Top is the general ecPNA layout as described herein. Immediately below is the TAT-PNA78-ATF activation molecule as used in the PNAS manuscript. Below this are the four activation variants containing either SOX2- or OCT4-specific PNA sequences as described in the text (part A). Below this is the repression molecule containing the FOG12 repression motif as described in the text (part B). Finally, below this is the Epo mimetic (epoM) design described in the text (part C). All molecules contain biotin for ease of detection (not shown).

Aspects of the invention relate to the systemic injection of ecPNAs. In some embodiments, the ecPNA comprises a compound that binds a receptor on the surface of a cell. In some embodiments, the ecPNA comprises a compound that is capable of binding to a receptor that is present on the surface of a certain type or types of cells. Thus, embodiments of the invention encompass the specific targeting of a specific cell type or types within a subject with an ecPNA, wherein the ecPNA that is administered to the subject comprises a compound that binds to a receptor on the specific cell type(s). For instance, erythroid cells could be targeted by using an ecPNA which comprises a compound that binds to the erythropoietin (Epo) receptor. The compound may be an Epo mimetic. Epo mimetics and other compounds that bind the Epo receptor include but are not limited to Epo mimetic peptides (EMPs), Hematide, and others discussed in Bunn H F. New agents that stimulate erythropoiesis. Blood. February 1; 109(3):868-73 (2007), the entire contents of which are hereby incorporated herein by reference. In a non-limiting example, an EMP-PNA78-ATF ecPNA which upregulates γ-globin expression is administered to a subject systemically, but enters specifically into erythroid cells in the subject which has been injected with the ecPNA after binding of the EMP portion of the ecPNA to the erythropoietin receptor on those cells (see, e.g. FIG. 21).

Compositions

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice.

Accordingly, in one aspect, the present invention provides a pharmaceutical composition or formulation comprising at least one ecPNA molecule of the invention, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof. Preferably, the at least one ecPNA molecule is present in such compositions in a therapeutically effective amount.

The compositions of the invention can be formulated for administration in any convenient way for use in human or veterinary medicine.

Carrier

The term "carrier" refers to a diluent, adjuvant, excipient, or vehicle with which the compound is administered. Such carriers can be sterile liquids, such as water and oils, including those of petroleum, animal, vegetable or synthetic origin, such as peanut oil, soybean oil, mineral oil, sesame oil and the like. In some embodiments, carriers are pharmaceutical carriers. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin (1990, Mack Publishing Co., Easton, Pa. 18042).

Formulations

The compositions and formulations of the present invention may comprise pharmaceutically or otherwise acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hylauronic acid may also be used. See, e.g., Remington's Pharmaceutical Sciences, 18th Ed. (1990, Mack Publishing Co., Easton, Pa. 18042) pages 1435 1712 which are herein incorporated by reference.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, preserving, wetting, emulsifying, and dispersing agents. The pharmaceutical compositions may be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Methods of the Invention

In conjunction with ecPNA molecules, the present invention provides methods for using such molecules, or compositions containing such molecules, to activate or repress transcription of a target gene. Important genes that may be targeted by the ecPNA molecules of the present invention include, for example, activation of γ-globin (for treatment of β-thalassemia or sickle cell disease, activation of the p15 tumor suppressor gene for treatment of cancer, and repression of the BCR/ABL oncogene (for treatment of leukemia).

In one specific embodiment, the present invention provides a method for upregulating transcription of a γ-globin gene in a bone marrow mammalian cell comprising contacting said cell with an ecPNA molecule having the structure $H_2N$-CGS-DALDDFDLDML-Biotin-O-TACTCTAAGACTATT-O-YGRKKRRQRRR (ATF-Bio/PNA78/TAT) ((SEQ ID NO: 27)-Biotin-O-(SEQ ID NO: 1)-O-(SEQ ID NO: 6)). In another specific embodiment, the present invention provides a method for upregulating transcription of a γ-globin gene in a bone marrow mammalian cell comprising contacting said cell with an ecPNA molecule having the structure Biotin-OO-DFDLDMLGDFDLDMLG-O-TACTCTAAGACTATT-O-YGRKKRRQRRR (VP2/PNA78/TAT) (Biotin-OO-(SEQ ID NO: 26)-O-(SEQ ID NO: 1)-O-(SEQ ID NO: 6)).

Since the PNA portion of the ecPNA molecules of the present invention can be directed to any promoter region of a target gene of interest, the present invention provides a potentially powerful yet low-toxic treatment for any disorder that can be alleviated by activation or repression of a target gene.

In certain specific embodiments, the invention provides a method for treating a β-globin disorder in a mammal comprising administering to the mammal a therapeutically effective amount of an ecPNA molecule which upregulates the transcription of a γ-globin gene. Non-limiting examples of encompassed β-globin disorders include sickle cell anemia and β-thalassemia.

The human γ-globin (HBGI) mRNA sequence has GenBank Accession No. NM_000559 (SEQ ID NO: 42). The human γ-globin amino acid sequence has GenBank Accession No. NP_000550 (SEQ ID NO: 43). The human β-globin mRNA sequence has GenBank Accession No. NM_000518 (SEQ ID NO: 44). The human β-globin amino acid sequence has GenBank Accession No. NP_000509 (SEQ ID NO: 45). The gene region on chromosome 11 containing the human epsilon, gamma G, gamma A, beta 1 pseudogene, delta, and beta-3' globin genes has GenBank Accession No. NG_000007 (SEQ ID NO: 46).

Induction of iPS Cells

In conjunction with the ecPNAs of the invention, methods for inducing iPS cells comprising administering ecPNA molecules to a cell are provided.

Induced pluripotent stem (iPS) cells may be used to generate any differentiated tissue from an individual in need of the differentiated tissue. The differentiated tissue may then be provided to the individual, avoiding tissue rejection and other complications that may arise from an individual receiving differentiated tissue from a non-self source. Blood cells may be induced to iPS status by the introduction of only two transcription factors (OCT4 and SOX2), and ecPNA molecules described herein are a means to efficiently and selectively activate the OCT4 and SOX2 genes in vivo. ecPNA molecules are also described in PCT International Application Publication No. WO2011/103215, and (Chen et al. Design of Embedded Chimeric Peptide Nucleic Acids that Efficiently Enter and Accurately Reactivate Gene Expression In Vivo. PNAS 107, 16846-16851 (2010)), the entire contents of which are hereby incorporated herein by reference. In some embodiments, ecPNA molecules that activate OCT4 and SOX2 in primary human blood cells are used as a means to induce them to iPS status.

In certain embodiments, the iPS cells are generated in vitro. Preferably, iPS cells are induced by introducing an ecPNA molecule that upregulates transcription of OCT4. In certain embodiments, iPS cells are induced by introducing an ecPNA molecule that upregulates transcription of OCT4 and an ecPNA molecule that upregulates transcription of OCT4. In certain embodiments, ecPNA molecules specific for SOX2 and/or OCT4 are administered to a cell with additional ecPNA molecules specific for the induction of one or more other genes. For example, the one or more other genes can include without limitation c-MYC, KLF4, LIN28, NANOG, PRDM14 and NFRKB [see, Chia, N Y et al. Nature; 2010; 468(7321)316-320]. The ecPNA molecules can target any gene useful for the induction of iPS cells, and can be used in any combination (of different target gene specificities) suitable for the induction of iPS cells.

Any suitable cell type can be used for the generation of iPS cells (these cells are referred to herein as "source cells"). In a preferred embodiment, iPS cells are induced from CD34+ peripheral blood cells, bone marrow cells, and/or CD133+ cord blood (CB) cells. Other suitable source cells include without limitation fibroblasts, hepatocytes, gastric epithelial cells, mesenchymal cells, neural cells [see, Kim, J. B. et al., Nature. 2009 Oct. 1; 461(7264):649-3] and other somatic cells [see, Aoi et al, (2008) Science 321: 699-702; Park et al, 2008; Nature 451: 141-146; Tsai et al., Stem Cells: 28, 221-228 (2010); Szabo et al. Nature, in press, doi: 10.1038/nature09591]. The source cells for iPS induction can be derived from any suitable mammalian source cell, such as but not limited to murine or primate cells, and preferably human cells. The source cells may be obtained, for example and without limitation, from a cell line, from a patient or from a donor source. Methods for the isolation and culture of source cells are known in the art. The following methods are provided as examples and are not limiting. Any suitable method for the isolation of source cells for iPS cell generation and for their culture, are contemplated for use in the present invention.

For the isolation and culture of peripheral blood cells, the following procedure can be followed. Mobilized peripheral blood can be obtained as follows: the donor is injected with 5 µg/kg/day for 3 days with Neupogen (G-CSF) manufactured by Amgen. On the fourth day, apheresis of 7 blood volumes is performed on a Cobe Apheresis machine, and 300 ml of blood is collected. Using this method, the yield of CD34+ cells is about 1%. For culture, mobilized peripheral blood CD34+ cells (Allcells, mPB014F) can be maintained in IMDM (Invitrogen) containing 15% fetal bovine serum (StemCell Technologies) supplemented with hSCF (100 ng/ml), hFlt3L (100 ng/ml), and Interleukin-3 (20 ng/ml) (Peprotech). CD34+ cells grown in culture for four days can then be used for treatment with ecPNA molecules of the invention. Once iPS cells begin to form, cell clusters can be mechanically scraped into strips and transferred to 6-well, low attachment plates in differentiation medium consisting of knockout DMEM (Invitrogen) supplemented with 20% fetal bovine serum (StemCell Technologies), 0.1 mM non-essential amino acids (Invitrogen), 1 mM L-glutamine (Invitrogen), 50 µg/ml ascorbic acid (Sigma), and 2 mg/ml human holo-transferrin (Sigma) and 0.1 mM (1-mercaptoethanol (Sigma). [See, Loh et al. (2009) Blood; 113(22):5476-5479.]

For the isolation of CB cells, the following procedure can be followed. Umbilical CB samples can be obtained from a suitable source, such as cord blood bank. Mononuclear cells (MNC) are isolated from CB using Lympholyte-H (Cederlane, Ontario, Calif.) density gradient centrifugation. CD133+ cells are positively selected using Mini-Macs immunomagnetic separation system (Miltenyi Biotec, Bergisch Gladbach, Germany). Purification efficiency is verified by flow cytometric analysis staining with CD133-phycoerythrin (PE; Miltenyi Biotec, Bergisch Gladbach, Germany) antibody.

For the culture of CB cells and induction of iPS cells, CB CD133+ cells ($0.08 \times 10^5$ cells per ml) are pre-stimulated for 24 h in DMEM supplemented with 10% of FBS in the presence of SCF (50 ng/ml)+Flt3 (50 ng/ml)+TPO (10 ng/ml)+IL-6 (10 ng/ml) (PeproTech). Multi-well non-tissue culture-treated plates were coated with retronectin (Takara, Otsu, Japan, www.takara-bio.com), a fibronectin fragment CH-296 (15 mg/cm2), and preloaded by centrifuging the plates with a filtered equal molar mix of ecPNA molecules specific for target genes (e.g., OCT4 and/or SOX2, and optionally, KLF4, c-MYC, LIN28, NANOG, PRDM14, and/or NFRKB) at 2,500 RPM for 30 minutes. About 80,000 CD133+ cells are plated in the presence of DMEM+10% FBS and the cytokine cocktail mentioned above[see, Giorgetti, A. et al. (2009) Cell Stem Cell; 5:353-357.]

For the analysis of gene expression in iPS cells, any suitable method, such as PCR or Southern blot can be used. For example, genomic DNA from the iPS cells can be isolated using All Prep DNA/RNA columns (Qiagen), following manufacturer's guidelines. 4 □g of genomic DNA digested with 40 U of either PstI or HindIII restriction enzyme (New England Biolabs) can be loaded and electrophoresed on a 1% agarose gel, transferred to a neutral nylon membranes (Hybond-N, Amersham) and hybridized with DIG-dUTP labeled probes generated by PCR using the PCR DIG Probe Synthesis Kit (Roche Diagnostics). Probes can be detected by an APconjugated DIG-Antibody (Roche Diagnostics) using CDP-Star (Sigma-Aldrich) as a substrate for chemiluminescence. Conditions are as per the instructions of the manufacturer. The probes can be generated using SOX2, OCT4, KLF4 and c-MYC cDNAs as templates with the following primers (F, forward; R, reverse): SOX2 F 5'-AGTACAACTCCAT-GACCAGC-3' (SEQ ID NO: 48); SOX2 R 5'-TCACATGT-GTGAGAGGGGC-3' (SEQ ID NO: 49); OCT4 F 5'-TAAGCTTCCAAGGCCCTCC-3' (SEQ ID NO: 50); OCT4 R 5'-CTCCTCCGGGTTTTGCTCC-3' (SEQ ID NO: 51); KLF4 F 5'-AATTACCCATCCTTCCTGCC-3' (SEQ ID NO: 52); KLF4 R 5'-TTAAAAATGCCTCTTCATGTGTA-3' (SEQ ID NO: 53); c-MYC F 5'-TCCACTCGGAAGGAC-TATCC-3' (SEQ ID NO: 54); c-MYC R 5'-TTACGCACAA-GAGTTCCGTAG-3' (SEQ ID NO: 55). Probes and primers can be readily designed for any target gene encompassed by the invention by one of ordinary skill in the art.

Following iPS cell induction according to the methods described herein or other suitable methods, iPS cells can be analyzed for expression of markers characteristic of iPS cells in order to confirm successful iPS cell induction. Examples of suitable markers include OCT4, SOX2, TRA-1-81, TRA-1-60, SSEA3, SSEA4, CRIPTO, REX1 and NANOG genes and/or proteins, although a number of other markers are also possible. In certain embodiments, immunofluorescence can be used to characterize iPS cells. iPS can be grown on plastic coverslide chambers and fixed with 4% paraformaldehyde (PFA). The following antibodies can be used for staining: TRA-1-60 (MAB4360, 1:200), TRA-1-81 (MAB4381, 1:200), SOX2 (AB5603, 1:500) all Chemicon, SSEA-4 (MC-813-70, 1:2), SSEA-3 (MC-631, 1:2) all Iowa, Tuj1 (1:500; Covance), α-fetoprotein (1:400; Dako), α-actinin (1:100; Sigma), OCT4 (C-10, SantaCruz, sc-5279, 1:100), NANOG (Everest Biotech EB06860, 1:100), GATA 4 (1:50, SantaCruz), smooth muscle actin (1:400, Sigma), FoxA2 (1:50 R&D System), GFAP (1:1000, Dako), α-sarcomeric actin (1:400, Sigma), Anti-Flag (Sigma M2). Images can be taken using, e.g., a Leica SP5 confocal microscope. Direct AP activity can be analyzed using an Alkaline Phosphatase Blue/Red Membrane substrate solution kit (Sigma) according to the manufacturer's guidelines. Additional methods for the culture and characterization of iPS cells are described in detail in Giorgetti, A. et al. (2009), supra; Loh et al. (2009) supra; and Takahashi, K. et al. (2007) supra.

In certain embodiments, iPS cells generated according to methods of the invention can be then be differentiated into specific cell types in vitro. For example, once iPS cells are generated, it may then be desirable to generate a specific cell type from these cells, e.g., for treatment of a patient in need of treatment with a specific type of cell. Methods for differentiating iPS cells are known in the art [see, Giorgetti, A. et al. (2009), supra.; and Warren, et al. (2010) Stem Cell (7) in press; PMID: 20888316].

Dosage and Administration ecPNA-containing compositions of the invention can be directly or indirectly administered to a subject (e.g. patient).

Indirect administration is performed, for example, by administering the composition to cells (e.g., bone marrow cells, peripheral blood cells, CB cells or any other suitable cell) in vitro or ex vivo (i.e. the source cells may be derived from cell lines (in vitro) or obtained from the patient to be treated or from another donor source (ex vivo)), and subsequently administering the treated cells to the patient.) ex vivo and subsequently introducing the treated cells to the patient. The cells may be obtained from the patient to be treated or from a genetically related or unrelated patient. Related patients offer some advantage by lowering the immunogenic response to the cells to be introduced. For example, using techniques of antigen matching, immunologically compatible donors can be identified and utilized. Following treatment of the cells with a composition of the invention, the cells may be administered to a patient in need of such treatment by any suitable route, such as oral, parenteral, sublingual, rectal such as suppository or enteral administration, or by pulmonary absorption or topical application. In a preferred embodiment, the cells are administered intravenously.

Direct administration of an ecPNA-containing composition to a subject may also be by oral, parenteral, sublingual, rectal such as suppository or enteral administration, or by pulmonary absorption or topical application.

In certain embodiments iPS cells generated according to the methods described herein are administered to a patient. In some embodiments, the iPS cells are administered intravenously, although it is possible to administer the cells subcutaneously, intranasasally, orally, or by any other suitable route of administration. Methods for administering cells to a subject are known in the art.

In certain embodiments, an ecPNA molecule-containing composition or an iPS cell generated according to the methods described herein, or a cell differentiated from an iPS cell generated according to the methods described herein is administered directly to a site of injury or disease in a subject. For example it may be useful to directly administer an ecPNA molecule for inducing an iPS cell directly to a site where it would be useful to induce stem cell development. Such stem cells could then differentiate into a desired tissue type under the control of the cytokine milieu present at the targeted site.

Parenteral administration may be by intravenous injection, subcutaneous injection, intramuscular injection, intra-arterial injection, intrathecal injection, intraperitoneal injection or direct injection or other administration to one or more specific sites. Injectable forms of administration are sometimes preferred for maximal effect in, for example, bone marrow. When long-term administration by injection is necessary, venous access devices such as medi-ports, in-dwelling catheters, or automatic pumping mechanisms are also preferred wherein direct and immediate access is provided to the arteries in and around the heart and other major organs and organ systems.

Another effective method of administering the composition is by direct contact with, for example, bone marrow through an incision or some other artificial opening into the body. Compositions may also be administered to the nasal passages as a spray. Arteries of the nasal area provide a rapid and efficient access to the bloodstream and immediate access to the pulmonary system. Access to the gastrointestinal tract, which can also rapidly introduce substances to the blood stream, can be gained using oral, enema, suppository, or injectable forms of administration. Compositions may be administered as a bolus injection or spray as appropriate. Compositions may be given sequentially over time (episodically) such as every two, four, six or eight hours, every day (QD) or every other day (QOD), or over longer periods of time such as weeks to months. Compositions may also be administered in a timed-release fashion such as by using slow-release resins and other timed or delayed release materials and devices. Orally active compositions are more preferred as oral administration is usually the safest, most convenient and economical mode of drug delivery. However, direct injection may be preferred when immediate access to the blood system is desired.

Treatments to the patient may be therapeutic or prophylactic. Therapeutic treatment involves administration of one or more compositions of the invention to a patient suffering from one or more symptoms of the disorder. Symptoms typically associated with globin disorders include, for example, anemia, tissue hypoxia, organ dysfunction, abnormal hematocrit values, ineffective erythropoiesis, abnormal reticulocyte count, abnormal iron load, splenomegaly, hepatomegaly, impaired peripheral blood flow, dyspnea, increased hemolysis, jaundice, anemic crises and pain such as angina pectoris. Relief and even partial relief from one or more of these symptoms correspond to an increased life span or simply an increased quality of life. Further, treatments that alleviate a pathological symptom can allow for other treatments to be administered.

Prophylactic treatments involve pulsed administration of a composition to a patient having a confirmed or suspected blood disorder without having any overt symptoms. For example, otherwise healthy patients who have been genetically screened and determined to be at high risk for the future development of a blood disorder may be administered compositions of the invention prophylactically. Administration can begin at birth and continue, if necessary, for life. Both prophylactic and therapeutic uses are readily acceptable because these compounds are generally safe and non-toxic.

It will be appreciated that the amount of the ecPNA-containing compositions of the invention required for use in treatment will vary with the route of administration, the nature of the condition for which treatment is required, and the age, body weight and condition of the patient, and will be ultimately at the discretion of the attendant physician or veterinarian. These compositions will typically comprise a therapeutically effective amount of the compositions of the invention. Preliminary doses can be determined according to animal tests, and the scaling of dosages for human administration can be performed according to art-accepted practices.

Keeping the above description in mind, typical dosages of an ecPNA molecule of the invention for ex vivo or in vitro use range from about 1 μM to about 10 μM. Typical dosages of an ecPNA molecule of the invention for in viva use range from about 0.1 mg/kg to about 100 mg/kg.

Keeping the above description in mind, typical dosages of cells (e.g., bone marrow cells or peripheral blood cells) that have been treated with an ecPNA composition of the invention ex viva for subsequent administration to a patient range from about $1\times10^5$ to about $1\times10^7$ cells per kg of body weight. In a preferred embodiment, the dosage is about $1\times10^6$ cells/kg body weight.

Combination Treatments

The present invention also encompasses combination treatments, wherein an additional agent or agents can be administered to a patient conjointly with an ecPNA of the invention (e.g., in the same composition as the ecPNA or in separate compositions, at the same or different sites, at the same or different times, and for the same or different duration of time). In some embodiments, the additional agent or agents are effective for enhancing the desired effect of the ecPNA on gene expression.

Non-limiting examples of such combination treatments for β-globin disorders include conjoint administration of a γ-globin-specific ecPNA with a second agent such as, for example, hydroxyurea, a short chain fatty acid (SCFA) inducer (e.g., butyrate), 5-azacytidine, or a histone deacetylase inhibitor (e.g., suberoylanilide hydroxamic acid [SAHA]). For example, a pulsed butyrate regimen was shown to work best to effectively increase γ-globin levels in patients who already exhibited a slightly higher baseline level (≥2%) of fetal hemoglobin (HbF) production. [See, Atweh, G. F. et al. Sustained induction of fetal hemoglobin by pulse butyrate therapy in sickle cell disease. Blood 93, 1790-1797 (1999).]

In certain embodiments, ecPNA molecules are administered to source cells in combination with one or more small molecules for the induction of iPS cells. For example, small molecules that rearrange chromatin can be administered to increase the efficiency of iPS cell generation. [See, Abujarour and Ding; (2009) Genome Biology 10: 220; Lin et al. (2009) Nature Methods 6, 805-808.]

In other embodiments, ecPNA molecules can be administered to cells with one or more cytokines or other active agents that increase the efficiency of iPS cell generation. Suitable cytokines or other active agents are readily determined by one of ordinary skill in the art.

EXAMPLES

The following examples are included to demonstrate certain embodiments of the invention. It should be appreciated by those of skill in the art that the techniques disclosed in the examples constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Design, Synthesis, and Storage of PNA

A previous study that used PNA to alter γ-globin expression relied on a triplex-forming "clamp" design that forms a Hoogstein PNA/DNA/PNA triple helix. [See Wang, G. et al., Peptide nucleic acid (PNA) binding-mediated induction of human gamma-globin gene expression. Nucleic Acids Res 27, 2806-2813 (1999); and Pooga, M., Land, T., Bartfai, T. & Langel, U., PNA oligomers as tools for specific modulation of gene expression. Biomol Eng 17, 183-192 (2001).] However, this design has significant limitations, as it requires the use of base analogues that are not all commercially available and the presence of homopurine/homopyrimidine sequences at the target site. [See Kaihatsu, K., Janowski, B. A. & Corey, D. R., Recognition of chromosomal DNA by PNAs. Chem Biol 11, 749-758 (2004).] Further, the possible number of DNA targets was significantly limited using this approach.

In the present invention, it was desired to streamline this approach by designing short, complementary single stranded PNAs which function via strand invasion and which can accommodate a wider range of DNA targets. By dividing the proximal γ-globin promoter (−202 to +33; SEQ ID NO: 41) into fifteen segments, four (4) 12- to 15-mer sequences suitable for PNA synthesis were identified that correspond to the γ-globin promoter at positions −150, −116, −78, −7, relative to the transcription start site (FIG. 1(a)). All PNAs were synthesized by Biosynthesis Inc. (Lewisville, Tex.) and have the following structures: PNA7: Biotin-OO-TGTGGAACT-GCTGAA-O-k (Biotin-OO-(SEQ ID NO: 2)-O-k); PNA78: Biotin-OO-TACTCTAAGACTATT-O-k (Biotin-OO-(SEQ ID NO: 1)-O-k); PNA116: Biotin-OO-GGCTATTGGT-CAAGGC-k (Biotin-OO-(SEQ ID NO: 3)-k); PNA150: Biotin-OO-GAGTTTAGCCAGG-O-k Biotin-OO-(SEQ ID NO: 4)-O-k); PNA78/NLS: Biotin-OO-TACTCTAAGAC-TATT-O-PKKKRKV (Biotin-OO-(SEQ ID NO: 1)-O-(SEQ ID NO: 12)); PNA78/TAT: Biotin-OO-TACTCTAAGAC-TATT-O-YGRKKRRQRRR (Biotin-OO-(SEQ ID NO: 1)-O-(SEQ ID NO: 6)); MUT PNA78/TAT: Biotin-OO-TAC-TATAAAACTATT-O-YGRKKRRQRRR (Biotin-OO-(SEQ ID NO: 88)-O-(SEQ ID NO: 6)); VP2/PNA78/TAT: Bio-OO-DFDLDMLGDFDLDMLG-O-TACTCTAAGACTATT-O-YGRKKRRQRRR (Bio-OO-(SEQ ID NO: 26)-O-(SEQ ID NO: 1)-O-(SEQ ID NO: 6)); Bio-ATF/PNA78/TAT: Bio-OO-CGSDALDDFDLDML-O-TACTCTAAGACTATT-O-YGRKKRRQRRR Bio-OO-(SEQ ID NO: 27)-O-(SEQ ID NO: 1)-O-(SEQ ID NO: 6)); and ATF-Bio/PNA78/TAT: H₂N-CGSDALDDFDLDML-Biotin-O-TACTCTAAGAC-TATT-O-YGRKKRRQRRR ((SEQ ID NO: 27)-Biotin-O-(SEQ ID NO: 1)-O-(SEQ ID NO: 6)). In the above structures, "O" represents the stable polyether linker, AEEA (2-aminoethoxy-2-ethoxyacetic acid). As used throughout the present disclosure, "Bio" is the abbreviated form of "biotin" are used interchangeably. All TAT amino acids were the D-isomer form. PNAs were dissolved in sterile distilled/deionized water and stored at 4° C., and heated at 50° C. for 5 minutes just before any application to prevent aggregation.

Example 2

Magnetic Pull-Down Assay

Figure 1B:
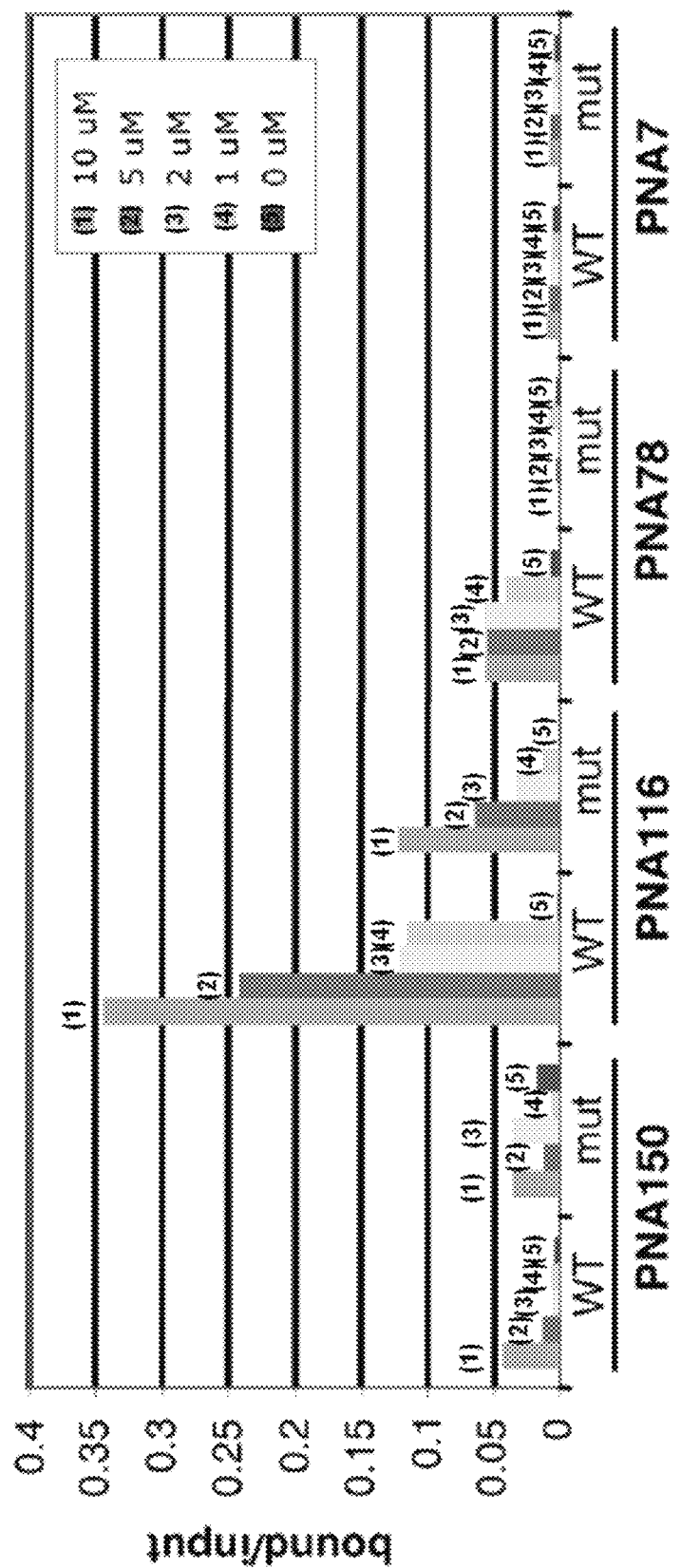
In FIG. 1(b), different concentrations of PNAs (0-10 μM) were incubated with a constant amount of radioactively labeled DNA oligonucleotide (10 nM) containing either the wild type (wt) or mutated (mut) target sequence followed by incubation with streptavidin Dynabeads and collection with a magnetic particle concentrator. Bound/input ratios were obtained after scintillation counter analysis.

A novel assay was developed to monitor specific binding of PNA molecules to their cognate DNA site (FIG. 1(b)). 2 ng of $^{32}$P-labelled double-stranded DNA oligonucleotide (designed at regions of the γ-promoter centered at each of the four PNA target sites) was incubated with various molar excess (0× to 1000×) of PNA at 37° C. overnight in a final volume of 15 uL with 10 mM Tris and 1 mM of EDTA. The resultant material was incubated with equal amount of Dynabeads M280-streptavidin (DYNAL biotech) for 15 seconds at 25° C. Beads had been prepared by washing twice with BW buffer (10 mM Tris, pH7.5, 1 mM EDTA, 2.0M NaCl). The beads were pulled down with a Dynal MPC-S magnetic particle concentrator and washed twice with BW buffer. Samples were finally suspended in 50 uL BW buffer, and radioactivity was counted for 10 minutes in a scintillation counter to yield the average counts per minute (cpm) taken for each sample, which was then divided by the cpm of the input (1 uL of the radio-labeled oligo).

It was found that the ability of each PNA to bind and discriminate between wild type and mutant oligos varied considerably. In the tests, PNA150 or PNA7 did not discriminate or bind well to their target sites under these conditions. However, PNA116 and PNA78 bound their target DNA oligo in proportion to their input. Even though PNA116 has the best recovery rate of its wild type DNA target, it also bound to the mutant DNA target to an unacceptable extent. On the other hand, PNA78 exhibited the best discrimination (~25-fold) and specificity in recognizing its target sequence.

Example 3

KMnO$_4$ Probing and Footprinting

Figure 1C:
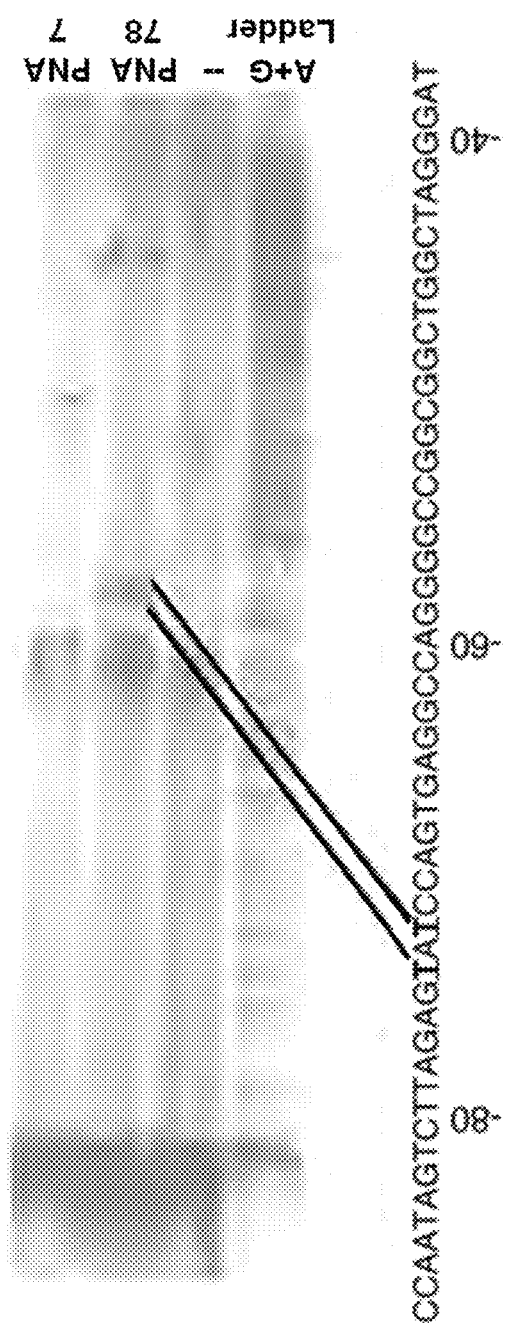
In FIG. 1(c), permanganate probing confirms the specificity of PNA78 by showing that oxidized and cleaved T bases (lane 3) are accessible within the designated target sequence compared to 'no PNA' (--) and PNA7 (as non-interacting PNA) controls. The A+G sequence ladder is shown in lane 1, along with the nucleotide sequence of the γ-globin promoter aligned on the left.

To further confirm the observation in the magnetic-pull down assay, permanganate (KMnO$_4$) probing of the PNA78/DNA interaction in solution was carried out (FIG. 1(c)). In a modification of a published protocol [Bentin, T., Hansen, G. I. & Nielsen, P. E., Measurement of PNA binding to double-stranded DNA. Methods Mol Biol 208, 91-109 (2002)], 1 ng of a singly $^{32}$P-end-labeled, gel purified RsaI/XhoI fragment derived from the p250 plasmid that contains the γ-globin promoter region −299 to +37 was incubated in a volume of 15 μL with a final concentration of 10 mM Tris and 1 mM EDTA for 30 minutes at 37° C. PNA was added at a final concentration of 50 uM for further incubation overnight at 37° C. 1 uL 20 mM KMnO$_4$ was added to the reaction, and after 15 s 10 uL stop buffer (1.5 M sodium acetate, 1 M 2-mercaptoethanol, Ph 7.0) was added. 2.5× vol of 96% ethanol was added and the DNA collected by centrifugation at 13000 rpm for 15 minutes. The supernatant was removed and the DNA pellet dissolved in 100 uL 10% piperidine followed by incubation at 90° C. for 20 minutes. The lympholized DNA sample was resuspended in 8 μL FA buffer (80% deionized fomamide, 10 mM EDTA, 0.25% xylenecyanol FF, 0.25% bromphenol blue). DNA was denatured at 90° C. for 2 minutes, chilled on ice, and then electrophoresed on thin 10% polyacrylamide gels containing 7 M urea. The dried gel was then exposed for autoradiography. KMnO$_4$ probing gives single-base pair resolution and makes it easy to map the PNA78 target site on the γ-promoter when co-electrophoresed adjacent to a separate reaction that generates a partial sequence ladder.

The results demonstrated that PNA78 binds specifically to its target region within the γ-globin promoter fragment, with residues at the 5' end of its interaction most accessible to chemical cleavage. Based on the results of the in vitro studies, PNA78 was used for the remainder of the experiments described in the present Examples.

Example 4

Cellular and Nuclear Localization of PNA

In order to alter transcription, it is necessary for the PNA to reach and enter the cell nucleus. The basis for cellular uptake of PNA is not yet fully understood, although it may be related to passive diffusion [see e.g., Pooga, M., Land, T., Bartfai, T. & Langel, U. PNA oligomers as tools for specific modulation of gene expression. Biomol Eng 17, 183-192 (2001)], particularly as unmodified and slightly modified PNAs have been successfully delivered directly to cells without the use of transfection reagents and protocols. [See Nielsen, P. E., Peptide nucleic acid: a versatile tool in genetic diagnostics and molecular biology. Curr Opin Biotechnol 12, 16-20 (2001); and Sei, S. et al., Identification of a key target sequence to block human immunodeficiency virus type 1 replication within the gag-pol transframe domain. J Virol 74, 4621-4633 (2000).] In order to ascertain whether the PNA molecules efficiently enter an erythroid cell, varying amounts of PNA78 were incubated for different lengths of time with erythroleukemic K562 cells (ATCC deposit number CCL243) and entry and localization was monitored by fluorescent microscopy after incubation with streptavidin-FITC. K562 cells are human erythroid leukemia cells that display similar characteristics of fetal erythrocytes, because they express high levels of γ-globin and no or very low levels of beta globin. [See Stamatoyannopoulos, J. A. & Nienhuis, A. W., Therapeutic approaches to hemoglobin switching in treatment of hemoglobinopathies. Annu Rev Med 43, 497-521 (1992).]

Figure 2A:
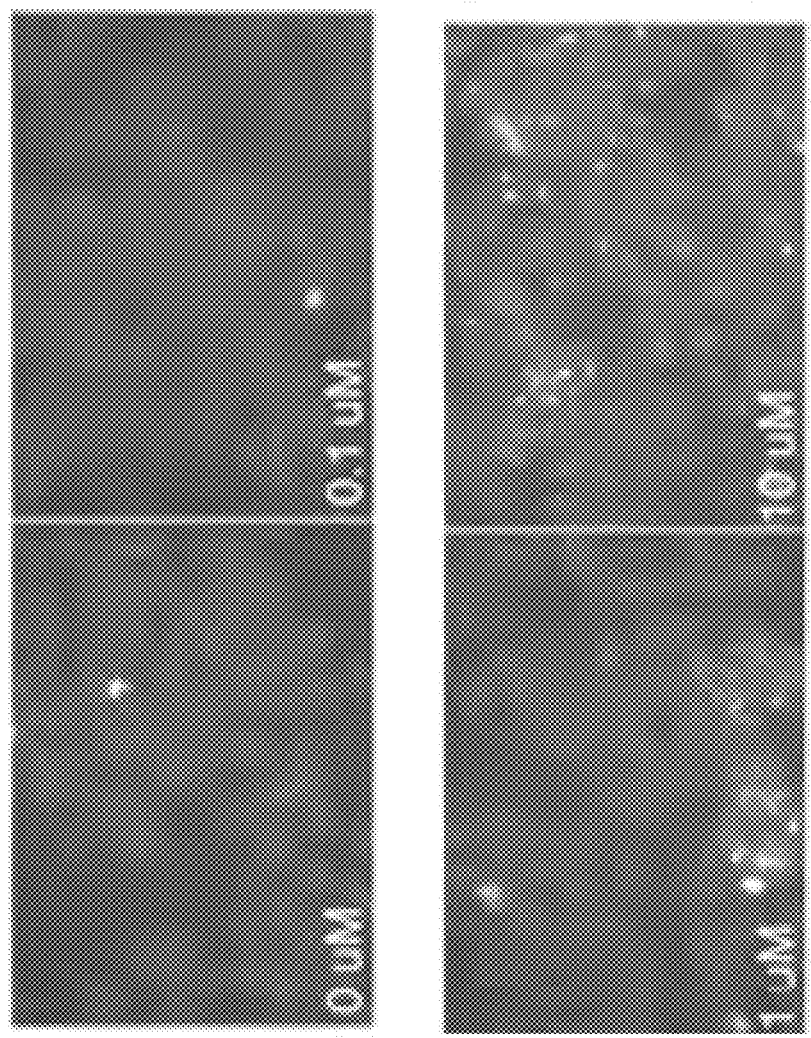
FIG. 2(a) depicts fluorescent microscopy showing uptake of PNA78 by K562 cells exposed to different concentrations as indicated. PNA signals appear as bright punctate dots.

PNA efficiently entered cells after a simple overnight incubation in growth media with an optimal concentration of 10 uM (FIG. 2(a)). Based on published studies, concentrations of PNA as high as 30 uM are not toxic to cultured cells. [See Cutrona, G. et al., Effects in live cells of a c-myc anti-gene PNA linked to a nuclear localization signal. Nat Biotechnol 18, 300-303 (2000).] Although the efficiency of cell entry was high (over 90%) after an overnight incubation, in all cases no evidence of nuclear entry was observed, as all of the PNA molecules remained visible as punctate spots in the cytoplasm.

Cell Culture

COS7 cells were maintained in DMEM (Cellgro®, Mediatech Inc. (Manassas, Va.)) and K562 cells were maintained in RPMI 1640 medium (Gibco®, Invitrogen, Carlsbad, Calif.) supplemented with 10% fetal bovine serum, penicillin and streptomycin. CID-dependent wild type β-YAC mouse bone marrow cells (MBCs) [see Blau, C. A. et al., γ-Globin gene expression in chemical inducer of dimerization (CID)-dependent multipotential cells established from human β-globin locus yeast artificial chromosome (β-YAC) transgenic mice. J Biol Chem 280, 36642-36647 (2005)] were cultured in the presence of AP20187 dimerizer (100 nM; Ariad Pharmaceuticals, Cambridge, Mass.) in Isocove's modified Dulbecco's medium containing 10% fetal bovine serum, penicillin, and streptomycin.

Delivery of PNA to Cells

PNA was introduced into actively growing COS7 cells. For suspension cells, 3×10$^5$ K562 cells or β-YAC MBCs were resuspended with 200 uL OPTI-MEM, and plated on poly-lysine coated 8-well chambered cover glass slides (Nunc) and allowed to attach to the slide overnight. In all cases, PNA was added to a final concentration of 5 uM or 10 uM along with Strepavidin-FITC to a final concentration of 5 ug/mL. Based on published studies, concentrations of PNA as high as 30 uM are not toxic to cultured cells. [See Cutrona, G. et al., Effects in live cells of a c-myc anti-gene PNA linked to a nuclear localization signal. Nat Biotechnol 18, 300-303 (2000).] After 4 hours, 300 uL RPMI 1640 and FBS was added to a final concentration of 10%.

Confocal Analysis and Live Cell Imaging of Cellular Localization of PNAs

A live cell imaging protocol was developed to monitor cellular localization of chimeric PNA molecules. At 16 hours post PNA-treatment, DRAQ5 (Biostatus Limited, UK, [see Martin, R. M., Leonhardt, H. & Cardoso, M. C., DNA labeling in living cells. Cytometry A 67, 45-52 (2005)]) was added to cells to a final concentration of 1 μM, and incubated at room temperature for 30 minutes; media was discarded and cells were gently washed twice with 1×PBS. 100 uL 1×PBS was then added to each chamber for further observation for confocal microscopy. DIC, DRAQ5 (staining cell nucleus), and FITC images were collected on the ZEISS LSM-510 META Confocal Microscope.

Figure 2B:
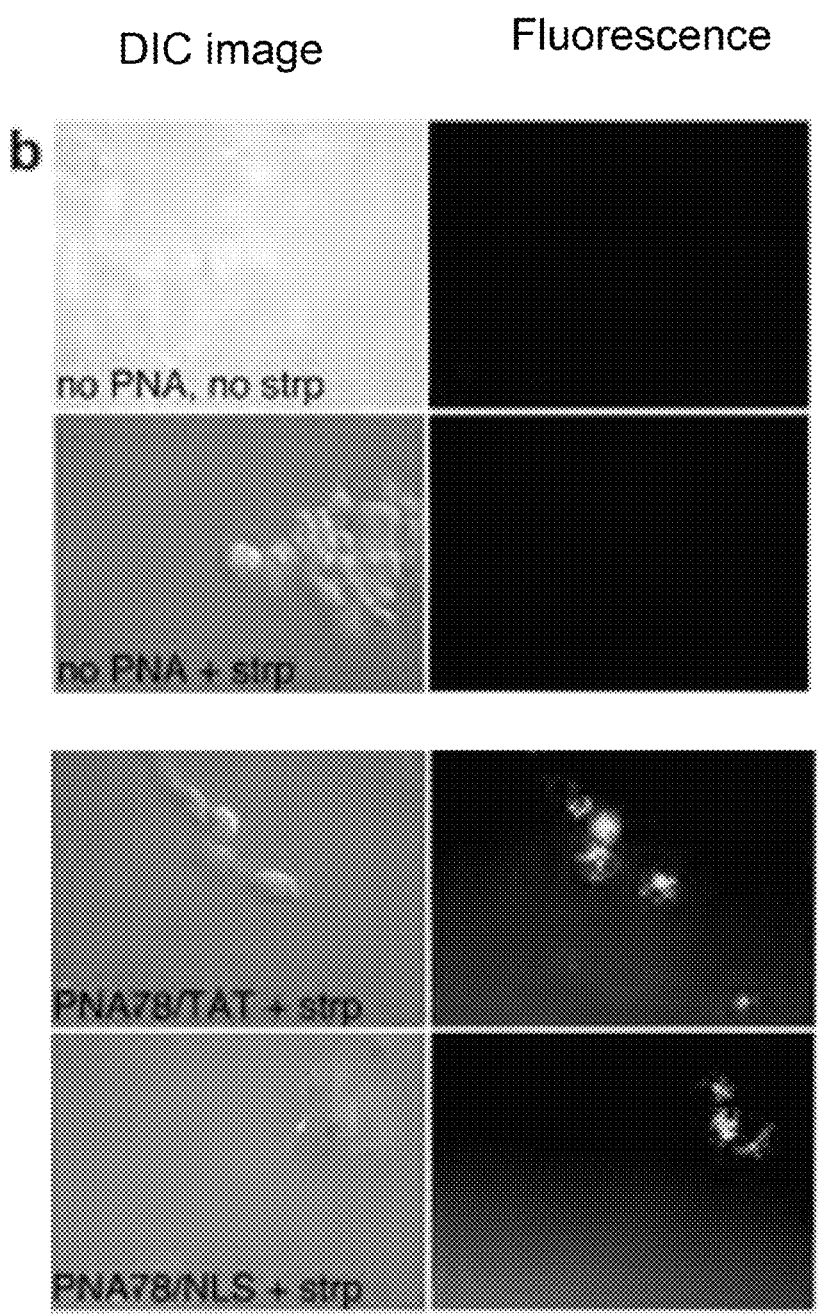
FIG. 2(b) depicts fluorescent microscopy showing uptake of PNA78/TAT or PNA78/NLS (at final concentrations of 10 uM) by COS7 cells. Live cell (unfixed) images: left, DIC (brightfield) image; right, fluorescence (FITC) indicating positive PNA signals.

To help more easily detect subcellular localization of the PNA78/TAT or PNA78/NLS, initial tests were performed with COS7 cells (FIG. 2(b)). The results showed that, after only a 2-hour incubation, the PNA/TAT molecules not only entered the cells but also proceeded to the nucleus.

Figure 2C:
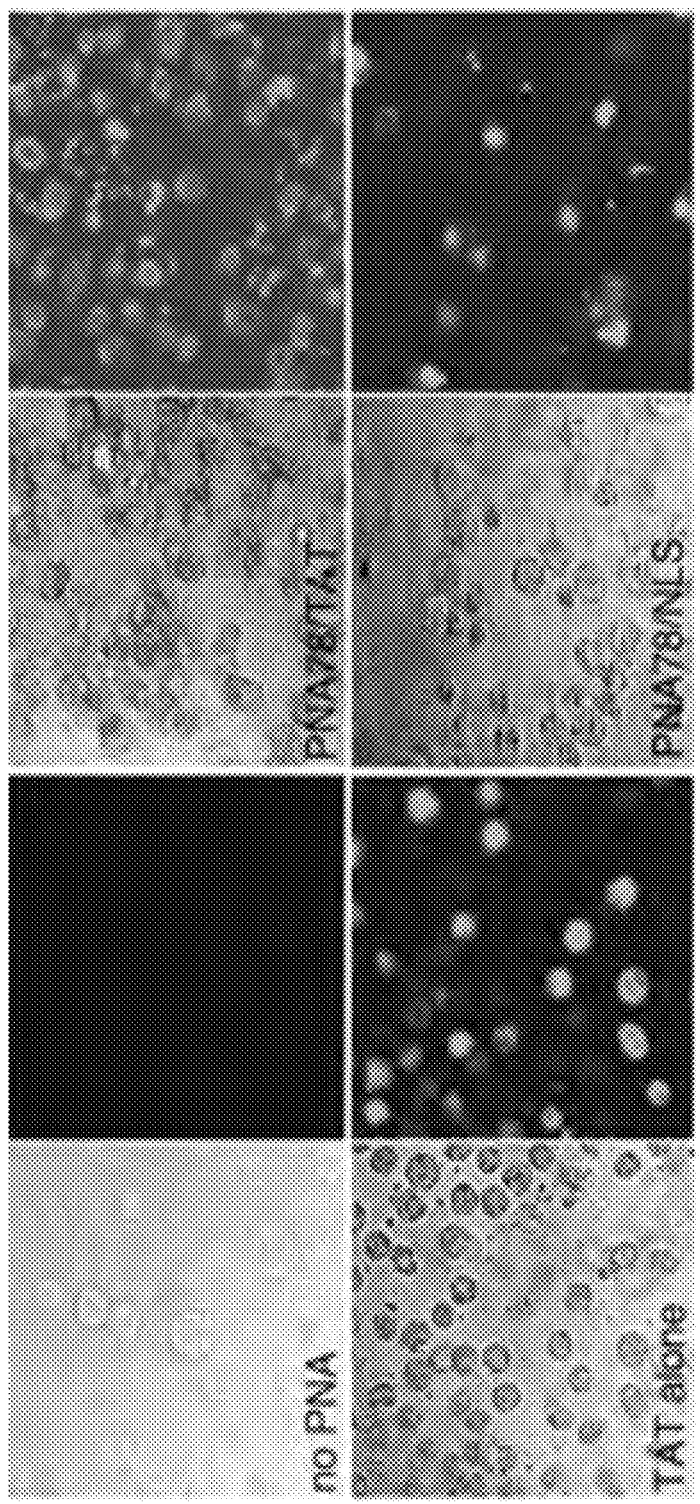
FIG. 2(c) depicts confocal microscopy showing uptake of PNA78/TAT, PNA78/NLS, or 'TAT alone' (positive control) (all at a final concentration of 10 uM) into K562 cells that had been attached to poly-L-lysine coated slides. Live cell (unfixed) images: left, DIC image; right, green fluorescence (FITC) indicating positive PNA signals.

This procedure was then performed with the K562 erythroid cell line. However, because these normally grow in suspension, they were first attached to poly-L-lysine coated plates to enable easier visualization of the signal localization. As before, the PNA molecules were directly added to K562 cells in serum-free media along with streptavidin-FITC, and their localization was monitored by confocal microscopy without fixation (FIG. 2(c)). Easily visible bright positive signals were present in the cell nucleus both in PNA78/TAT and PNA78/NLS treated cells; however, the distribution and efficiency was significantly higher in PNA78/TAT treated cells. These results were highly encouraging, as efficiencies of cell entry were always greater than 50% and sometimes approached 95%. Based on these experiments, it was concluded that PNA molecules attached to a TAT sequence at its 3' end provide a consistent and efficient means of directing the PNA cargo to the nucleus.

Example 5

Figure 3A:
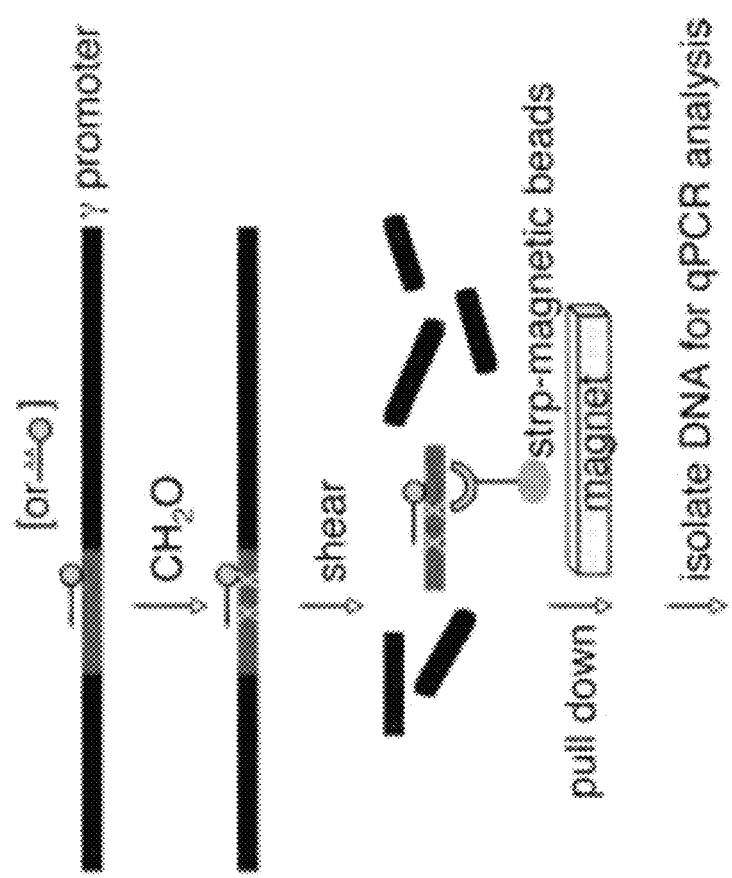
FIG. 3(a) depicts steps of modified chromatin association assay using streptavidin-conjugated magnetic beads and the magnetic particle concentrator. During the actual experiment, a portion of the treated cells were simultaneously analyzed for PNA uptake by confocal microscopy.

In Vivo Target Binding of PNA78 in K562 Cells Using a Novel Chromatin Association Assay To determine whether PNA78 can interact with its target site in vivo, a modification of the chromatin immunoprecipitation assay was developed. This assay took advantage of the biotin label already incorporated into the 5' end of the PNA molecule and was based on the standard ChIP assay whereby streptavidin-magnetic beads (rather than antibodies) are used to pull-down the PNA78/DNA complex after the normal series of PNA/cell incubation, formaldehyde cross-linking, and chromosomal DNA shearing steps (FIG. 3(a)). Along with the "no addition" negative control, a variant of PNA78 that contain two point mutations (MUT PNA78) was synthesized and used it as an additional negative control along with a "TAT alone" control.

As the PNA/DNA interaction is not protein-based, a novel chromatin association assay that does not utilize antibodies, but rather relies on the biotin moiety in the PNA molecule as a tag for its isolation with streptavidin beads was developed. This assay incorporates elements of chromatin [see Siatecka, M., Xue, L. & Bieker, J. J., Sumoylation of EKLF promotes transcriptional repression and is involved in inhibition of megakaryopoiesis, Mol Cell Biol 27, 8547-8560 (2007)] and biotinylated protein [see Viens, A., Mechold, U., Lehrmann, H., Harel-Bellan, A. & Ogryzko, V., Use of protein biotinylation in vivo for chromatin immunoprecipitation. Anal Biochem 325, 68-76 (2004)] immunoprecipitation protocols. PNA 78/TAT or mutant (MUT) PNA 78/TAT were added to $10^7$ K562 cells to a final concentration of 10 µM. After 36 hours, a portion of the cells were analyzed and quantified for PNA incorporation efficiency by confocal analysis of live cells (as above), and the rest were harvested and cross-linked with 0.4% formaldehyde (Fisher Scientific, F79-500) for 10 minutes in room temperature then quenched by addition of glycine in the final concentration of 0.125 M for another 10 minutes. Cells were then washed twice in cold PBS, pelleted at 3000 rpm and suspended in 500 µL SDS buffer (50 mM Tris at pH 8.1, 0.5% SDS, 100 mM NaCl, 5 mM EDTA and protease inhibitors) and incubated 10 minutes on ice. Cells were then pelleted by centrifugation and resuspended in 1.6 mL IP buffer (0.3% SDS, 1.1% Triton X-100, 1.2 mM EDTA, 16.7 mM Tris pH8.1, 167 mM NaCl and protease inhibitor) and disrupted by sonication (power 4, 21% duty, 30 seconds each time for 10 times with 2 minute-pulse on ice) yielding genomic DNA fragments of ~1000 bp. Lysates were collected at 13000 rpm for 30 minutes and diluted 1:5 in IP buffer and incubated with 40 uL streptavidin MagneSphere Paramagnetic particles (Promega Cat #Z5481) for 2 hours. Magnetic Particle Concentrator (Dynal MPCS) was used to collect the MagneSphere and its bound material, which was washed five times with LiCl buffer (100 mM Tris pH8.0, 500 mM LiCl, 1% NP-40, 1% deoxycholic acid). Beads were finally resuspended in 150 µL 300 mM NaCl at 65° C. overnight followed by incubation at 42° C. for 2 hours with 20 µL protein kinase K (20 mg/mL). DNA was purified by phenol/chloroform extraction and resuspended in 20 µL ddH2O.

Figure 3B:
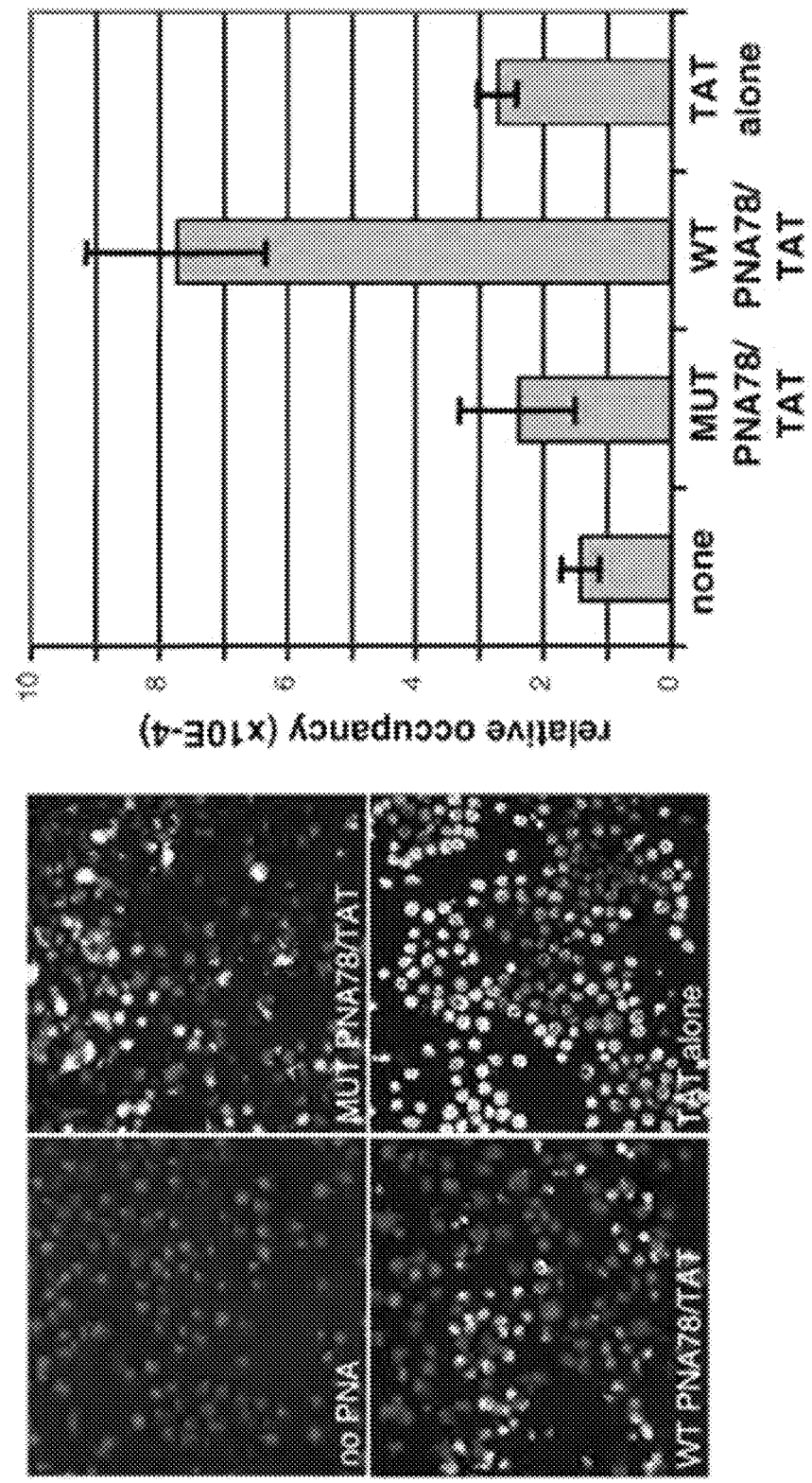
FIG. 3(b), left panel, depicts a confocal image showing nuclear-entering efficiency of WT PNA78/TAT and MUT PNA78/TAT. 'No PNA' and 'TAT alone' were included as negative and positive controls. DRAQ5 was used as a nuclear stain for live (unfixed) cells.

After 16 hours of incubation of K562 cells, any formed PNA-chromatin complex was cross-linked and cells were disrupted and chromatin was sheared by sonication. Since all the PNAs were linked to biotin, the complex formed between PNA and the bound chromatin was pulled down and isolated by binding to streptavidin-conjugated magnetic beads. The DNA was purified for sequence identification by quantitative PCR. To more precisely quantitate the extent of PNA entry into the nucleus, a portion of the cells from each treatment was collected, stained with the DRAQ5 live-cell nuclear stain, attached to chamber-slides, and inspected under confocal microscopy to compare PNA and TAT nuclear entry efficiency. The results (FIG. 3(b)) show that while the two PNAs and TAT were taken up by cells with a similar efficiency, only wild-type (WT) PNA78 interacted with its target sequence within the γ-globin promoter to a level greater than the non-specific MUT PNA78 and TAT alone, which had values that are not higher than the 'no addition' control. This data confirmed that WT PNA78 has target binding specificity with the endogenous γ-globin promoter in vivo.

Example 6

Figure 4C:
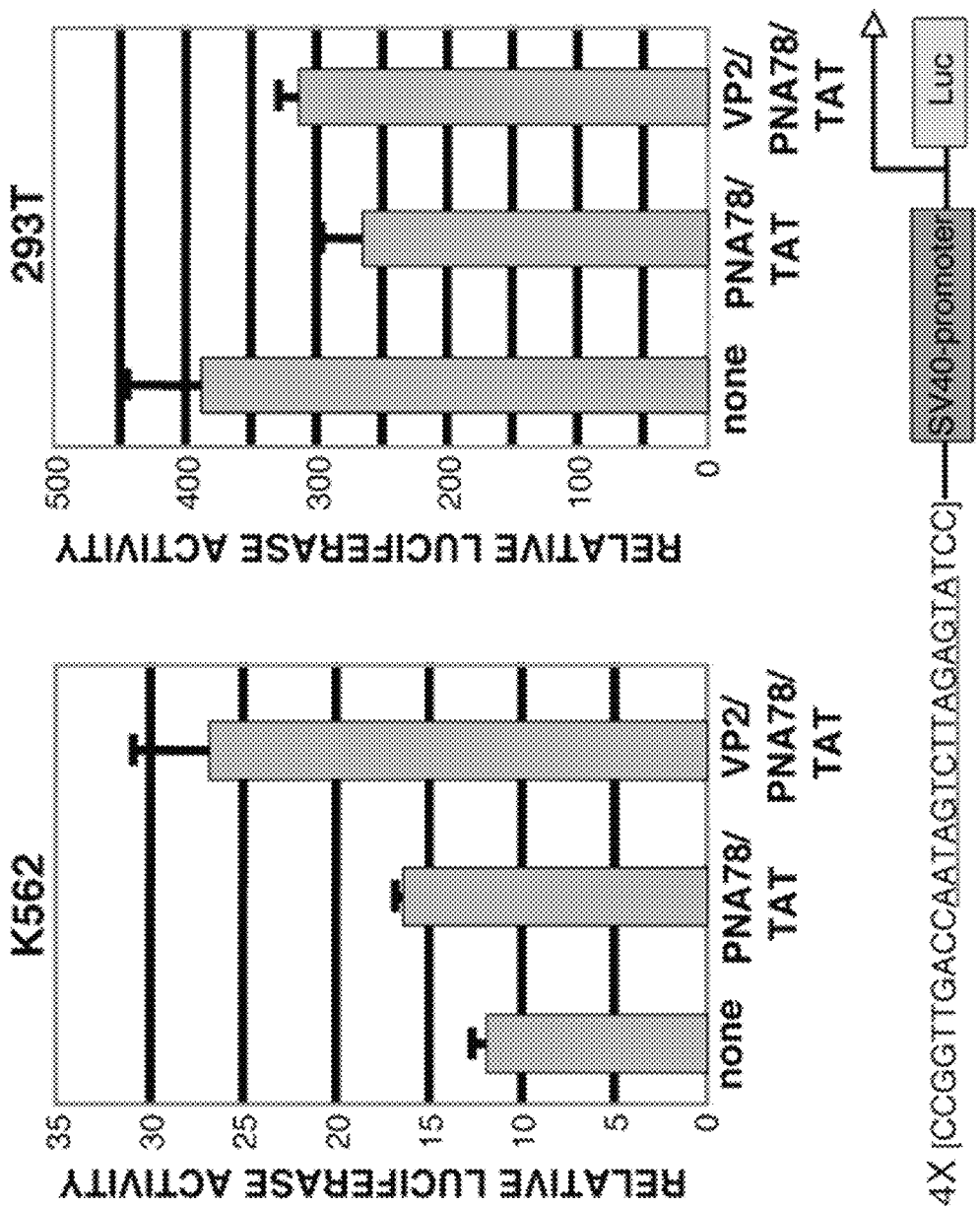
In FIG. 4(c), a reporter plasmid bearing 4 repeats of the PNA78 target sequence and the minimal SV40 promoter upstream of luciferase gene (schematic shown below; PNA78 sequence is underlined) was transfected into either K562 or 293T cells and followed by exposure to PNA78/TAT, VP2/PNA78/TAT, or buffer. Values were normalized to a cotransfected Renilla control.

PNA Conjugated with a Minimum Activation Domain (AD) Alters Transcriptional Activity in K562 Cells The above experiments established that WT PNA78 is able to enter the cell nucleus and bind to its target sequence at the γ-globin promoter site in vivo. To assess whether WT PNA78 can alter transcription, a transient assay was used. A γ-globin luciferase reporter was transfected into K562 cells followed by exposure of the cells to TAT, PNA78/NLS, or PNA78/TAT. Although TAT alone had no effect on the basal activity of the reporter, PNA78/NLS exerted a mild, and PNA78/TAT a stronger, superactivation effect on its expression (FIG. 4(a)). As predicted, mutation of the PNA78 target site on the γ-promoter negated its ability to be superactivated by PNA78/TAT. However, the basal activity of the γ-promoter was dramatically impaired (FIG. 4(b)), suggesting that the DNA sequence complementary to PNA78 encodes an important γ-promoter element.

It was then examined whether the potential of WT PNA78 to alter transcriptional activity in vivo can be enhanced by linking it to a transcriptional activator motif. The VP2 minimal activation domain (AD) was chosen for the first set of experiments. The VP2 minimal activation domain is a highly acidic 16 amino acid sequence (MLGDFDLDMLGDFDLD; SEQ ID NO: 30) derived from the herpes simplex virus C-terminus transactivation domain of VP16. [See Ansari, A. Z., Mapp, A. K., Nguyen, D. H., Dervan, P. B. & Ptashne, M., Towards a minimal motif for artificial transcriptional activators. Chem Biol 8, 583-592 (2001).] VP2 is a very potent artificial transactivator in vitro when linked to a DNA-binding protein domain. [See Arora, P. S., Ansari, A. Z., Best, T. P., Ptashne, M. & Dervan, P. B., Design of artificial transcriptional activators with rigid poly-L-proline linkers. J Am Chem Soc 124, 13067-13071 (2002).] This amino acid sequence was linked to PNA78/TAT at its 5' domain to yield VP2/PNA78/TAT. This molecule retains the biotin label at the beginning of the VP2 sequence for monitoring purposes. The ability to superactivate the γ-globin/luciferase reporter in transfected K562 cells was tested, but there was little effect beyond that seen with PNA78/TAT. Then an artificial luciferase reporter plasmid was constructed with four tandem repeats of PNA78 target sequence upstream of the minimal SV40 promoter and its activity in erythroid K562 cell line and in the non-erythroid 293T cell line (ATCC deposit number CRL11268) was tested. Three hours post-transfection, PNA78/TAT or VP2/PNA78/TAT were added to cells in serum-free media. A portion of the cells were also inspected under confocal microscopy after streptavidin-FITC treatment to normalize PNA uptake efficiency. It was found that the luciferase activity increased by 2.3-fold in cells treated with VP2/PNA78/TAT compared to non-treated cells, a stronger effect than seen with PNA78/TAT and not observed at all in 293T cells (FIG. 4(c)). This demonstrated that the attachment of a transactivation domain to the PNA78/TAT molecule enhances its ability to activate transcription in the K562 fetal-like erythroid environment.

Plasmids

The γ-globin reporter contained a 1.5 Kb Human HS2 fragment upstream of the −299 to +37 human γ-globin promoter in Promega's (Madison, Wis.) pGL2 Basic plasmid. [See Caterina, J. J., Donze, D., Sun, C. W., Ciavatta, D. J. & Townes, T. M., Cloning and functional characterization of LCR-F1: a bZIP transcription factor that activates erythroid-specific, human globin gene expression. Nucleic Acids Res 22, 2383-2391 (1994).] A modified pGL2-promoter vector from Promega with one or four copies of the PNA78 target sequence (CCGGTTGACCAATAGTCTTAGAGTATCC; SEQ ID NO: 40) upstream of the minimal SV40 promoter was also generated by synthesis of the oligonucleotide followed by ligation into the XmaI and XhoI sites of the vector.

Transfection

Transfection of K562 cells was performed using the DMRIE lipofection method (Gibco, Invitrogen, Carlsbad, Calif.). K562 cells were counted and $1 \times 10^5$ cells were resuspended in 0.1 mL OPTI-MEM in a 12-well plate (BD Falcon, Franklin Lakes, N.J.). Experiments were all done in triplicates. 1.5 ng Renilla plasmid (Promega Corporation. Madison, Wis.) and 0.5 µg reporter construct were added to each well. After 2 hours of transfection, PNAs were added to a final concentration of 10 µM. 2 hours later, 1 ml RPMI and a final concentration of 10% FBS were added to each well. This was followed by incubation at 37° C. for 36 hours.

Luciferase Reporter Assay 36 hours after PNA addition, K562 cells were collected by centrifugation at 2500 rpm. Media was discarded and cells were washed once with 1×PBS and resuspended in 250 µL 1× passive lysis buffer (PLB) (Promega). Tubes that contained cells were put on a rocker platform for 10 minutes at room temperature. Cells were then centrifuged at 13000 rpm and resuspended in 200 µL 1×PLB, loaded on a 96 well plate and further analyzed with a Turner Biosystem Microplate Luminometer. [See Siatecka, M., Xue, L. & Bieker, J. J., Sumoylation of EKLF promotes transcriptional repression and is involved in inhibition of megakaryopoiesis. Mol Cell Biol 27, 8547-8560 (2007).] Luciferase values were divided by the Renilla value from the same sample after it had been divided by 1000. To minimize the differences in between loading, each sample was loaded in three different wells and the average of three was calculated.

Example 7

PNA-AD Changes the Globin Expression Pattern in Mouse Bone Marrow Cells

The above tests had been directed at a non-chromatinized DNA target promoter that is already highly active prior to any treatment. It was thus important to test whether the PNA constructs can activate a dormant γ-globin promoter in an erythroid cell that has already switched off its expression in favor of adult β-globin. To test this, a line of mouse bone marrow cells engineered to carry a yeast artificial chromosome that contains the complete human β-like globin locus (β-YAC) was used. [See Blau, C. A. et al. γ-Globin gene expression in chemical inducer of dimerization (CID)-dependent multipotential cells established from human β-globin locus yeast artificial chromosome (β-YAC) transgenic mice. J Biol Chem 280, 36642-36647 (2005).] These adult bone marrow cells have shut off human fetal γ-globin expression and solely express human adult β-globin (in addition to the endogenous mouse adult β-globin). The large β-YAC is properly controlled during murine development in that human γ-globin is expressed in the yolk sac but switches expression to human β-globin at the same time as the endogenous mouse β-globin. [See Peterson, K. R. et al., Use of yeast artificial chromosomes (YACs) for studying control of gene expression: correct regulation of the genes of a human beta-globin locus YAC following transfer to mouse erythroleukemia cell lines. Proc Natl Acad Sci USA 90, 11207-11211 (1993).] The fact that these cells are responsive to a known γ-globin inducer (5-azacytidine) makes them particularly clinically relevant. [See Blau, C. A. et al., supra.]

To investigate whether PNA78 attached to an activation domain can reactivate the endogenous γ-globin gene in these mouse bone marrow cells, its expression was compared in cells treated with two different minimal AD attached to WT PNA78: VP2, and another minimal activation domain, ATF14 (CGSDALDDFDLDML; SEQ ID NO: 27), which is also highly acidic and has been shown to be a promising candidate as an artificial transcription factor in vitro and in vivo. [See Qiu, C., Olivier, E. N., Velho, M. & Bouhassira, E. E., Globin switches in yolk sac-like primitive and fetal-like definitive red blood cells produced from human embryonic stem cells. Blood 111, 2400-2408 (2008).] In addition, to address whether the relative position of the AD and biotin may affect its transactivational ability or even the ability to visually monitor its presence, two PNA chimeric variants with ATF14 were generated: one (analogous to PNA/VP2 construct) with the biotin at the 5' end (amino terminus) of the molecule (Bio-ATF/PNA78/TAT), and one with the biotin inserted between ATF and PNA78 (ATF-Bio/PNA78/TAT).

Figure 5B:
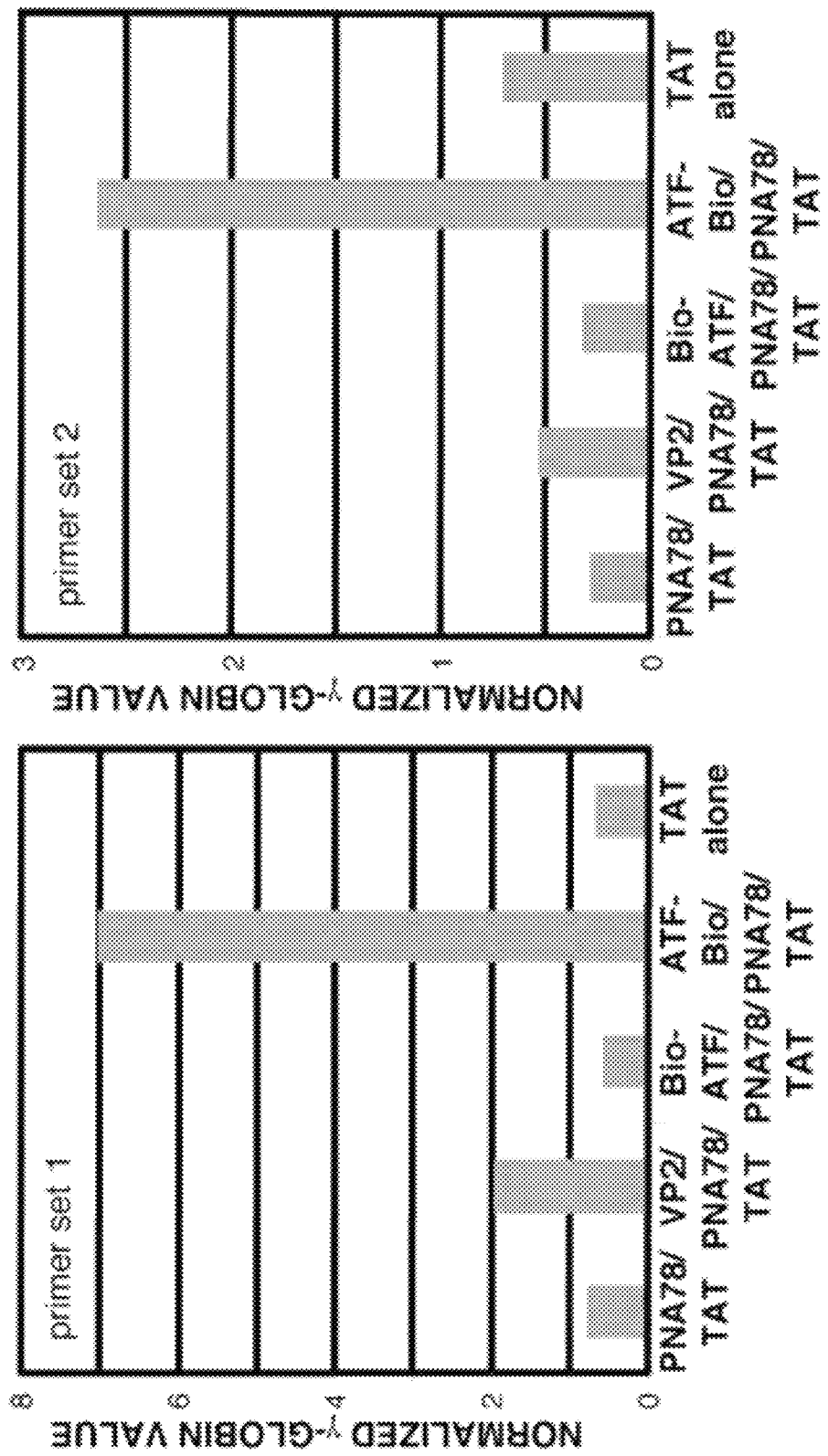
FIG. 5(b) shows an expression profile of γ globin levels in MBC-βYAC cells in (a) analyzed by quantitative RT-PCR with 2 sets of primers as described in Methods. Each experiment is the average of triplicate sample analyses.
Figure 5C:
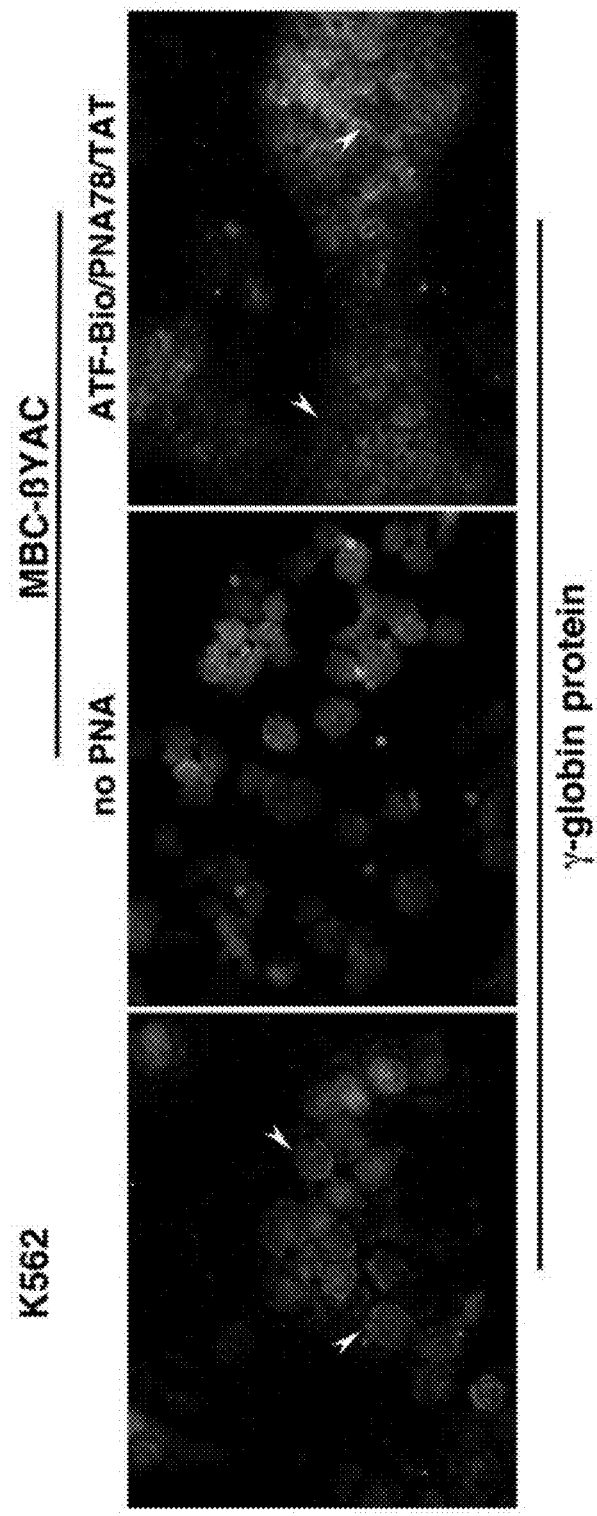
In FIG. 5(c) MBC-βYAC cells were treated with buffer ('no PNA') or ATF-Bio/PNA78/TAT and analyzed by confocal microscopy 36 hours later by fixing and staining with DAPI (blue) and an anti-human γ-globin protein antibody linked to Alexa 568 (red). K562 cells were also stained and served as a positive control for γ-globin protein detection (arrowheads).
Figure 6:
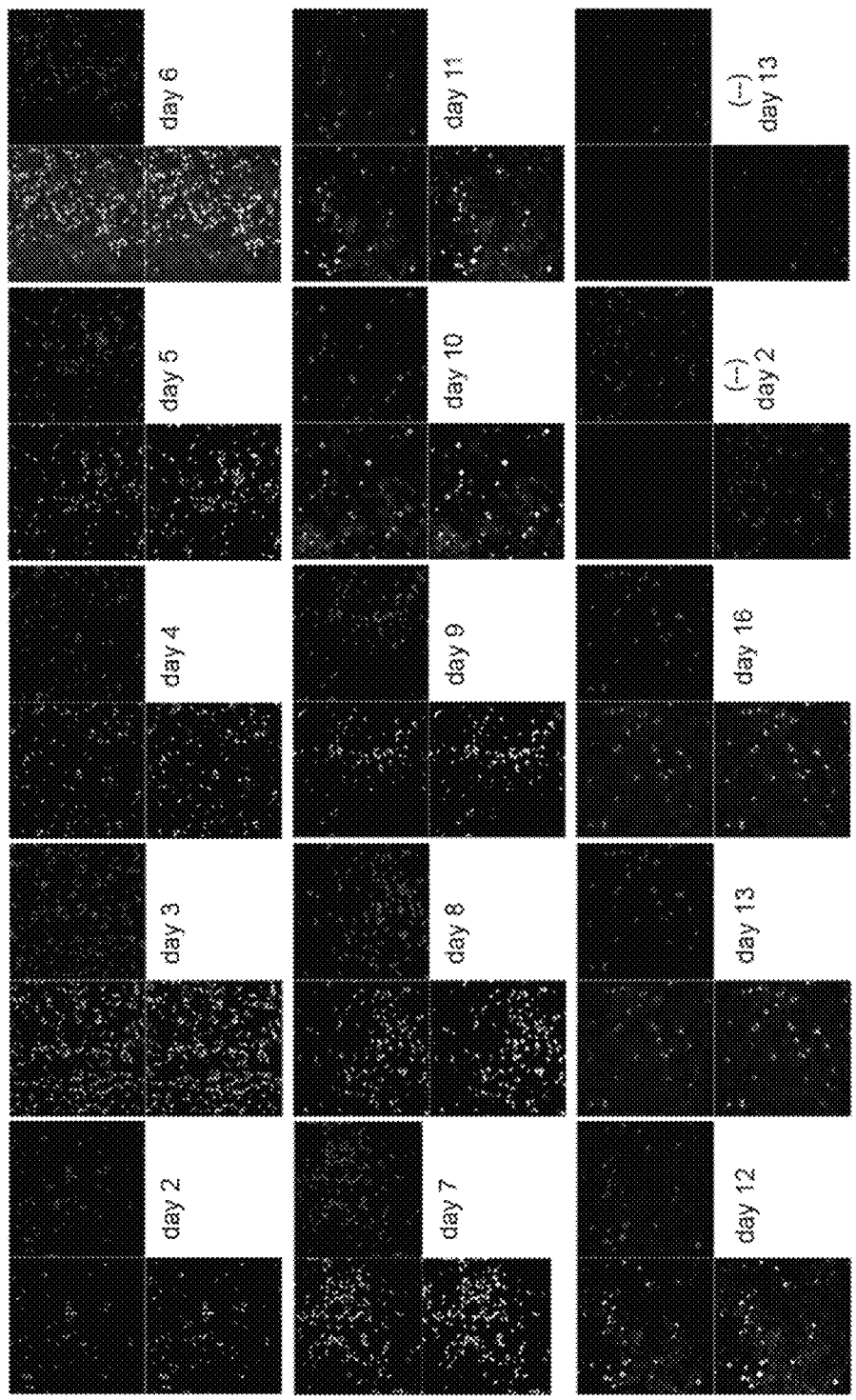
FIG. 6 shows persistence of ATF-Bio/PNA78/TAT after introduction into cells. In the figure, a series of confocal images are shown of K562 cells that have been exposed to ATF-Bio/PNA78/TAT at day 0. Visualization of PNA was with streptavidin-FITC, and DRAQ5 was used as a nuclear stain for live (unfixed) cells. (--) are cells that had not been exposed to PNA. In some cases the same field was monitored on successive days. Each panel contains: top left, fluorescence (FITC) positive PNA signal; top right, DRAQ5 nuclear signal; bottom left, merged DRAQ5/FITC signal.

After treatment, cells were harvested and mRNA was extracted for reverse transcriptase (RT)-quantitative polymerase chain reaction (qPCR) using two different sets of published primers that recognize sequences within the γ-globin gene. [See Blau, C. A. et al., supra and Qiu, C., et al., supra]. The results (FIG. 5(a) and FIG. 5(b)) show that although VP2/PNA78/TAT increased γ-globin levels about 2-fold, ATF-Bio/PNA78/TAT is the most effective at increasing γ-globin expression, attaining a 7-fold increase in comparison to cells treated with PNA78/TAT alone. It is of interest that placement of the biotin is critical, as placing it at the extreme 5' end (Bio-ATF/PNA78/TAT) precluded its ability to activate γ-globin expression. It was also found that γ-globin protein, which is not detectable in the untreated cells, is expressed in ATF-Bio/PNA78/TAT cells in the cytoplasm at levels approaching that seen in uninduced K562 cells (FIG. 5(c)). From these studies it was concluded that it is possible to design a chimeric molecule containing peptide nucleic acids linked to cell entry/localization and activation amino acid sequences that can bind and directly activate transcription of a specific endogenous target gene in the cell.

Figure 11A:
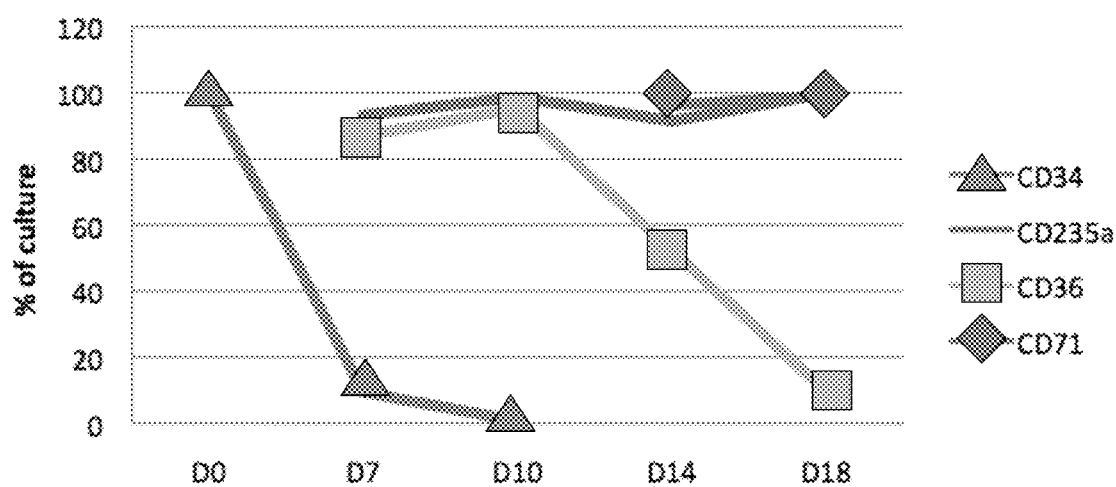
FIG. 11(a) is a line graph showing the percent of the cell culture expressing the cell surface markers CD34, CD235a, CD36, and CD71 at the indicated time points (days, "D").
Figure 11B:
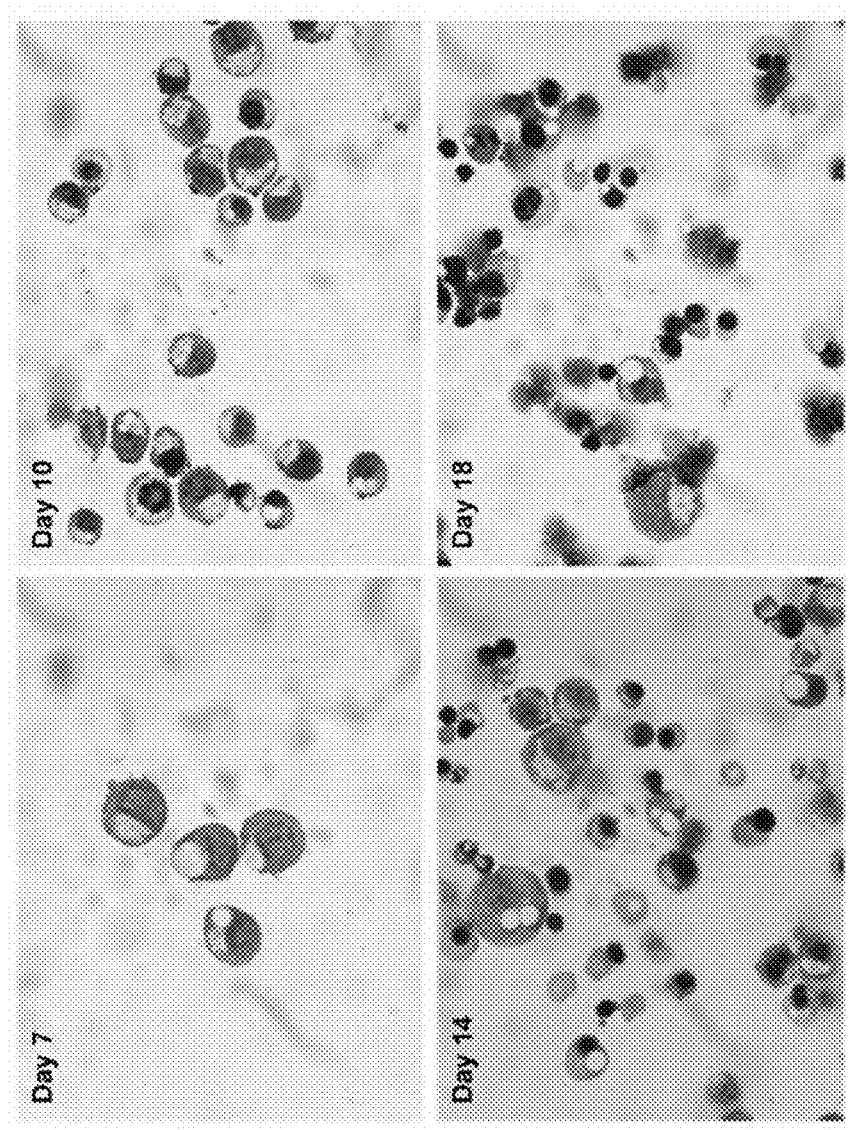
FIG. 11(b) contains images showing the morphological (Giemsa) analyses performed on human peripheral blood CD34+ samples removed at the indicated day of culture. The progressive changes toward a more terminally differentiated state such as later stage erythroblasts are indicated by arrows and mature enucleated red cells are indicated by asterisks.
Figure 12A:
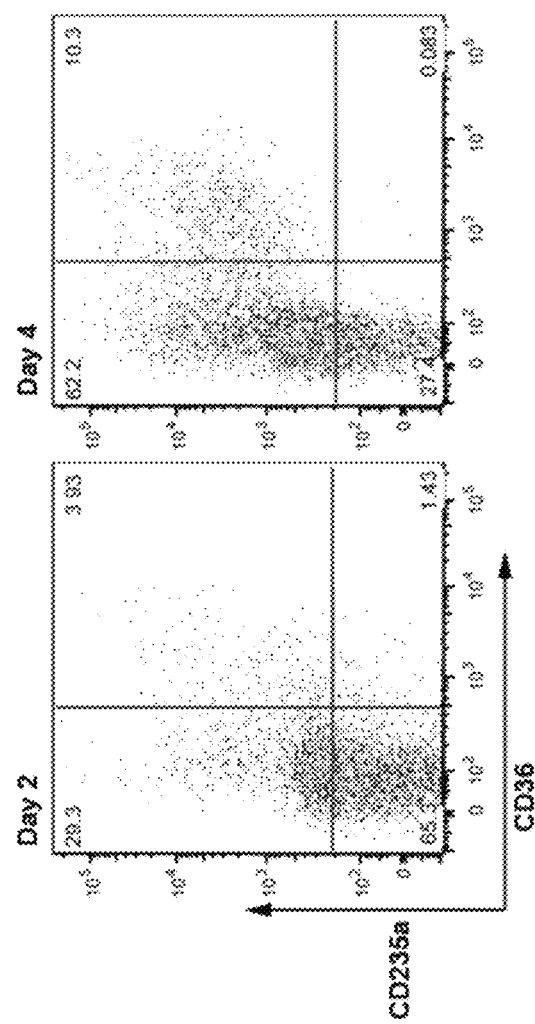
FIG. 12(a) contains dot plots showing flow cytometric profiles of CD36 and CD235a expression in human peripheral blood (H-BP) samples at Day 2 and Day 4 of incubation in SCF/Epo, showing increases in their expression during culture.
Figure 12B:
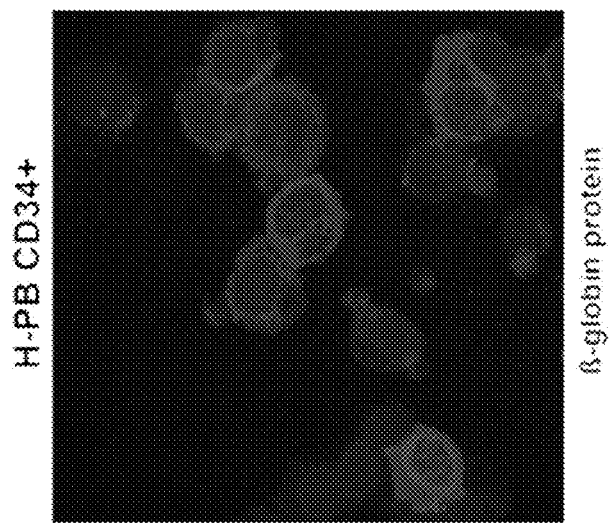
FIG. 12(b) is a fluorescent image showing beta globin expression in H-PB CD34+ cells and FIG. 12(c) is an expression analysis by semi-quantitative RT-PCR of β-globin mRNA in H-PB cells on Day 0, 2, 4, 5, and 7 as indicated.
Figure 12C:
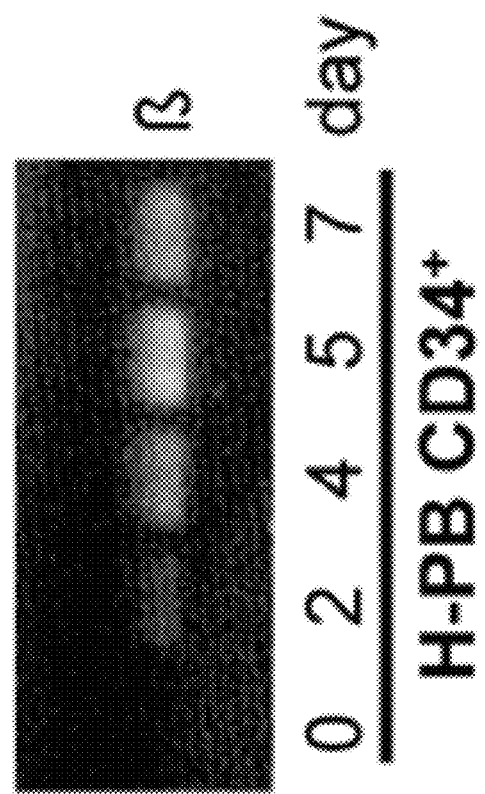

The ability of the chimeric PNA molecule's ability to stimulate γ-globin expression was further tested in human mobilized peripheral blood CD34+ cells. When incubated in a two-step serum-free culture system, these progenitors differentiated to phenotypically and morphologically mature erythroid cells (FIG. 11(a), FIG. 11(b)). Changes in cell surface expression were already apparent between days 2-4 of culture (FIG. 12(a)), and the onset of adult β-globin RNA and protein expression begins by day 2 (FIG. 12(b), FIG. 12(c)). As a result, peripheral blood CD34+ cells cultured for two days were used for further testing.

Figure 13A:
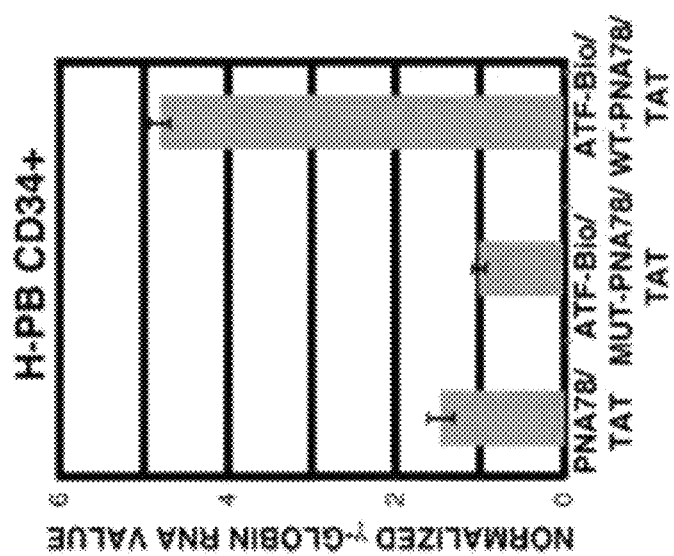
FIG. 13(a) is a bar graph showing the mRNA level of γ globin in cultured CD34+ cells 16 hours after treatment with PNA78/TAT, ATF-Bio/MUT-PNA78/TAT, or ATF-Bio/WT-PNA78/TAT. Analysis of triplicates was performed by quantitative RT-PCR (*p<0.005).
Figure 13B:
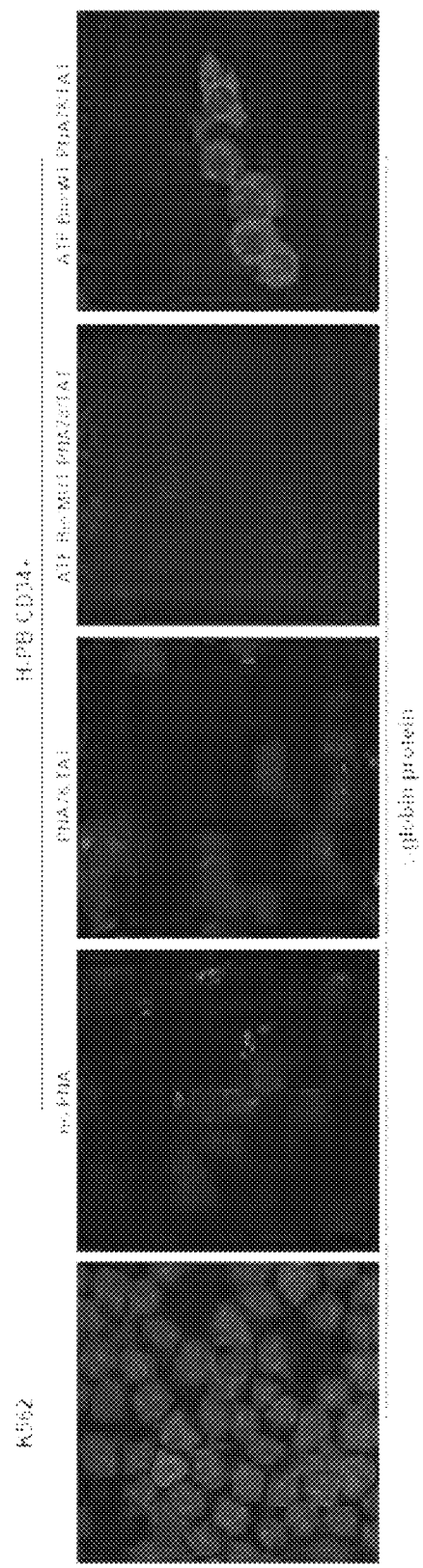
FIG. 13(b) contains images showing immunostaining and analysis by confocal microscopy of γ globin protein in cultured CD34+ cells from the same experiment as in FIG. 13(a), performed after treatment with buffer ('no PNA') or chimeric PNA78 molecules. K562 cells served as a positive control.
Figure 13C:
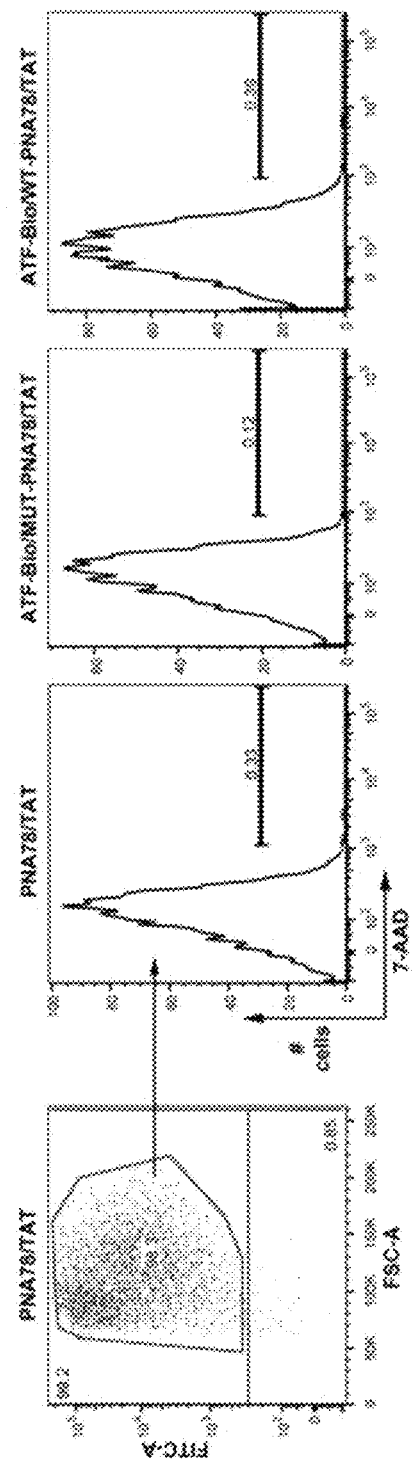
FIG. 13(c) contains dot plots and histograms from toxicity analysis by flow cytometry of cultured CD34+ cells after PNA treatment. The effectiveness of PNA78 entry was monitored with streptavidin-FITC.
Figure 14:
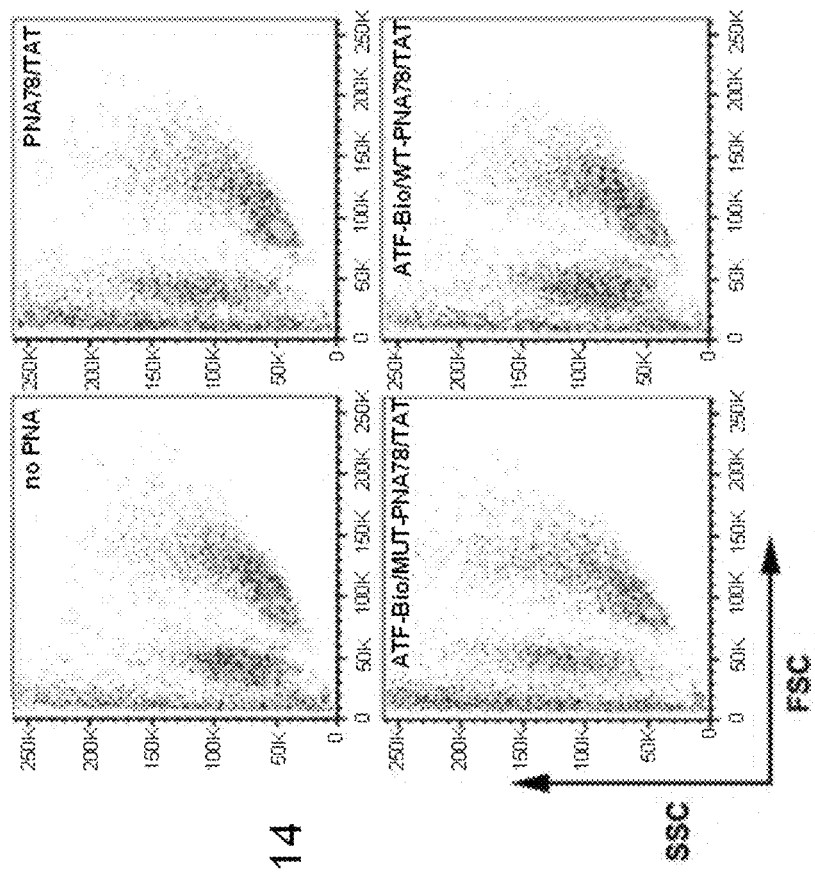
FIG. 14 is an expression profile of erythroid markers in human peripheral blood CD34+ cells after PNA treatment. Human peripheral blood (H-PB) CD34+ cells from the same experiment as in FIG. 8 (day 2 of culture) were analyzed by flow cytometry 24 hours after treatment with buffer ('no PNA'), PNA78/TAT, ATF-Bio/MUT-PNA78/TAT, or ATF-Bio/WT-PNA78/TAT.
Figure 14:
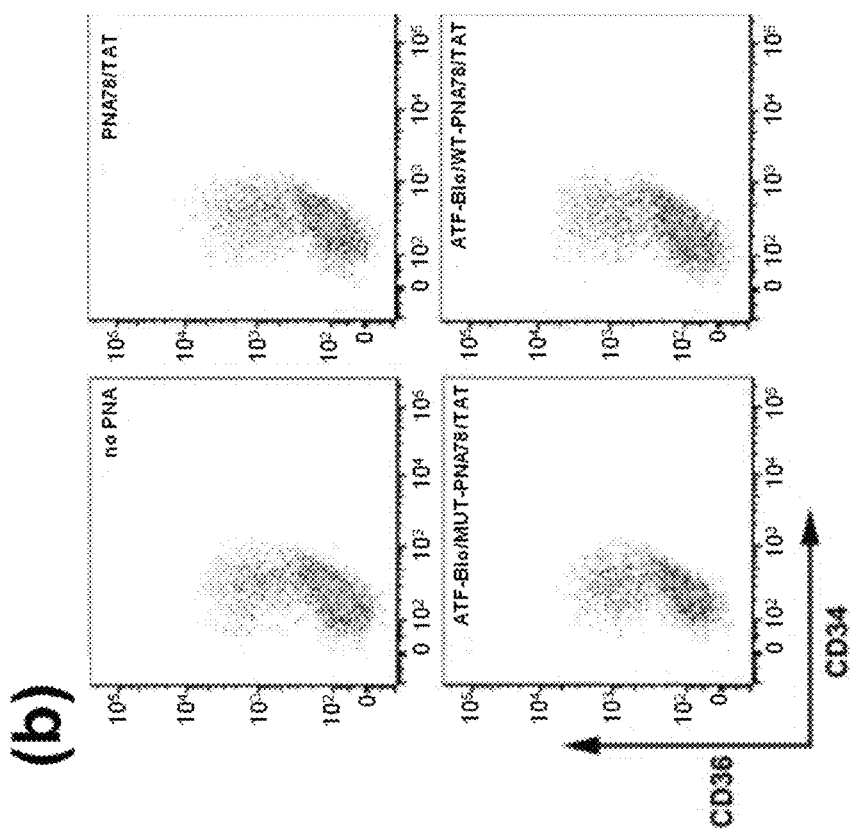
Figure 14:
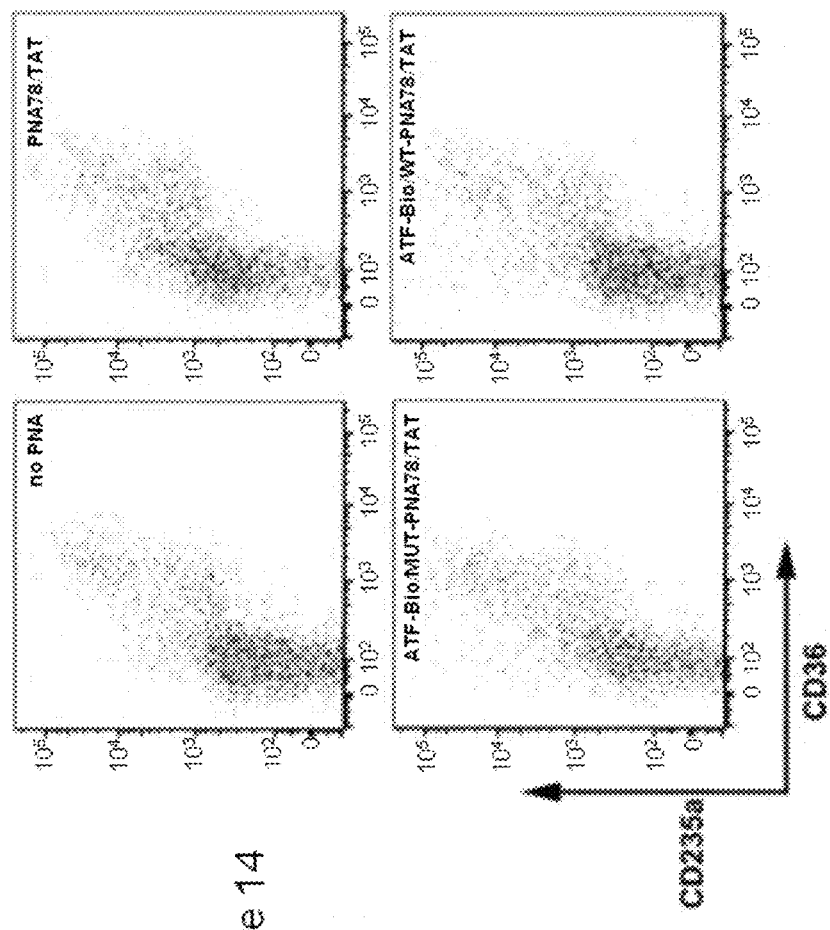

A mismatched PNA78 variant (ATF-Bio/MUT-PNA78/TAT) was used that was designed based on MUT-PNA as an additional negative control. Purified CD34+ cells were cultured, treated at the end of day 2 with the various PNA chimeras or with no PNA, and harvested 16 hours later for analysis. The results show that only cells treated with ATF-Bio/WT-PNA78/TAT increase γ-globin expression (by almost 5-fold compared to untreated cells) (FIG. 13(a)), and that this leads to γ-globin protein accumulation solely in those cells (FIG. 13(b)). Visual analysis of ≥100 cells per field from the same experiment indicates that 22% of cells treated with ATF-Bio/WT-PNA78/TAT were positive; all other samples were 0% positive (FIG. 13(b)). Use of a novel flow cytometric analysis of streptavidin-FITC-positive (i.e., PNA-positive) cells not only demonstrated a high level of PNA incorporation into the cultured CD34+ cells, but also confirmed that cell death caused by PNA (measured by dual monitoring of FITC+/7-AAD+) was always below 0.5% (FIG. 13(c)). In FIG. 13(c), the percent dead cells (7-AAD-positive) among all PNA-positive cells (>98% FITC+ as boxed in the PNA78/TAT example on the left) is indicated above the 7-AAD gate and was no higher than untreated cells. In FIG. 13(c), FITC+/7-AAD+ (i.e., percent dead cell) results are also shown for CD34+ cells treated with ATF-Bio/MUT-PNA78/TAT or ATF-Bio/WT-PNA78/TAT. Expression profiles of phenotypic markers (CD34, CD36, CD235a, and CD71) were unaltered as well (FIGS. 14(a)-(c)), demonstrating that there was no erythroid differentiation abnormality caused by PNA treatment. As shown in FIGS. 14(a)-14(c), all cells has similar forward scatter ("FSC") and side scatter ("SSC") profiles (FIG. 14(a)) and expressed the same level of CD34, CD36, and CD235a markers (FIG. 14(b)) even after exposure to the different PNA78 variants. In a separate experiment, H-PB cells from day 4 of culture were analyzed by flow cytometry 24 hours after treatment and show the same level of CD235a and CD71 expression irrespective of variant PNA78 exposure (FIG. 14(c)).

Quantitative PCR Analysis

One microliter of DNA was used in 20 μl of quantitative PCR reaction using a Quantitect SYBR Green PCR kit from Qiagen (Valenica, Calif.) and the presence of γ-globin promoter sequences was quantified with an ABI PRISM 7900HT and SDS software. [See Lohmann, F. & Bieker, J. J. Activation of Eklf expression during hematopoiesis by Gata2 and Smad5 prior to erythroid commitment. Development 135, 2071-2082 (2008).] Each reaction was performed in triplicate. Primers used for the analysis were: Gamma-promo-fwd: AGCCTTGACAAGGCAAACTTGA (SEQ ID NO: 31); Gamma-promo-rev: CCCTGGCCTCACTGGATACTCT (SEQ ID NO: 32).

Quantitative Globin Expression Analysis

Total RNA from β-YAC MBCs were isolated with a RNeasy micro kit (Qiagen) following the manufacturer's instructions. RNA concentrations were quantified using a Nanodrop. Reverse transcription of RNA was performed with Promega's Reverse Transcription System and expression levels were quantified using a Quantitect SYBR Green PCR kit from Qiagen in conjunction with an ABI PRISM 7900HT and SDS software [see Lohmann, F. & Bieker, J. J. supra] Q-PCR results for globin expression were normalized by 2−[(Ct γ−Ct β)−(Ct γ [no PNA]−Ct β [noPNA])][see Livak, K. J. & Schmittgen, T. D., Analysis of relative gene expression data using real-time quantitative PCR and the 2(−Delta Delta C(T)) Method. Methods 25, 402-408 (2001)] divided by the PNA incorporation efficiency (determined from the live cell image data). Each reaction was performed in triplicate.

The PCR primer sequences were derived from two studies [see Blau, C. A. et al. and Qiu, C., Olivier, E. N., Velho, M. & Bouhassira, E. E. Globin switches in yolk sac-like primitive and fetal-like definitive red blood cells produced from human embryonic stem cells. Blood 111, 2400-2408 (2008)]: for globin expression in MBCs: (primer set 1) human gamma-globin forward: ACCGTTTGGCAATCCATTTC (SEQ ID NO: 33), reverse: TATTGCTTGCAGAATAAGCC (SEQ ID NO: 34); (primer set 2) human gamma-globin forward: GACCGTTTTGGCAATCCATTTC (SEQ ID NO: 35), reverse: TATTGCTTGCAGAATAAGCC (SEQ ID NO: 36). Both studies used the same set of human β-globin primers: forward: ACACAACTGTGTTCACTAGCAACCTCA (SEQ ID NO: 37), reverse: GGTTGCCCATAACAGCATCAGGAGT (SEQ ID NO: 38).

Immunofluorescent Detection of γ-Globin Protein

At 48 hours post-PNA treatment, 100K MBC-βYAC cells were collected and spun onto frosted slides (Fisher) in a Shandon Cytospin 2 centrifuge at 500 rpm for 5 minutes. All steps were carried out at room temperature except when indicated. Cells were fixed for 4 minutes in ice-cold acetone/methanol (1:1) on ice and rinsed twice with 2% BSA/PBS. Samples were then incubated with blocking solution (10% FCS, 0.05% NP40/PBS) for 30 minutes followed by a two-hour incubation with hemoglobin γ antibody (Santa Cruz Biotechnology, sc-21756) diluted 1:100 in blocking solution. Slides were washed 3× with 2% BSA, 0.05% NP40/PBS and then incubated with goat anti-mouse secondary antibody conjugated to Alexa 568 (Invitrogen) at a 1:50 dilution for one hour in a dark chamber. Slides were then washed 3× with 2% BSA/PBS with a final rinse in PBS and mounted with DAPI-containing Vectashield. DAPI and Alexa568 images were visualized on a Zeiss spinning disc confocal microscope (PerkinElmer).

PNA Persistence Test

30000 K562 cells were suspended in OPTI-MEM and attached to the bottom of a 8-well L-polylysine coated cover glass chamber slide (Nunc) and treated with ATF-Bio/PNA78/TAT in a final concentration of 10 uM and incubation at 37° C. 2 hours after PNA addition, Streptavidin-FITC was added to cells with a final concentration of 5 ug/mL followed by another 2 hours of incubation at 37° C. Cells were inspected every day after 48 hours post-PNA treatment under ZEISS LSM-510 META confocal microscopy. DRAQ5 was used to stain cell nucleus 30 minutes prior to each confocal observation. Images of DRAQ5 and FITC were collected and compared with data collected during previous days.

Human Erythroid Cell Culture

Erythroid cells were derived from adult human mobilized peripheral blood (H-PB) CD34+ cells (All Cells, LLC. Emerville, Calif., USA) in a two-step liquid culture system. In the first step, CD34+ cells were plated at a density of $0.5 \times 10^6$ cells/ml in expansion media consisting of Iscove's Modified Dulbeco Media (IMDM) supplemented with 1% penicillin/streptomycin, 1% L-Glutamine (Invitrogen, Grand Island, N.Y., USA), 20 mM B-merchaptoethanol, 1% bovine serum albumin (BSA) Fraction V (Sigma, St. Louis, Mo., USA), 30% serum substitute BIT 9500 (Stem Cell Tecnologies, Vancouver, BC, Canada), 100 ng/ml Stem Cell Factor (SCF)

(R&D Systems, Minneapolis, Minn., USA) and 4 U/ml Erythropoietin (EPO) (Amgen, Thousand Oaks, Calif., USA) and incubated at 37° C. in a humidified 5% $CO_2$ incubator for seven days. In the second step, the cells were collected by centrifugation and replated in differentiation IMDM media supplemented with 1% penicillin/streptomycin, 1% L-Glutamine, 20 mM β-mercaptoethanol, 1% BSA, 30% BIT 9500 and 4 U/ml EPO and allowed to differentiate for seven additional days.

Phenotypic Characterization of Human Erythroid Cells

Expression of cell surface antigens CD34, CD235a (glycophorin A) and CD36 was evaluated by flow cytometric analysis of immunolabelled cells. Fluorescein (FITC)-conjugated CD34, phycoerythrin (PE)-conjugated CD36 and allophycocyanin (APC)-conjugated CD235a antibodies and the appropriate isotypes control were obtained from Becton Dickinson. Data acquisition and analysis was performed using a BD FACSCanto II flow cytometer and FACS Diva software, respectively (Becton Dickinson, Mountain Blue, Calif., USA). Non-viable cells were excluded from flow cytometric analysis by gating based on positive staining with 7-amino-actinomycin (7-AAD) (Sigma, St. Louis, Mo., USA). Erythroid differentiation was also monitored by Wright-Giemsa staining and microscopic analysis of cytospins.

Example 8

Use of Animal Model for Testing ecPNAs for Treatment of a β-Globin Disorder

Efficacy of the γ-globin specific ecPNAs of the invention can be tested in a humanized mouse model of a β-globin disorder. The mice used in this model have been described. One suitable example is a humanized mouse model of Cooley's Anemia (CA) which has been generated by targeted gene replacement in embryonic stem (ES) cells. In these mice, a delayed switching human γ to β0 globin gene cassette (γβ0) is inserted directly into the murine β globin locus replacing both adult mouse β globin genes. The inserted human β0 globin allele has a mutation in the splice donor site that produces the same aberrant transcripts in mice as described in human cells. No functional human β globin polypeptide chains are produced. Heterozygous γβ0 mice suffer from microcytic anemia. Homozygous γβ0 mice switch from mouse embryonic globin chains to human fetal γ-globin during fetal life. When bred with human α globin knockin mice, homozygous CA mice survive solely upon human fetal hemoglobin at birth. [See, Yongliang Huo et al. et al. (2009) J. Biol. Chem. 284: 4889-4896.]

Bone marrow cells can be isolated from these humanized mice (expressing the human globin genes) and cultured as described above. The γ-globin specific ecPNAs of the invention can be transfected into these cultured bone marrow cells. The transfected cells (1 to $10 \times 10^6$) can be then administered to the transgenic mice via tail vein injection in 200 ml PBS and the efficacy of the transfected cells for treating the β-globin disorder can be assessed by determining the red blood cell count.

Example 9

Induction of iPS Cells from Human CD34+ Peripheral Blood Cells

Mobilized peripheral blood cells are obtained as follows. A donor subject is injected with 5 μg/kg/day for 3 days with Neupogen (G-CSF) manufactured by Amgen. On the fourth day, apheresis of 7 blood volumes is performed on a Cobe Apheresis machine, and 300 ml of blood is collected. Using this method, the yield of CD34+ cells is about 1%. For culture, mobilized peripheral blood CD34+ cells (Allcells, mPB014F) are maintained in IMDM (Invitrogen) containing 15% fetal bovine serum (StemCell Technologies) supplemented with hSCF (100 ng/ml), hFlt3L (100 ng/ml), and Interleukin-3 (20 ng/ml) (Peprotech).

CD34+ cells grown in culture for 4 days are then used for treatment with ecPNA molecules. The cells are treated with a 10 μM cocktail of equal molar concentrations of two ecPNA molecules. The first ePNA molecule has the structure: $H_2N$-CGSDALDDFDLDML-O-$PNA_1$-O-YGRKKRRQRRR ((SEQ ID NO: 27)-O-$PNA_1$-O-(SEQ ID NO: 6)), wherein $PNA_1$ has a nucleic acid sequence that is complementary to a 12 bp sequence in the 200 bp region upstream of the transcription start site of OCT4 gene (see FIG. 7). The second ecPNA molecule has the structure: $H_2N$-CGSDALD-DFDLDML-O-$PNA_2$-O-YGRKKRRQRRR ((SEQ ID NO: 27)-O-$PNA_2$-O-(SEQ ID NO: 6)), wherein $PNA_2$ has a nucleic acid sequence that is complementary to a 12 bp sequence in the 200 bp region upstream of the transcription start site of SOX2 gene (see FIG. 8).

Once iPS cells begin to form in the cultures, embryoid bodies are formed by mechanically scraping confluent undifferentiated CD34 iPS cells into strips and transferring the cells to 6-well, low attachment plates in differentiation medium consisting of knockout DMEM (Invitrogen) supplemented with 20% fetal bovine serum (StemCell Technologies), 0.1 mM non-essential amino acids (Invitrogen), 1 mM L-glutamine (Invitrogen), 50 μg/ml ascorbic acid (Sigma), and 2 mg/ml human holo-transferrin (Sigma) and 0.1 mM β-mercaptoethanol (Sigma).

iPS cells are characterized by immunofluorescent microscopy following immunolabeling with TRA-1-60 (MAB4360, 1:200), TRA-1-81 (MAB4381, 1:200), and SOX2 (AB5603, 1:500) all Chemicon, SSEA-4 (MC-813-70, 1:2), SSEA-3 (MC-631, 1:2) all Iowa, Tuj1 (1:500; Covance), α-fetoprotein (1:400; Dako), α-actinin (1:100; Sigma), OCT4 (C-10, SantaCruz, sc-5279, 1:100), and NANOG (Everest Biotech EB06860, 1:100).

Example 10

Use of ecPNAs to Establish Induced Pluripotent Stem (iPS) Cells

The proximal promoter regions of the OCT4 and SOX2 genes (ie, a 200 bp DNA located upstream of their transcription initiation sites) were divided into 15 base pair sequences against which complementary 15-mer PNA sequences were designed. Four regions in each promoter were selected for synthesis (ie, eight PNA molecules in all; note that all PNA molecules contained biotin for detection).

Figure 19:
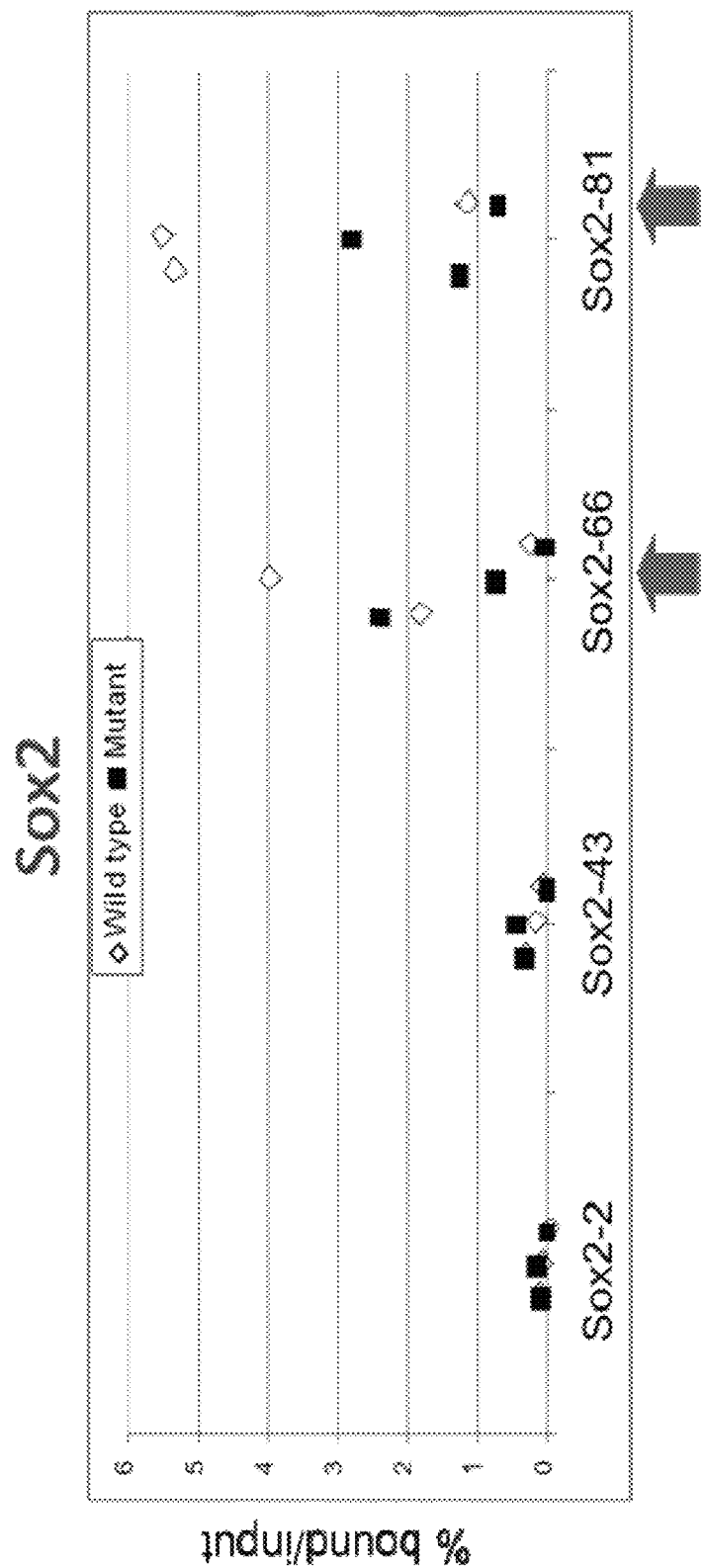
FIG. 19 shows the in vitro target binding specificity of four PNAs designed to interact with the human SOX2 promoter. Sox2-2, -43, -62, and -81 target the proximal promoter region (−1 to −200) of the human SOX2 gene at specific sites. All PNAs contain a biotin molecule attached at their 5'-end. PNAs were incubated with radioactively labeled DNA oligonucleotide containing either the wild type or mutated target sequence followed by incubation with streptavidin Dynabeads and collection with a magnetic particle concentrator. Bound/input percentages were determined after scintillation counter analysis. Arrows indicate molecules selected for further study.
Figure 20:
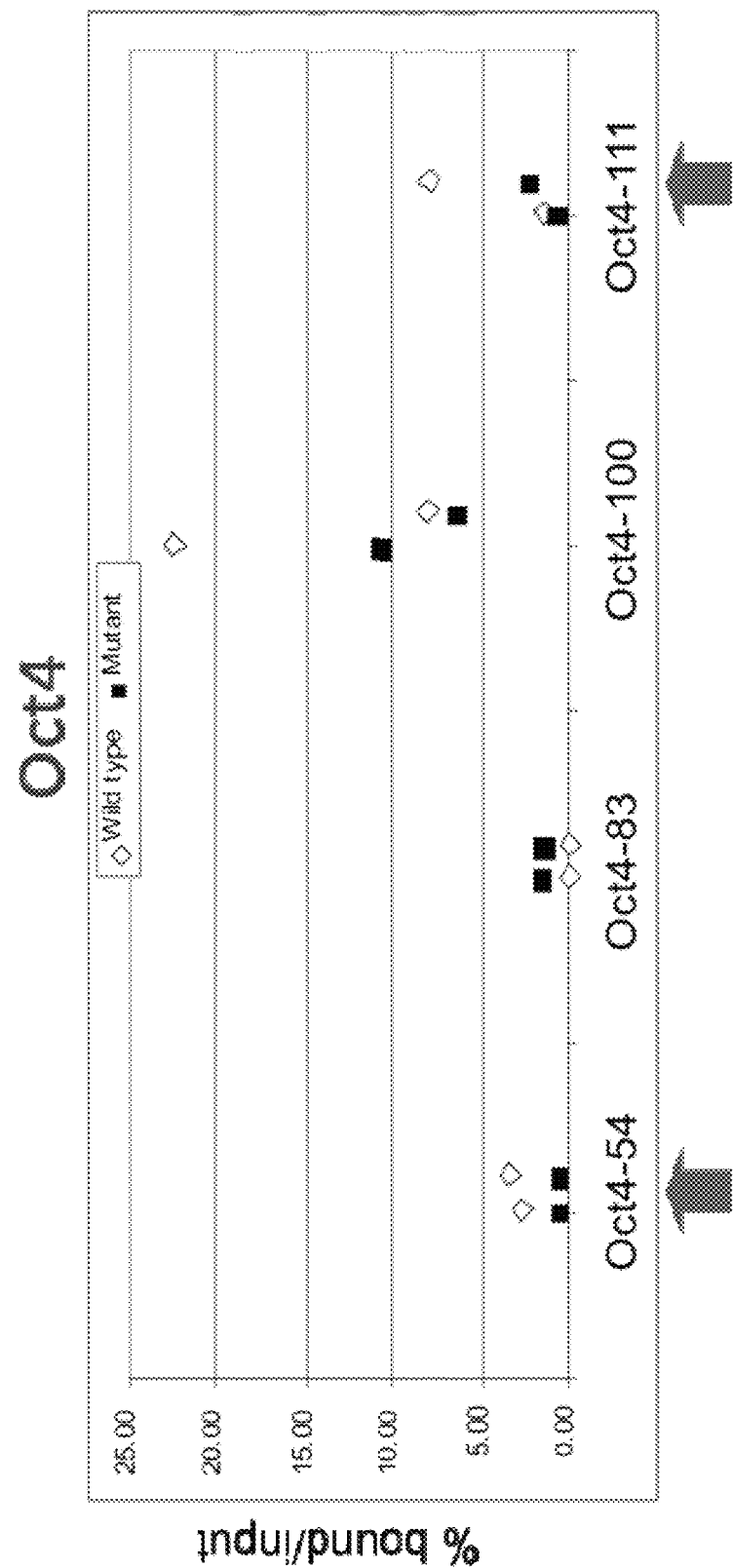
FIG. 20 shows the in vitro target binding specificity of four PNAs designed to interact with the human OCT4 promoter. Oct4-54, -83, -100, and -111 target the proximal promoter region (−1 to −200) of the human OCT4 gene at specific sites. Analyses were performed as in FIG. 19.

These PNAs were tested, along with a mutant variant of each (sixteen total), for selective and specific association with their cognate DNA target by an in vitro binding assay. The results (FIG. 19, three experiments) show that PNAs Sox2-66 and Sox2-81 exhibited better binding to wild-type relative to mutant SOX2 promoter sequences. Using a similar assay (FIG. 20, two experiments), PNAs Oct4-54 and Oct4-111 exhibited reasonable discrimination of wild-type vs mutant OCT4 promoter sequences (note that binding was relatively higher than seen with SOX2, and Oct4-100 had too high a background level for further consideration).

The best two PNA sequences for each of the two promoters formed the basis for the design of ecPNAs for increasing the gene expression of OCT4 and SOX2. The ecPNAs comprised TAT cell/nuclear entry and the transcriptional activation (ATF) motifs, and a the OCT4- or SOX2-specific PNA sequence (four total), and are diagrammed in FIG. 21.

Each of the four ecPNA candidates are tested for efficient cell and nuclear entry and effective activation of OCT4 and SOX2 promoters in cultured fibroblast (293T) cells. The four molecules efficiently enter the 293T cell nucleus, and efficiently activate their specific downstream target (OCT4 or SOX2).

Example 11

Evaluation of ecPNA Molecules that Repress Target Gene Expression

The TAT-PNA78-FOG12 ecPNA repressor was synthesized using the 12 amino acid repression sequence from FOG12: MSRRKQSKPRQI (SEQ ID NO: 47).

Figure 22:
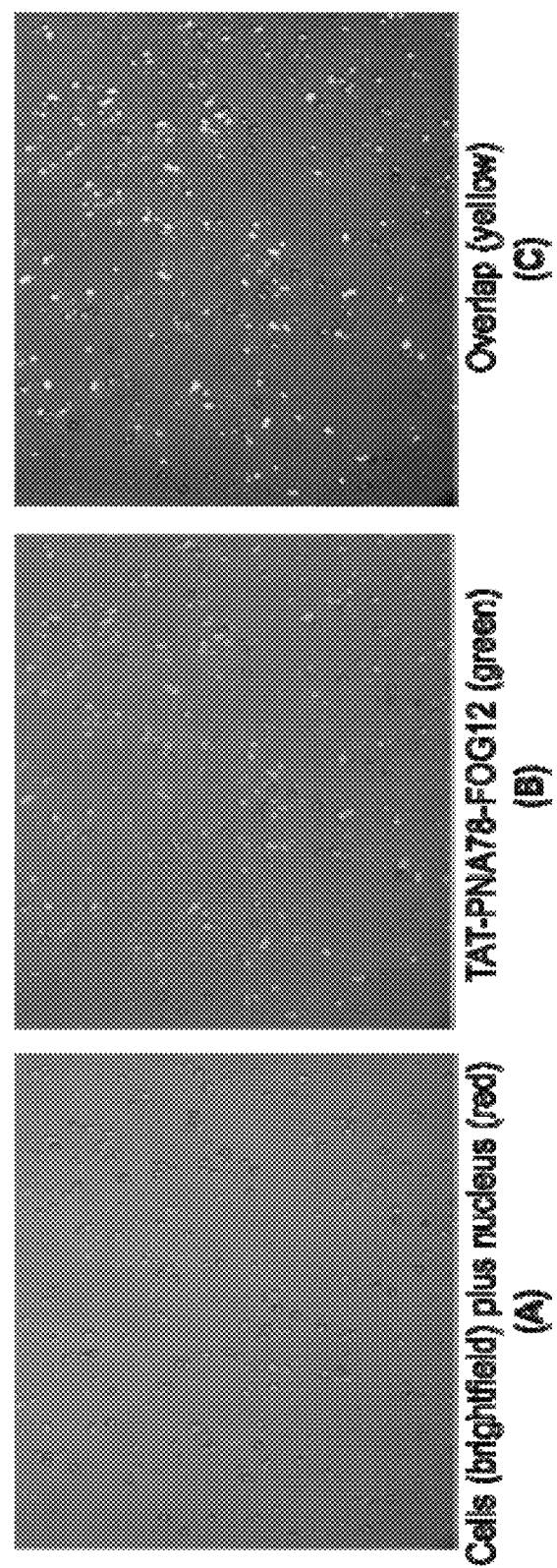
FIG. 22 shows the delivery of TAT-PNA78-FOG12 to K562 cells. Confocal fluorescence microscopy of live K562 cells attached to poly-1-lysine coated is shown. (A) Brightfield picture of cells showing DRAQ5-stained nuclei (red). (B) Presence of intracellular TAT-PNA78-FOG12, visualized by strepavidin-FITC staining (green). (C) Overlay of panels A and B (nuclear and TAT-PNA78-FOG12 staining) shows yellow in areas of overlap (that is, successful entry of TAT-PNA78-FOG12 in the nucleus). Control experiments (cells not exposed to TAT-PNA78-FOG12) do not show any yellow overlap color (not shown).

This ecPNA was tested for cell and nuclear entry into live cells after incubation with K562 cells. K562 cells are a human leukemic cell line, and was also used hereinabove for the evaluation of TAT-PNA78-ATF. These cells constitutively express γ-globin, and are particularly useful for testing repression of that gene by the TAT-PNA78-FOG12 ecPNA. FIG. 22 shows that the TAT-PNA78-FOG12 ecPNA molecule entered the cells and their nuclei efficiently.

The TAT-PNA78-FOG12 ecPNA represses γ globin RNA and protein synthesis.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

While the compositions and methods of this invention have been described in terms of specific embodiments, it will be apparent to those of skill in the art that variations may be applied to the compositions and methods and in the steps or in the sequence of steps of the method described herein without departing from the concept and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the scope of the invention as defined by the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. An embedded chimeric peptide nucleic acid (ecPNA) having the structure H$_2$N-CGSDALDDFDLDML-Biotin-O-TACTCTAAGACTATT-O-YGRKKRRQRRR, wherein each — is a chemical bond.

* * * * *